US007871778B2

(12) United States Patent
Giudice

(10) Patent No.: US 7,871,778 B2
(45) Date of Patent: Jan. 18, 2011

(54) METHODS OF DIAGNOSING ENDOMETRIOSIS

(75) Inventor: Linda C. Giudice, Los Altos Hills, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/109,099

(22) Filed: Apr. 24, 2008

(65) Prior Publication Data

US 2008/0318237 A1  Dec. 25, 2008

Related U.S. Application Data

(60) Provisional application No. 60/914,018, filed on Apr. 25, 2007.

(51) Int. Cl.
*C12Q 1/68* (2006.01)
(52) U.S. Cl. ............................................... 435/6
(58) Field of Classification Search ........................ None
See application file for complete search history.

(56) References Cited

U.S. PATENT DOCUMENTS

2003/0124551 A1* 7/2003 Pappa et al. ..................... 435/6
2004/0005612 A1  1/2004 Giudice et al.

OTHER PUBLICATIONS

Murphy et al. (Adv Physiol Educ. Dec. 2002;26(1-4):256-70).*
Lucentini (The Scientist, 18(24):20).*
Grigoryev et al. (Genome Biol. 2004;5(5):R34. Epub Apr. 27, 2004).*
Flores et al. (Fertil Steril. May 2007;87(5):1180-99).*
Sherwin et al. (Hum Reprod. May 2008;23(5):1063-8. Epub Mar. 19, 2008).*
Eyster et al. (Fertil Steril. Jan. 2002;77(1):38-42).*
Arimoto et al. (Int J Oncol. Mar. 2003;22(3):551-60).*
Matsuzaki et al. (Mol Hum Reprod. Oct. 2004;10(10):719-28. Epub Aug. 6, 2004).*
Attia, Georgia, et al. "Progesterone Receptor Isoform A but not B is expressed in Endometriosis," The Journal of Clinical Endocrinology & Metabolism, vol. 85, No. 8, pp. 2897-28902.
Bulun, SE, et al. "Progesterone resistance in endometriosis: link to failure to metabolize estradiol," Mol. Cell. Endocrinol., 2006, vol. 248, No. 1-2, pp. 94-103.
Cullinan, Emily, et al. "Leukemia inhibitory factor (LIF) and LIF receptor expression in human endometrium suggest a potential autocrine/ paracrine function in regulating embryo implantation," Proc. Natl. Acad. Sci., 1996, vol. 93, pp. 3115-3120.
Igarashi, TM., et al. "Reduced expression of progesterone receptor-B in the endometrium of women with endometriosis and in cocultures of endometrial cells exposed to 2,3,7,8- tetracholordibenzo-p-dioxin," Fertil Steril, 2005, vol. 84, No. 1 pp. 67-74.
Kamat, A., et al., "Protein expression profiling of endometriosis: Validation of 2-mm tissue microarrays," Fertility and Sterility, 2004, vol. 82, Issue 6, pp. 1681-1683.

Kao, L.C., et al. "Expression Profiling of Endometrium from Women with Endometriosis Reveals Candidate Genes for Disease Based Implantation Failure and Infertility," Endocrinology, 2008, vol. 144, No. 7, pp. 2870-2881.
Lessey, Bruce, et al. "Aberrant Integrin Expression in the Endometrium of Women with Endometriosis," Journal of Clinical Endocrinology and Metabolism, 2004, vol. 79, No. 2, pp. 643-649.
Lessey, Bruce, et al. "Integrin Adhesion molecules in the Human Endometrium; Correlation with the Normal and Abnormal Menstrual Cycle," 1992, vol. 90, pp. 188-195.
Osteen, KG, et al. "Reduced progesterone action during endometrial maturation: a potential risk factor for the development of endometriosis,", Fertil Steril, 2005, vol. 83, No. 3, pp. 529-537.
Taylor, Hugh S., et al. "HOX gene expression is altered in the endometrium of women with endometriosis," Human Reproduction, 1999, vol. 14, No. 5, pp. 1328-1331.
Vierikko, P., et al. "Steroidal regulation of endometriosis tissue: lack of induction of 17 beta-hydroxysteroid dehydrogenase activity by progesterone, medroxyprogesterone acetate, or danazol." Fertil. Steril., 1985, vol. 14, No. 2, pp. 218-224.
Talbi, S. et al., "Molecular Phenotyping of Human Endometrium Distinguishes Menstrual Cycle Phases and Underlying Biological Processes in Normo-Ovulatory Women," *Endocrinology* (Mar. 2006), 147(3):1097-1121.
Burney, Richard O. et al., "Gene Expression Profiling of Eutopic Endometrium from Women with Moderate-Severe Endometriosis," presented at the SRM meeting Oct. 21-25, 2006.
Burney, Richard O. et al., "Gene Expression Analysis of Endometrium Reveals Progesterone Resistance and Candidate Susceptibility Genes in Women with Endometriosis," *Endocrinology* (Aug. 2007), 148(8):3814-3826.
Burney, Richard O. et al., "Molecular Profiling Reveals Progesterone Resistance in the Eutopic Endometrium of Women with Endometriosis," presented at the 2nd SGI International Summit held Nov. 7, 2007.

* cited by examiner

*Primary Examiner*—Christopher M. Babic
(74) *Attorney, Agent, or Firm*—Townsend and Townsend and Crew LLP

(57) ABSTRACT

The present invention provides biomarkers for the diagnosis and prognosis of endometriosis. Generally, the methods of this invention find use in diagnosing or for providing a prognosis for endometriosis by detecting the expression levels of biomarkers, which are differentially expressed (up- or down-regulated) in endometrial cells from a patient with endometriosis. Similarly, these markers can be used to diagnose reduced fertility in a patient with endometriosis or to provide a prognosis for a fertility trial in a patient suffering from endometriosis. The present invention also provides methods of identifying a compound for treating or preventing endometriosis. Finally, the present invention provides kits for the diagnosis or prognosis of endometriosis.

18 Claims, 28 Drawing Sheets

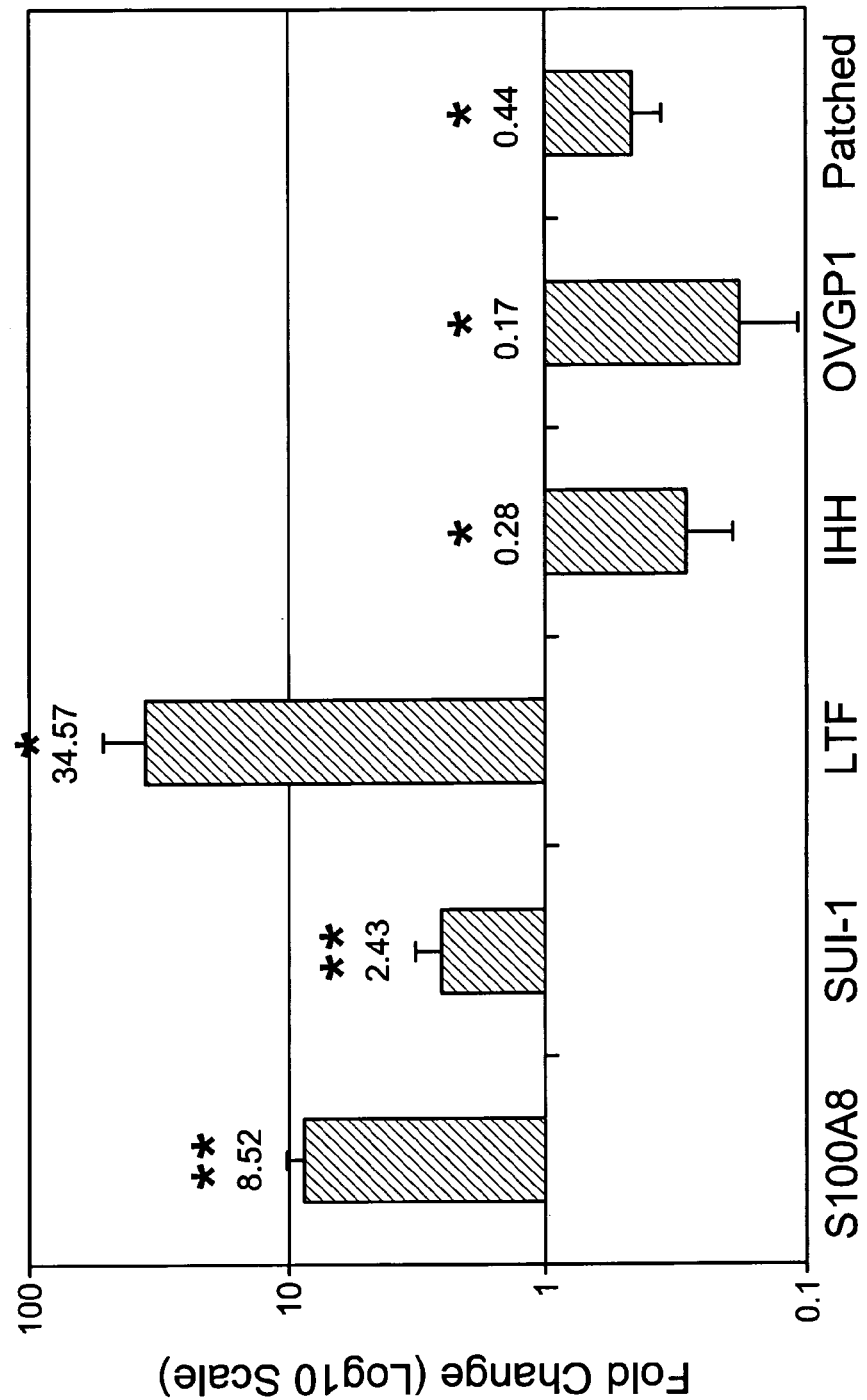
Fig. 3 (sheet 1)

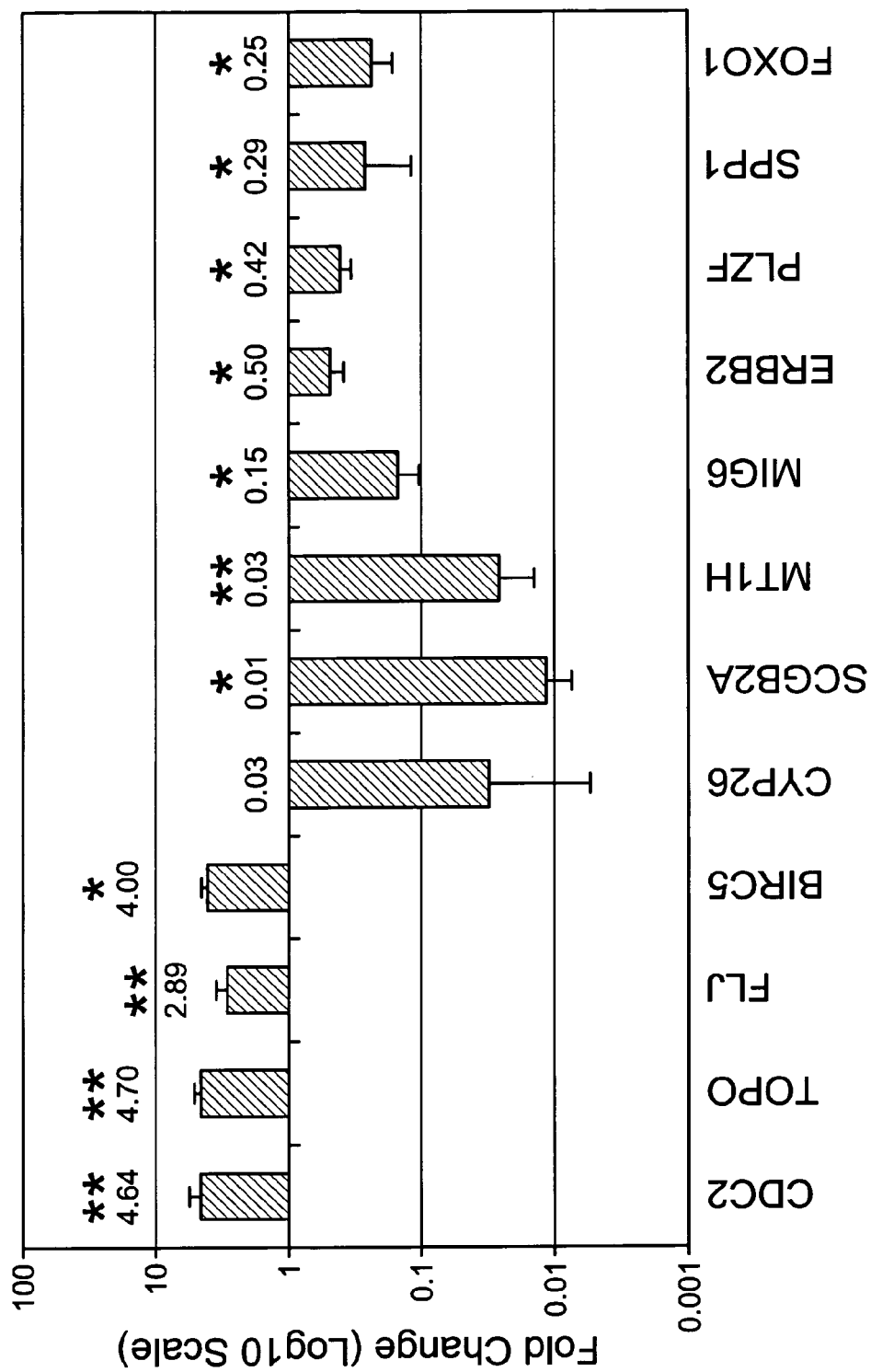
Fig. 3 (sheet 2)

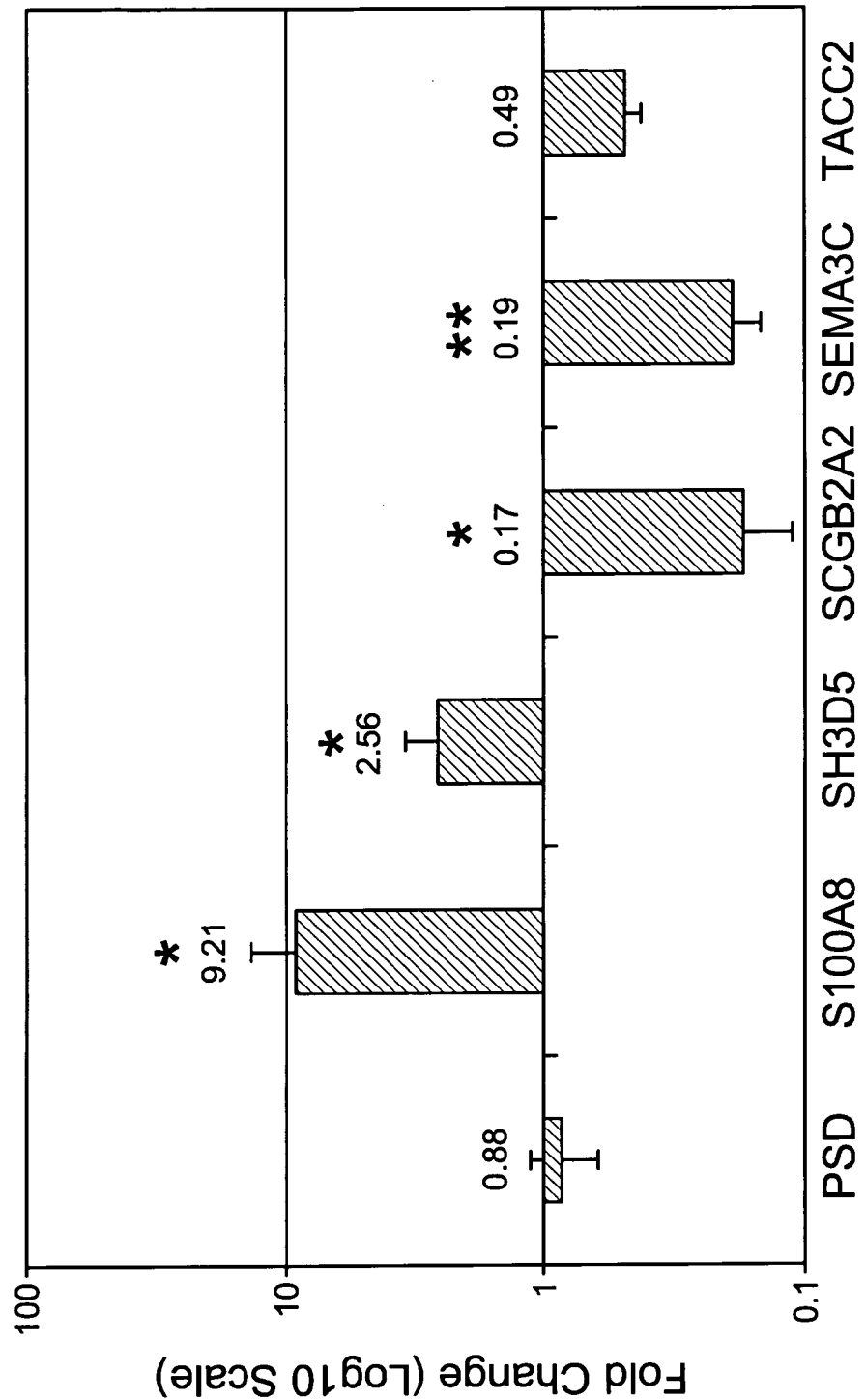
Fig. 3 (sheet 3)

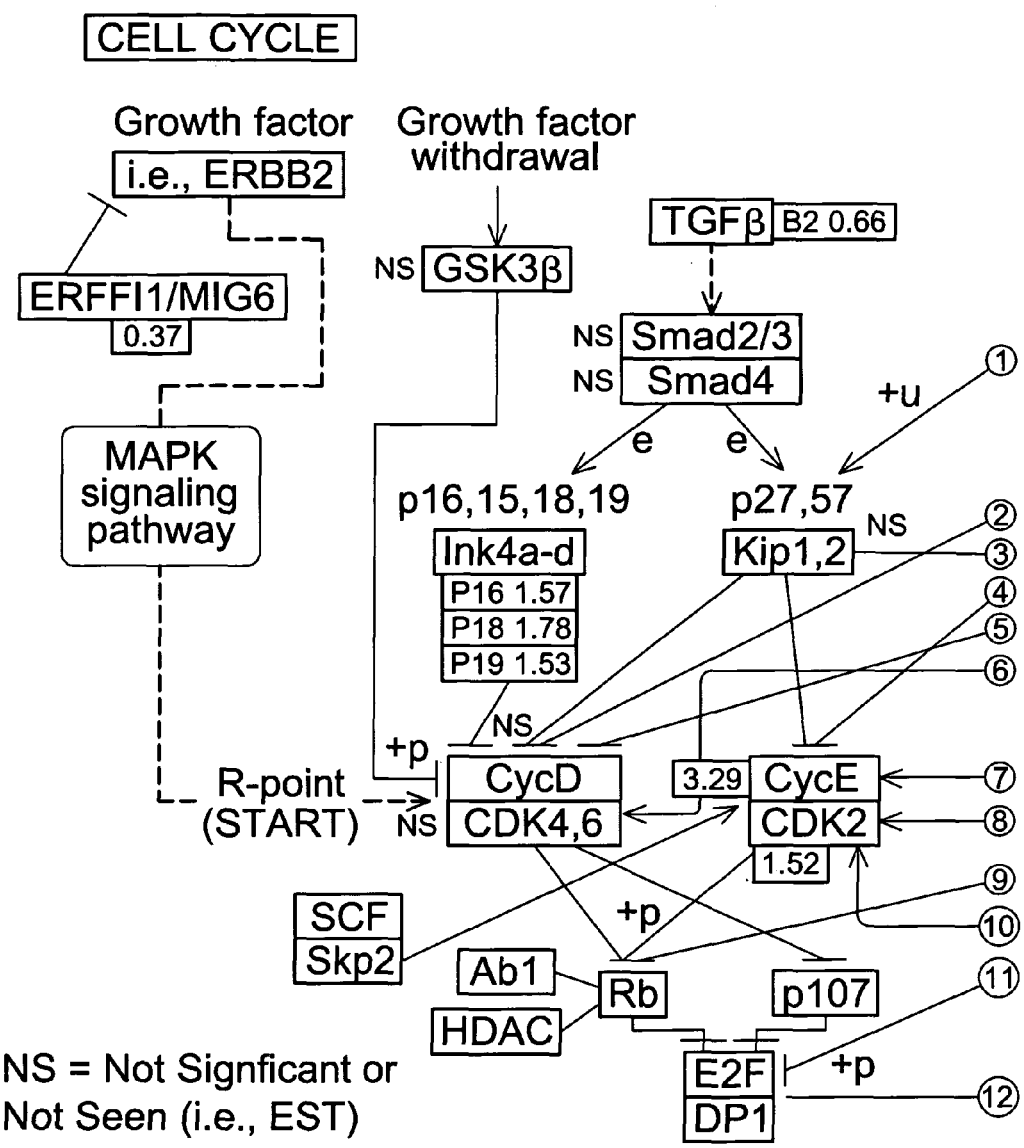
Fig. 4 (sheet 1)

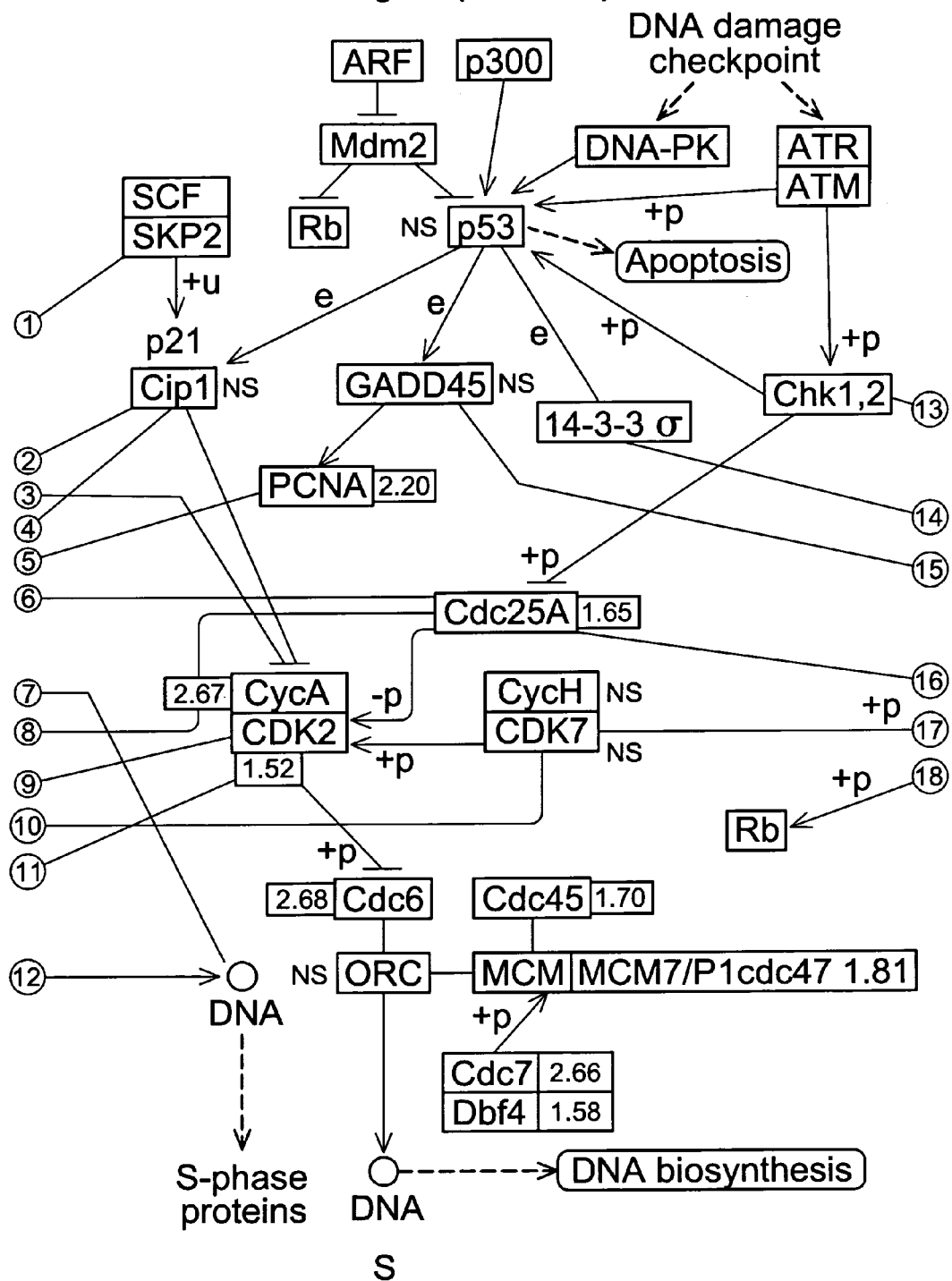
Fig. 4 (sheet 2)

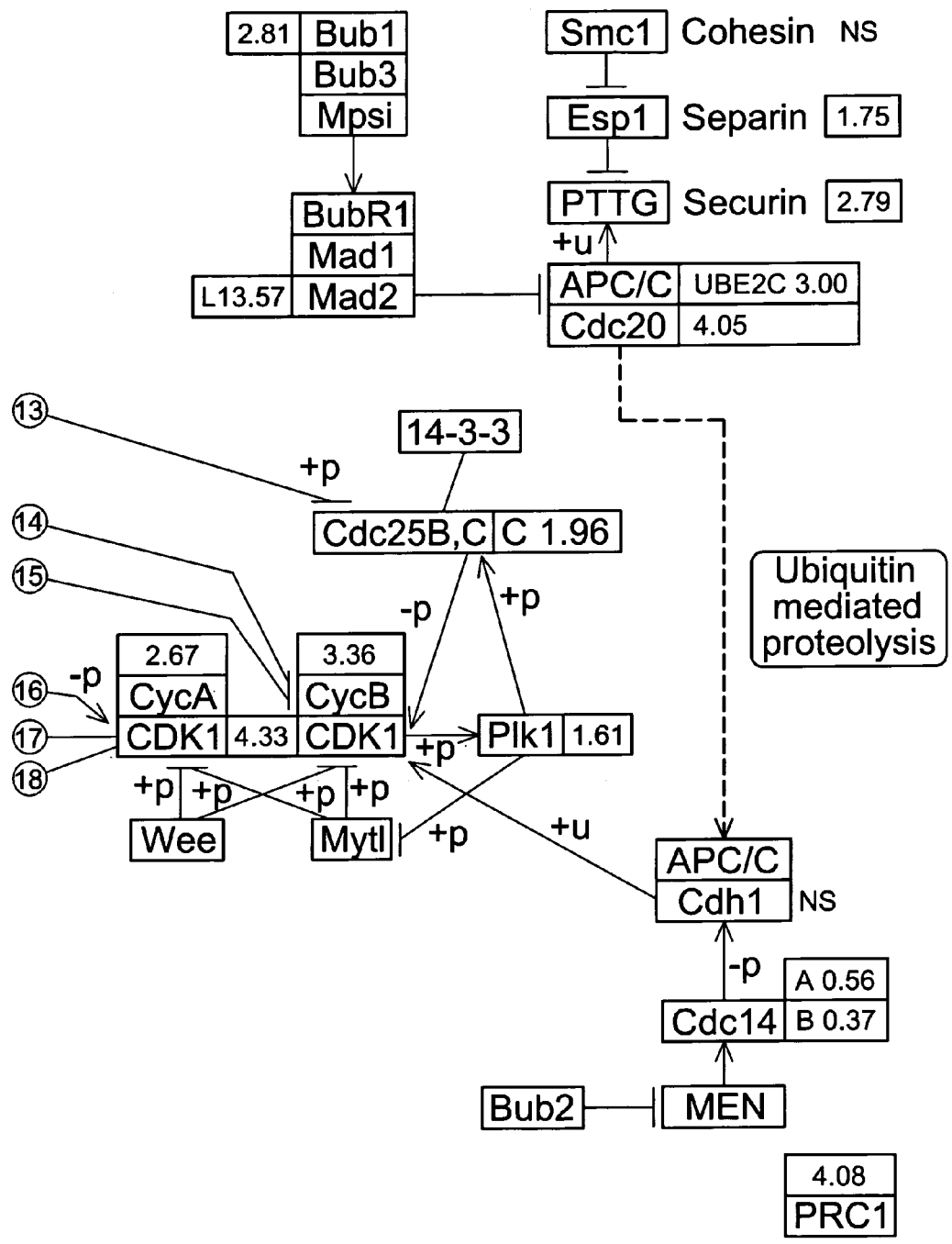
Fig. 4 (sheet 3)

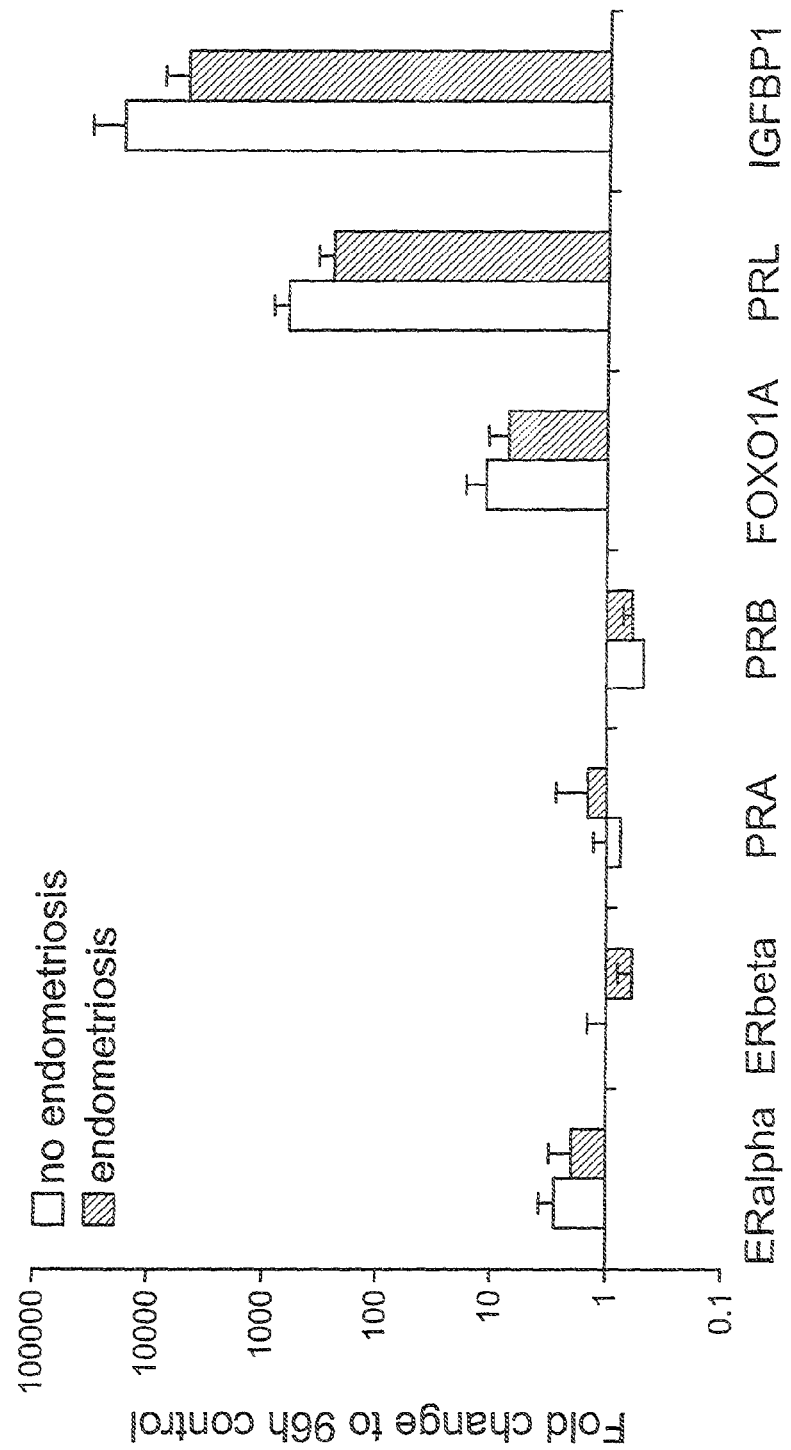

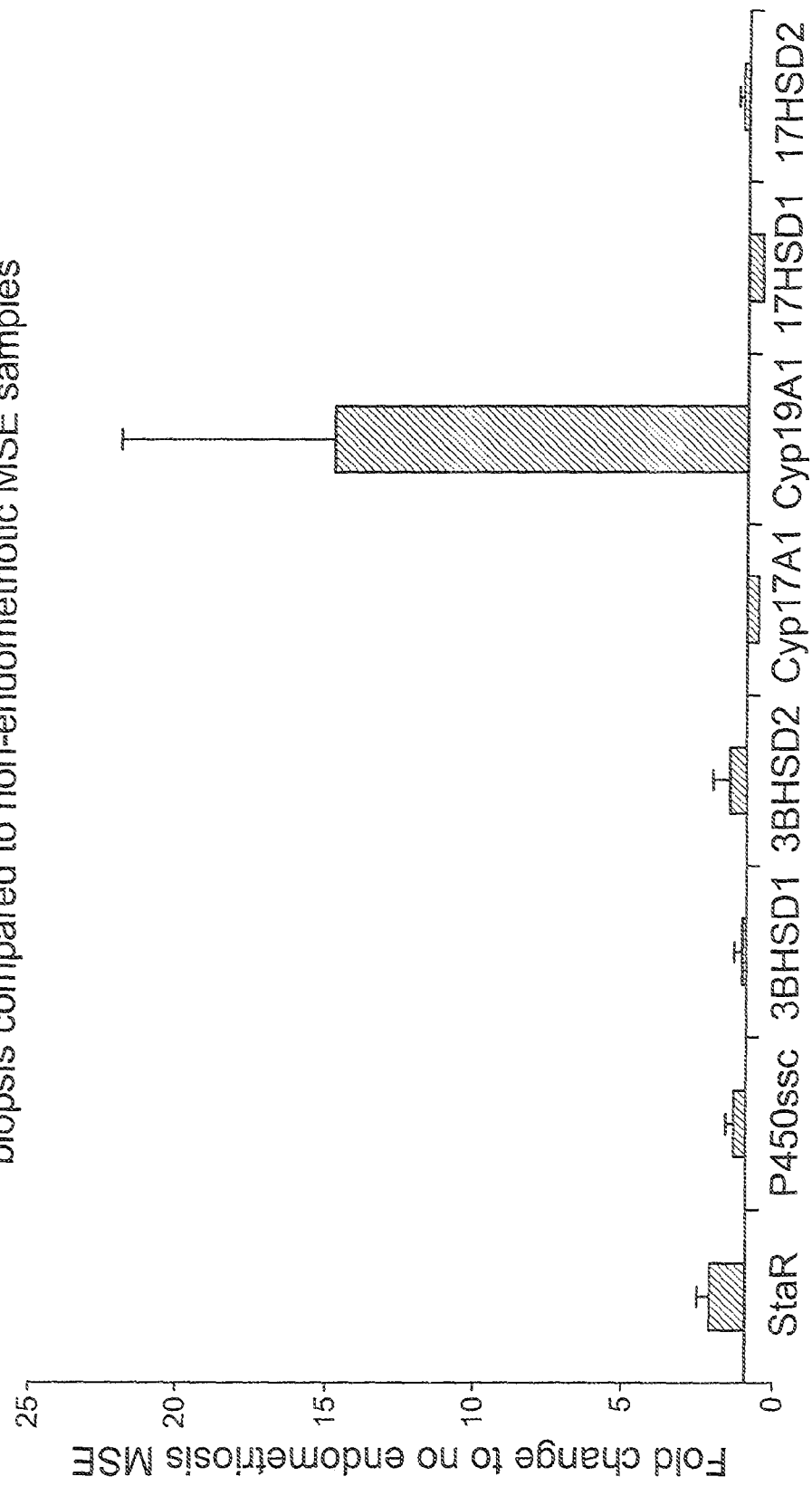

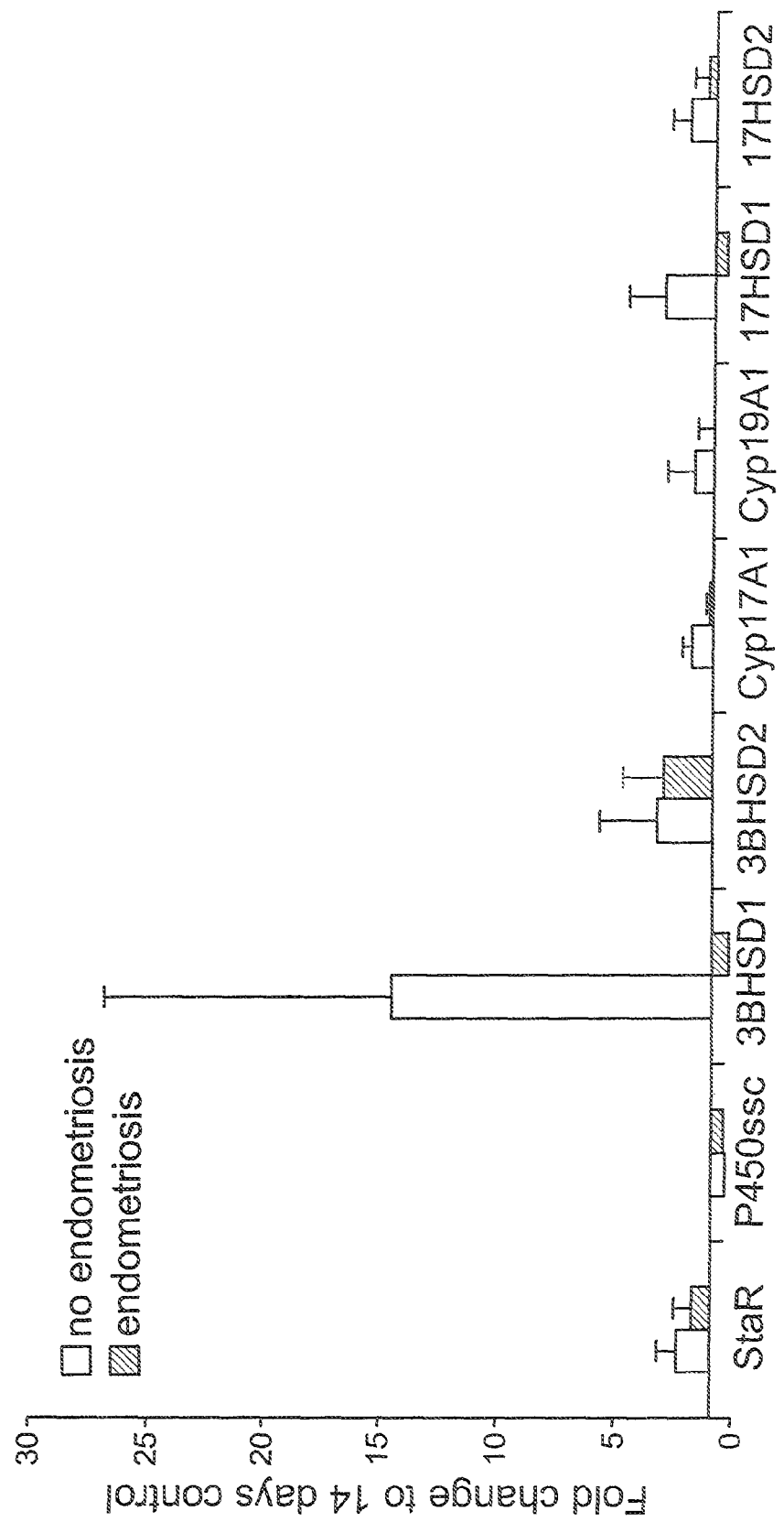

Fig. 18
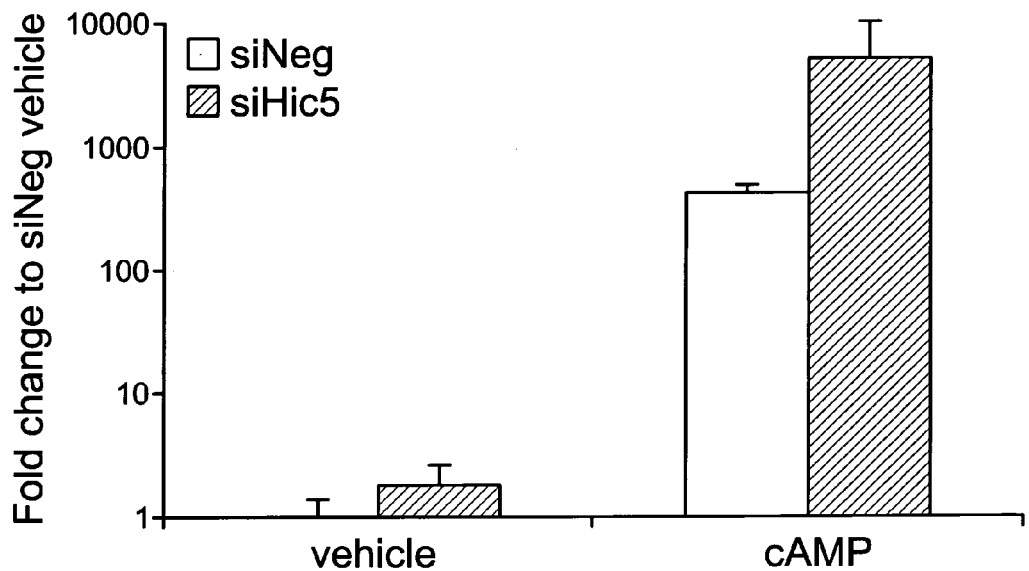
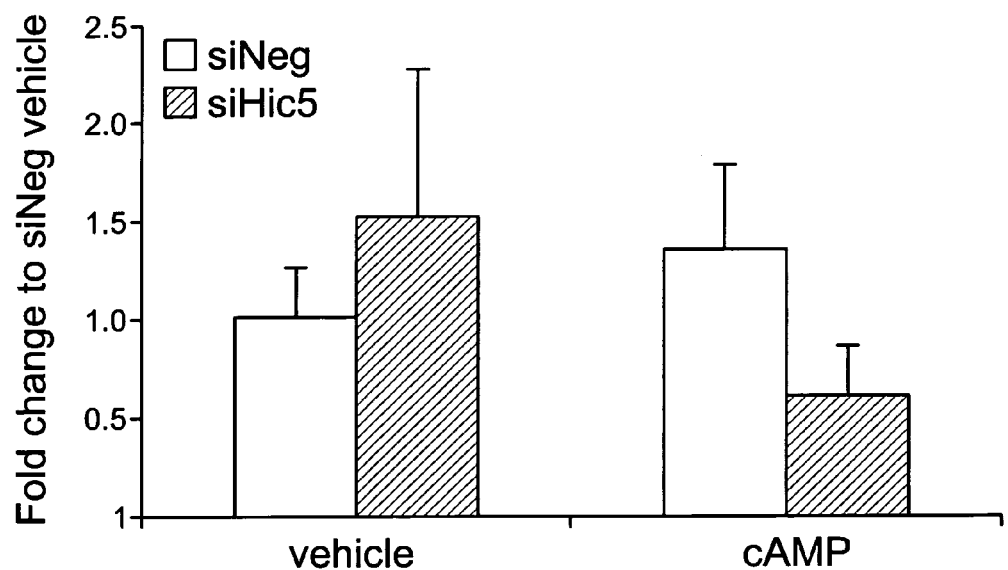

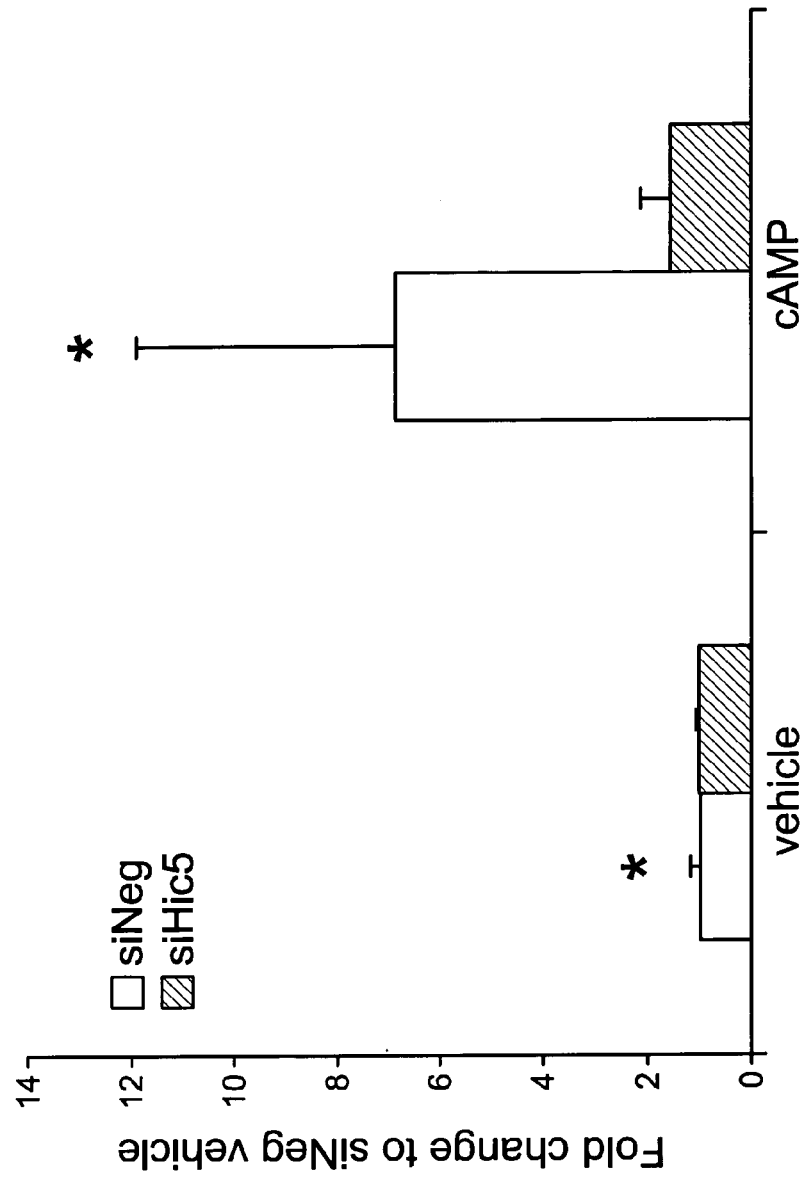

SEQUENCE LISTING

```
<160> NUMBER OF SEQ ID NOS: 45

<210> SEQ ID NO 1
<211> LENGTH: 22
<212> TYPE: DNA
<213> ORGANISM: Artificial Sequence
<220> FEATURE:
<223> OTHER INFORMATION: S100 calcium binding protein A8 (S100A8,
      calgranulin A (CAGA, CGLA), cystic fibrosis antigen (CFAG),
      calprotectin L1L subunit (L1Ag), myeloid-related protein 8 (MRP8))
      real-time PCR intron spanning forward primer

<400> SEQUENCE: 1
cagctgtctt tcagaagacc tg                                              22

<210> SEQ ID NO 2
<211> LENGTH: 21
<212> TYPE: DNA
<213> ORGANISM: Artificial Sequence
<220> FEATURE:
<223> OTHER INFORMATION: S100 calcium binding protein A8 (S100A8,
      calgranulin A (CAGA, CGLA), cystic fibrosis antigen (CFAG),
      calprotectin L1L subunit (L1Ag), myeloid-related protein 8 (MRP8))
      real-time PCR intron spanning reverse primer

<400> SEQUENCE: 2
tgaggacact cggtctctag c                                               21

<210> SEQ ID NO 3
<211> LENGTH: 20
<212> TYPE: DNA
<213> ORGANISM: Artificial Sequence
<220> FEATURE:
<223> OTHER INFORMATION: putative translation initiation factor SUI1
``` real-time PCR intron spanning forward primer

<400> SEQUENCE: 3
attgagcatc cggaatatgg                                               20

<210> SEQ ID NO 4
<211> LENGTH: 20
<212> TYPE: DNA
<213> ORGANISM: Artificial Sequence
<220> FEATURE:
<223> OTHER INFORMATION: putative translation initiation factor SUI1
      real-time PCR intron spanning reverse primer

<400> SEQUENCE: 4
tgatcgtcct tagccagtcc                                               20

<210> SEQ ID NO 5
<211> LENGTH: 20
<212> TYPE: DNA
<213> ORGANISM: Artificial Sequence
<220> FEATURE:
<223> OTHER INFORMATION: lactotransferrin (LTF, lactoferrin (LF),
      talactoferrin) real-time PCR intron spanning forward primer

<400> SEQUENCE: 5
gactccatgg caaaacaaca                                               20

<210> SEQ ID NO 6
<211> LENGTH: 20
<212> TYPE: DNA
<213> ORGANISM: Artificial Sequence
<220> FEATURE:
<223> OTHER INFORMATION: lactotransferrin (LTF, lactoferrin (LF),
      talactoferrin) real-time PCR intron spanning reverse primer

<400> SEQUENCE: 6
gaggaattca caggcttcca                                               20

<210> SEQ ID NO 7
<211> LENGTH: 20
<212> TYPE: DNA
<213> ORGANISM: Artificial Sequence
<220> FEATURE:
<223> OTHER INFORMATION: Indian hedgehog homolog (IHH, HHG-2,
      brachydactyly type A1 (BDA1)) real-time PCR intron spanning
      forward primer

<400> SEQUENCE: 7
cggctttgac tgggtgtatt                                               20

<210> SEQ ID NO 8
<211> LENGTH: 20
<212> TYPE: DNA
<213> ORGANISM: Artificial Sequence
<220> FEATURE:
<223> OTHER INFORMATION: Indian hedgehog homolog (IHH, HHG-2,
      brachydactyly type A1 (BDA1)) real-time PCR intron spanning
      reverse primer

<400> SEQUENCE: 8
gaaaatgagc acatcgctga                                               20

<210> SEQ ID NO 9
<211> LENGTH: 21
<212> TYPE: DNA
<213> ORGANISM: Artificial Sequence
<220> FEATURE:

```
<223> OTHER INFORMATION: patched homolog 1 (Drosophila) (PTCH1, PTC,
      PTC1, holoprosencephaly 7 (HPE7), basal cell nevus syndrome
      (BCNS)) real-time PCR intron spanning forward primer

<400> SEQUENCE: 9
tcgaaggtgg aagtcattga g                                              21

<210> SEQ ID NO 10
<211> LENGTH: 21
<212> TYPE: DNA
<213> ORGANISM: Artificial Sequence
<220> FEATURE:
<223> OTHER INFORMATION: patched homolog 1 (Drosophila) (PTCH1, PTC,
      PTC1, holoprosencephaly 7 (HPE7), basal cell nevus syndrome
      (BCNS)) real-time PCR intron spanning reverse primer

<400> SEQUENCE: 10
cacagggcat cttttccata a                                              21

<210> SEQ ID NO 11
<211> LENGTH: 20
<212> TYPE: DNA
<213> ORGANISM: Artificial Sequence
<220> FEATURE:
<223> OTHER INFORMATION: oviductal glycoprotein 1 precursor (OVGP1, OGP,
      mucin 9 (MUC9), oviductin, estrogen-dependent oviduct protein)
      real-time PCR intron spanning forward primer

<400> SEQUENCE: 11
tatgtcccgt atgccaacaa                                                20

<210> SEQ ID NO 12
<211> LENGTH: 20
<212> TYPE: DNA
<213> ORGANISM: Artificial Sequence
<220> FEATURE:
<223> OTHER INFORMATION: oviductal glycoprotein 1 precursor (OVGP1, OGP,
      mucin 9 (MUC9), oviductin, estrogen-dependent oviduct protein)
      real-time PCR intron spanning reverse primer

<400> SEQUENCE: 12
acgtagacaa gggggaaagg                                                20

<210> SEQ ID NO 13
<211> LENGTH: 21
<212> TYPE: DNA
<213> ORGANISM: Artificial Sequence
<220> FEATURE:
<223> OTHER INFORMATION: topoisomerase (DNA) II alpha 170kDa (TOP2A)
      real-time PCR intron spanning forward primer

<400> SEQUENCE: 13
aagccctcct gctacacatt t                                              21

<210> SEQ ID NO 14
<211> LENGTH: 21
<212> TYPE: DNA
<213> ORGANISM: Artificial Sequence
<220> FEATURE:
<223> OTHER INFORMATION: topoisomerase (DNA) II alpha 170kDa (TOP2A)
      real-time PCR intron spanning reverse primer

<400> SEQUENCE: 14
caggcttttg agagacacca g                                              21

<210> SEQ ID NO 15
<211> LENGTH: 21
```

```
<212> TYPE: DNA
<213> ORGANISM: Artificial Sequence
<220> FEATURE:
<223> OTHER INFORMATION: cyclin-dependent kinase 1 (CDK1, cell division
      control protein 2 (CDC2), p34 protein kinase)
      real-time PCR intron spanning forward primer

<400> SEQUENCE: 15
gcttatgcag gattccaggt t                                             21

<210> SEQ ID NO 16
<211> LENGTH: 21
<212> TYPE: DNA
<213> ORGANISM: Artificial Sequence
<220> FEATURE:
<223> OTHER INFORMATION: cyclin-dependent kinase 1 (CDK1, cell division
      control protein 2 (CDC2), p34 protein kinase)
      real-time PCR intron spanning reverse primer

<400> SEQUENCE: 16
caatcccctg taggatttgg t                                             21

<210> SEQ ID NO 17
<211> LENGTH: 21
<212> TYPE: DNA
<213> ORGANISM: Artificial Sequence
<220> FEATURE:
<223> OTHER INFORMATION: centrosomal protein 55 kDa ((CEP55), FLJ10540)
      real-time PCR intron spanning forward primer

<400> SEQUENCE: 17
ctcaagaccg ttgtctcttc g                                             21

<210> SEQ ID NO 18
<211> LENGTH: 21
<212> TYPE: DNA
<213> ORGANISM: Artificial Sequence
<220> FEATURE:
<223> OTHER INFORMATION: centrosomal protein 55 kDa ((CEP55), FLJ10540)
      real-time PCR intron spanning reverse primer

<400> SEQUENCE: 18
ttcccacttg tgatttcatc c                                             21

<210> SEQ ID NO 19
<211> LENGTH: 21
<212> TYPE: DNA
<213> ORGANISM: Artificial Sequence
<220> FEATURE:
<223> OTHER INFORMATION: metallothionein 1H (MT1H) real-time PCR intron
      spanning forward primer

<400> SEQUENCE: 19
gcaagtgcaa aaagtgcaaa t                                             21

<210> SEQ ID NO 20
<211> LENGTH: 20
<212> TYPE: DNA
<213> ORGANISM: Artificial Sequence
<220> FEATURE:
<223> OTHER INFORMATION: metallothionein 1H (MT1H) real-time PCR intron
      spanning reverse primer

<400> SEQUENCE: 20
cacttctctg acgccccttt                                               20

<210> SEQ ID NO 21
```

```
<210> SEQ ID NO 21
<211> LENGTH: 21
<212> TYPE: DNA
<213> ORGANISM: Artificial Sequence
<220> FEATURE:
<223> OTHER INFORMATION: secretoglobin, family 2A, member 2 (SCGB2A2,
      mammaglobin 1, mammaglobin A (MGB1), uteroglobin 2
      (UGB2)) real-time PCR intron spanning forward primer

<400> SEQUENCE: 21
accatgaagt tgctgatggt c                                             21

<210> SEQ ID NO 22
<211> LENGTH: 21
<212> TYPE: DNA
<213> ORGANISM: Artificial Sequence
<220> FEATURE:
<223> OTHER INFORMATION: secretoglobin, family 2A, member 2 (SCGB2A2,
      mammaglobin 1, mammaglobin A (MGB1), uteroglobin 2
      (UGB2)) real-time PCR intron spanning reverse primer

<400> SEQUENCE: 22
ggcatttgta gtggcattgt c                                             21

<210> SEQ ID NO 23
<211> LENGTH: 19
<212> TYPE: DNA
<213> ORGANISM: Artificial Sequence
<220> FEATURE:
<223> OTHER INFORMATION: cytochrome P450, subfamily XXVIA, polypeptide
      1, cytochrome P450, family 26, subfamily A, polypeptide 1,
      (CYP26A1), P450 retinoic acid-inactivating 1 (P450RAI1), retinoic
      acid 4-hydrolase real-time PCR intron spanning forward primer

<400> SEQUENCE: 23
gcatcgagca gaacattcg                                                19

<210> SEQ ID NO 24
<211> LENGTH: 21
<212> TYPE: DNA
<213> ORGANISM: Artificial Sequence
<220> FEATURE:
<223> OTHER INFORMATION: cytochrome P450, subfamily XXVIA, polypeptide
      1, cytochrome P450, family 26, subfamily A, polypeptide 1,
      (CYP26A1), P450 retinoic acid-inactivating 1 (P450RAI1), retinoic
      acid 4-hydrolase real-time PCR intron spanning reverse primer

<400> SEQUENCE: 24
tggagaacat gtgggtagag c                                             21

<210> SEQ ID NO 25
<211> LENGTH: 21
<212> TYPE: DNA
<213> ORGANISM: Artificial Sequence
<220> FEATURE:
<223> OTHER INFORMATION: pleckstrin and Sec7 domain containing (PSD)
      real-time PCR intron spanning forward primer

<400> SEQUENCE: 25
agctcccaaa agaagttcag c                                             21

<210> SEQ ID NO 26
<211> LENGTH: 21
<212> TYPE: DNA
<213> ORGANISM: Artificial Sequence
<220> FEATURE:
<223> OTHER INFORMATION: pleckstrin and Sec7 domain containing (PSD)
      real-time PCR intron spanning reverse primer

<400> SEQUENCE: 26
```
actccaggta ggcctccttc t                                             21

<210> SEQ ID NO 27
<211> LENGTH: 22
<212> TYPE: DNA
<213> ORGANISM: Artificial Sequence
<220> FEATURE:
<223> OTHER INFORMATION: SH3-domain protein 5 (SH3D5), sorbin and SH3
      domain containing 1 (SORBS1, ponsin) real-time PCR
      intron spanning forward primer

<400> SEQUENCE: 27
ccacagaatg atgatgagtt gg                                            22

<210> SEQ ID NO 28
<211> LENGTH: 21
<212> TYPE: DNA
<213> ORGANISM: Artificial Sequence
<220> FEATURE:
<223> OTHER INFORMATION: SH3-domain protein 5 (SH3D5), sorbin and SH3
      domain containing 1 (SORBS1, ponsin) real-time PCR
      intron spanning reverse primer

<400> SEQUENCE: 28
gttgcctgga aaagtaccaa a                                             21

<210> SEQ ID NO 29
<211> LENGTH: 21
<212> TYPE: DNA
<213> ORGANISM: Artificial Sequence
<220> FEATURE:
<223> OTHER INFORMATION: transforming, acidic coiled-coil containing
      protein 2 (TACC2) real-time PCR intron spanning
      forward primer

<400> SEQUENCE: 29
aggagagccc tgtcaagtca t                                             21

<210> SEQ ID NO 30
<211> LENGTH: 21
<212> TYPE: DNA
<213> ORGANISM: Artificial Sequence
<220> FEATURE:
<223> OTHER INFORMATION: transforming, acidic coiled-coil containing
      protein 2 (TACC2) real-time PCR intron spanning
      reverse primer

<400> SEQUENCE: 30
cttctgggag gatttctctg g                                             21

<210> SEQ ID NO 31
<211> LENGTH: 21
<212> TYPE: DNA
<213> ORGANISM: Artificial Sequence
<220> FEATURE:
<223> OTHER INFORMATION: sema domain, immunoglobulin domain (Ig), short
      basic domain, secreted, (semaphorin) 3C (SEMA3C,
      semaphorin E (SEMAE, SemE)) real-time PCR intron
      spanning forward primer

<400> SEQUENCE: 31
aagtctccgc aggcatctat c                                             21

<210> SEQ ID NO 32
<211> LENGTH: 21
<212> TYPE: DNA
<213> ORGANISM: Artificial Sequence

```
<220> FEATURE:
<223> OTHER INFORMATION: sema domain, immunoglobulin domain (Ig), short
      basic domain, secreted, (semaphorin) 3C (SEMA3C,
      semaphorin E (SEMAE, SemE)) real-time PCR intron
      spanning reverse primer

<400> SEQUENCE: 32
caacagccac catttctgaa t                                              21

<210> SEQ ID NO 33
<211> LENGTH: 21
<212> TYPE: DNA
<213> ORGANISM: Artificial Sequence
<220> FEATURE:
<223> OTHER INFORMATION: baculoviral IAP repeat-containing protein 5
      (BIRC5, apoptosis inhibitor 4 (API4), effector cell peptidase
      receptor 1 (EPR-1), survivin variant 3 alpha) real-time
      PCR intron spanning forward primer

<400> SEQUENCE: 33
cactgagaac gagccagact t                                              21

<210> SEQ ID NO 34
<211> LENGTH: 21
<212> TYPE: DNA
<213> ORGANISM: Artificial Sequence
<220> FEATURE:
<223> OTHER INFORMATION: baculoviral IAP repeat-containing protein 5
      (BIRC5, apoptosis inhibitor 4 (API4), effector cell peptidase
      receptor 1 (EPR-1), survivin variant 3 alpha) real-time
      PCR intron spanning reverse primer

<400> SEQUENCE: 34
aaccggacga atgcttttta t                                              21

<210> SEQ ID NO 35
<211> LENGTH: 20
<212> TYPE: DNA
<213> ORGANISM: Artificial Sequence
<220> FEATURE:
<223> OTHER INFORMATION: ERBB receptor feedback inhibitor 1 (ERRFI1),
      mitogen-inducible gene 6 protein (MIG6,
      receptor-associated late transducer (RALT))
      real-time PCR intron spanning forward primer

<400> SEQUENCE: 35
ttgctgctca ggagatcaga                                                20

<210> SEQ ID NO 36
<211> LENGTH: 21
<212> TYPE: DNA
<213> ORGANISM: Artificial Sequence
<220> FEATURE:
<223> OTHER INFORMATION: ERBB receptor feedback inhibitor 1 (ERRFI1),
      mitogen-inducible gene 6 protein (MIG6,
      receptor-associated late transducer (RALT))
      real-time PCR intron spanning reverse primer

<400> SEQUENCE: 36
ttcagactgt aggccatggt t                                              21

<210> SEQ ID NO 37
<211> LENGTH: 21
<212> TYPE: DNA
<213> ORGANISM: Artificial Sequence
<220> FEATURE:
<223> OTHER INFORMATION: V-erb-b2 erythroblastic leukemia viral homolog
      2 (ERBB2, erbB-2, neuro/glioblastoma derived oncogene homolog
      (avian), HER-2/neu tyrosine kinase-type receptor (TKR1),
``` herstatin) real-time PCR intron spanning forward primer

<400> SEQUENCE: 37
ccctggtcac ctacaacaca g                                          21

<210> SEQ ID NO 38
<211> LENGTH: 21
<212> TYPE: DNA
<213> ORGANISM: Artificial Sequence
<220> FEATURE:
<223> OTHER INFORMATION: V-erb-b2 erythroblastic leukemia viral homolog
      2 (ERBB2, erbB-2, neuro/glioblastoma derived oncogene homolog
      (avian), HER-2/neu tyrosine kinase-type receptor (TKR1),
      herstatin) real-time PCR intron spanning reverse primer

<400> SEQUENCE: 38
ctctgctgtc acctcttggt t                                          21

<210> SEQ ID NO 39
<211> LENGTH: 20
<212> TYPE: DNA
<213> ORGANISM: Artificial Sequence
<220> FEATURE:
<223> OTHER INFORMATION: forkhead box O1A, forkhead homolog 1 (FOXO1A,
      FOXO1, FKHR, FKH1) real-time PCR intron spanning
      forward primer

<400> SEQUENCE: 39
aagagcgtgc cctacttcaa                                            20

<210> SEQ ID NO 40
<211> LENGTH: 20
<212> TYPE: DNA
<213> ORGANISM: Artificial Sequence
<220> FEATURE:
<223> OTHER INFORMATION: forkhead box O1A, forkhead homolog 1 (FOXO1A,
      FOXO1, FKHR, FKH1) real-time PCR intron spanning
      reverse primer

<400> SEQUENCE: 40
ctgttgttgt ccatggatgc                                            20

<210> SEQ ID NO 41
<211> LENGTH: 20
<212> TYPE: DNA
<213> ORGANISM: Artificial Sequence
<220> FEATURE:
<223> OTHER INFORMATION: promyelocytic leukemia zinc finger protein
      (PLZF, zinc finger and BTB domain containing 16 (ZBTB16),
      zinc finger protein 145 (ZNF145)) real-time PCR
      intron spanning forward primer

<400> SEQUENCE: 41
ccacccctac gagtgtgagt                                            20

<210> SEQ ID NO 42
<211> LENGTH: 20
<212> TYPE: DNA
<213> ORGANISM: Artificial Sequence
<220> FEATURE:
<223> OTHER INFORMATION: promyelocytic leukemia zinc finger protein
      (PLZF, zinc finger and BTB domain containing 16 (ZBTB16),
      zinc finger protein 145 (ZNF145)) real-time PCR
      intron spanning reverse primer

<400> SEQUENCE: 42
gcttgatcat ggccgagtag                                            20

```
<210> SEQ ID NO 43
<211> LENGTH: 21
<212> TYPE: DNA
<213> ORGANISM: Artificial Sequence
<220> FEATURE:
<223> OTHER INFORMATION: secreted phosphoprotein 1 (SPP1, osteopontin
      (OPN), bone sialoprotein 1 (BNSP, BSPI), early
      T-lymphocyte activation 1 (ETA-1), urinary stone
      protein) real-time PCR intron spanning forward primer

<400> SEQUENCE: 43
agaagtttcg cagacctgac a                                              21

<210> SEQ ID NO 44
<211> LENGTH: 21
<212> TYPE: DNA
<213> ORGANISM: Artificial Sequence
<220> FEATURE:
<223> OTHER INFORMATION: secreted phosphoprotein 1 (SPP1, osteopontin
      (OPN), bone sialoprotein 1 (BNSP, BSPI), early
      T-lymphocyte activation 1 (ETA-1), urinary stone
      protein) real-time PCR intron spanning reverse primer

<400> SEQUENCE: 44
gtcatccagc tgactcgttt c                                              21

<210> SEQ ID NO 45
<211> LENGTH: 4
<212> TYPE: PRT
<213> ORGANISM: Artificial Sequence
<220> FEATURE:
<223> OTHER INFORMATION: DEAD (Asp-Glu-Ala-Asp) box polypeptide
      conserved motif

<400> SEQUENCE: 45

Asp Glu Ala Asp
1
```

METHODS OF DIAGNOSING ENDOMETRIOSIS

CROSS-REFERENCES TO RELATED APPLICATIONS

This application claims priority to provisional application, U.S. Ser. No. 60/914,018, filed Apr. 25, 2007, the contents of which are herein incorporated by reference in their entirety into this application.

STATEMENT AS TO RIGHTS TO INVENTIONS MADE UNDER FEDERALLY SPONSORED RESEARCH OR DEVELOPMENT

This invention was made in part with Government support under grant HD031398 awarded by the National Institutes of Health. The United States government has certain rights in this invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Endometriosis is a complex disorder associated with pelvic pain and infertility, and is characterized by the implantation of endometrial tissue outside the uterus, primarily on the pelvic peritoneum and ovaries (Giudice L C, Kao L C (2004) The Lancet 364:1789-99). Endometriosis affects 6-10% of women in the general population and 35-50% of women with pain and/or infertility (Eskenazi B, Warner M L (1997) Obstet Gynecol Clin North Am 24:235-58). It is widely accepted that by retrograde menstruation (Sampson J A (1927) Am J Obstet Gynecol 14:442-469), endometrial tissue establishes itself on the peritoneum of women with endometriosis due to heritable and/or acquired defects that confer survival advantage and promote attachment, growth, neoangiogenesis, and invasion into the peritoneum.

The main clinical symptoms of endometriosis are pelvic pain, bleeding and infertility, with the latter proposed to be related to impaired implantation due, in part, to impaired decidualization of endometrial stromal fibroblasts (ESFs). Progesterone and cyclic AMP (cAMP) are important in ESF decidualization and stimulate insulin growth factor binding protein 1 (IGFBP-1) and prolactin (PRL), markers of decidualization. Clinical observations suggest the presence of progesterone ($P_4$) resistance in some women with endometriosis. In addition, endometriotic lesions synthesize aromatase, a key enzyme in the biosynthesis of $E_2$, a potential regulator of lesion growth and pain.

Though the estrogen dependence of endometriosis is well established, the role of progesterone in this disorder is comparatively less well developed. The relative balance of progesterone and estrogen steroidal activity governs the function of normal endometrium throughout the menstrual cycle. The growth promoting effects of estrogen during the proliferative phase of the cycle are countered by progesterone's anti-proliferative actions at the post-ovulatory onset of the secretory phase and decidualizing effects on endometrial stroma later in the secretory phase (Ferenczy A et al. (1979) Am J Obstet Gynecol 133:859-67; Felix J C, Farahmand S (1997) Contraception 55:19-22). A phenotype of attenuated progestereone response is suggested in endometriosis, and interestingly, progestin-based treatment of pain associated with this disorder is variably effective (Winkel C A, Scialli A R (2001) J Womens Health Gend Based Med 10:137-62; Metzger D A et al. (1988) Hum Pathol 19:1417-24).

The dysregulation of various progesterone target genes during the implantation window in women with endometriosis have been reported (Kao L C et al. 2003 Endocrinology 144:2870-81; Kamat A A et al. (2004) Fertil Steril 82:1681-3; Lessey B A et al. (1994) J Clin Endocrinol Metab 79:643-9; Lessey B A et al (1992) J Clin Invest 90:188-95; Cullinan E B et al. (1996) Proc Natl Acad Sci 93:3115-20; Taylor H S et al. (1999) Hum Reprod 14:1328-31). An endometrial microenvironment characterized by attenuated progesterone response may be inhospitable to embryonic implantation. Reduced responsiveness, or resistance, to progesterone in eutopic endometrium has been implicated in the pathophysiology of this enigmatic condition, as suggested by the altered pattern of matrix metalloproteinase (MMP) gene expression in the secretory phase (Osteen K G et al. (2005) Fertil Steril 83:529-37). Interestingly, in vitro treatment of endometrial tissues acquired from women with endometriosis with progesterone fails to fully suppress either pro-MMP-3 or pro-MMP-7 secretion and fails to prevent the ability of these tissues to establish experimental disease in mice (Bruner-Tran K L et al. (2002) J Clin Endocrinol Metab 87:4782-91). More recently, endometrial cell culture and nude mouse models were used to demonstrate that progesterone insensitivity was intrinsic to the eutopic endometrium of women with endometriosis and could be corrected by treatment with the synthetic progestin, tanaproget (Bruner-Tran K L et al (2006) J Clin Endocrinol Metab 91:1554-60).

Progesterone resistance may occur at the level of the progesterone receptor isoforms (PR-A and PR-B) (Igarashi T M et al. (2005) Fertil Steril 84:67-74; Attia G R et al. (2000) J Clin Endocrinol Metab 85:2897-902), steroid receptor co-activators, or down-stream effectors (TGFβ, DKK-1, Retinoic acid, c-myc, etc). In endometriotic lesions, a decrease in the expression of the progesterone target gene, 17-beta hydroxysteroid dehydrogenase type I, is evidence of progesterone resistance in ectopic endometrium (Vierikko P et al. (1985) Fertil Steril 43:218-24, Bulun S E et al. (2006) Mol Cell Endocrinol 248:94-103).

There is a need in the art for the identification of molecular differences in the endometrium of women with endometriosis in order to better understand the pathogenesis of this condition and to facilitate development of novel strategies for the treatment of associated infertility and pain. The present invention fulfills this need by identifying biomarkers and kits useful in the diagnosis and prognosis of endometriosis and infertility in women with endometriosis, presenting methods for identifying compounds for treating or preventing endometriosis and infertility caused by endometriosis, and by presenting therapeutics useful in the treatment or prevention of endometriosis and infertility caused by endometriosis, among other embodiments.

BRIEF SUMMARY OF THE INVENTION

Generally, the methods of this invention find use in diagnosing or for providing a prognosis for endometriosis by detecting the expression levels of biomarkers, which are differentially expressed (up- or down-regulated) in endometrial cells from a patient with endometriosis. These markers can be used to distinguish the stage or severity of endometriosis. These markers can also be used to provide a prognosis for the course of treatment in a patient with endometriosis. Similarly, these markers can be used to diagnose infertility in a patient with endometriosis or to provide a prognosis for a fertility trial in a patient suffering from endometriosis. The biomarkers of the present invention can be used alone or in combination for the diagnosis or prognosis of endometriosis.

In one embodiment, the methods of the present invention find use in assigning treatment to a patient suffering from endometriosis. By detecting the expression levels of biomarkers found herein, the appropriate treatment can be assigned to a patient suffering from endometriosis. These treatments can include, but are not limited to, hormone therapy, chemotherapy, immunotherapy, and surgical treatment. Similarly, the methods of the current invention can be used to assign treatment to a patient with reduced fertility due to endometriosis. In this fashion, by determining the degree to which the patient's fertility has been reduced, through the detection of biomarkers found herein, the appropriate treatment can be assigned. Relevant treatments include, but are not limited to, hormone therapy, chemotherapy, immunotherapy, and surgical treatment.

Diagnostic and prognostic kits comprising one or more markers for use are provided herein. Also provided by the invention are methods for identifying compounds that are able to prevent or treat endometriosis or reduced fertility caused by endometriosis by modulating the expression level or activity of markers found in any one of the identified gene subsets. Finally, therapeutic methods are provided, wherein endometriosis or reduced fertility caused by endometriosis is treated using antibody, siRNA, microRNA, or antisense molecules that specifically bind to one or more of the markers found in any one of the identified gene subsets.

BRIEF DESCRIPTION OF THE DRAWINGS

FIG. 3. Expression of selected genes per cycle phase in the endometrium of women with endometriosis relative to women without endometriosis using real time PCR. A, Proliferative phase. B, Early secretory phase. C, Mid secretory phase. Each phase represents comparison of RNA samples from 3 women with endometriosis and 3 women without disease. Fold-change values are displayed above each gene and are plotted on the y-axis on a log 10 scale. Bars represent SEM. * $p<0.05$, ** $p<0.01$.

FIG. 4. Differential expression of genes involved in the regulation of the mitotic cell cycle in ESE from women with versus without endometriosis. In this diagram, each box represents a particular gene. Up-regulated genes with fold change are represented in green while down-regulated genes and fold change are represented in red. Diagram adapted from KEGG at http://www.genome.jp.kegg.

FIG. 5B. Gene expression in ESFs treated with 0.5 mM cAMP for 96 hours.

FIG. 5D. Steroidogenic gene expression in severe endometriosis MSE biopsies compared to non-endometriotic MSE samples.

FIG. 5F. Steroidogenic gene expression in ESFs treated with E2/P4 for 14 days.

FIG. 18. Levels of SST and DKK mRNA after transfection with control and anti-Hic-5 siRNA.

FIG. 19. Levels of DKK1 mRNA in non-endometriotic endometrial stromal cells transfected with siHic-5.

DETAILED DESCRIPTION OF THE INVENTION

Figure 1:
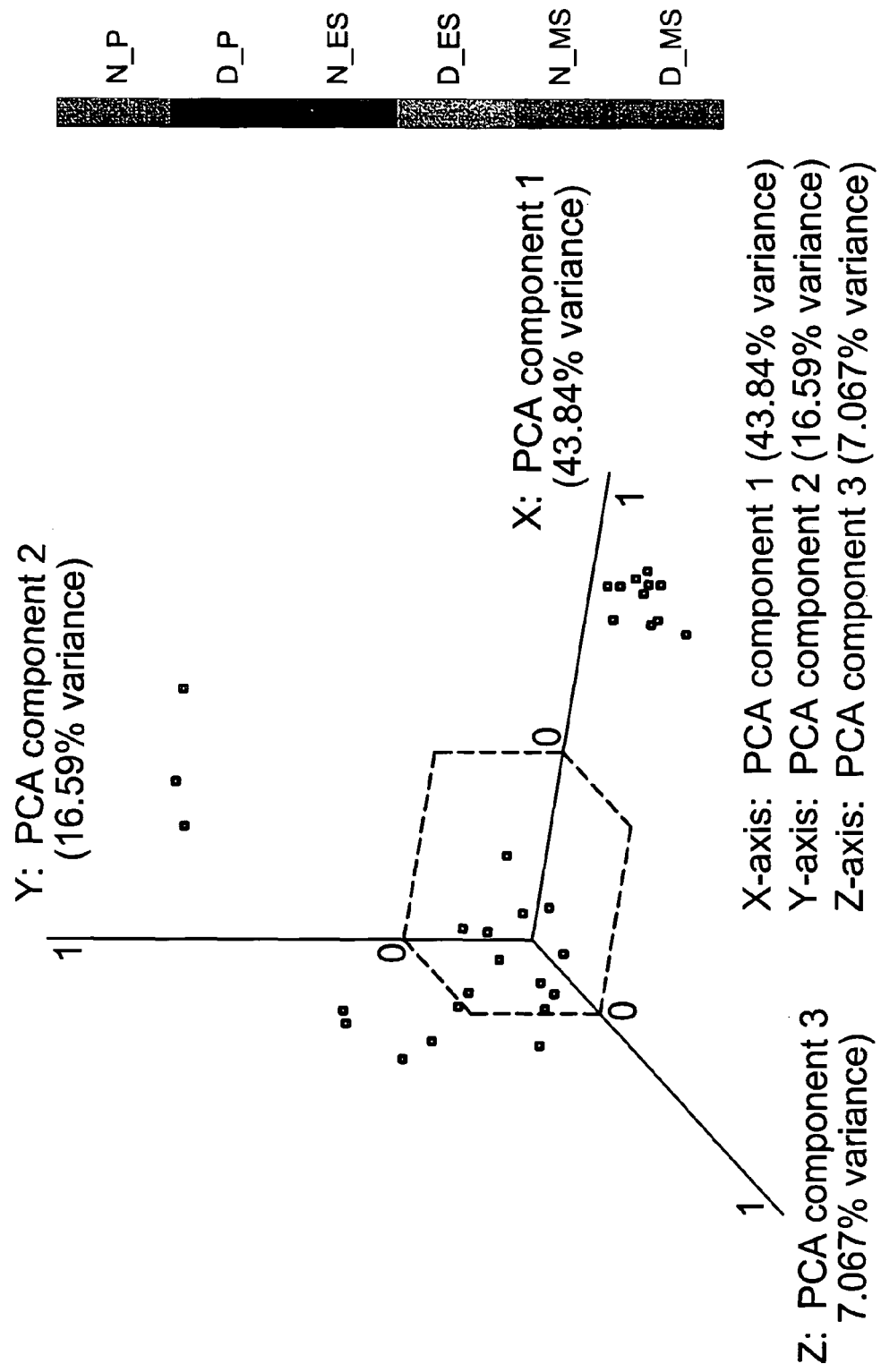
FIG. 1. PCA of endometrium from subjects with moderate/severe endometriosis (D) and from subjects without disease (N) in the P, ES, and MS phases. Each plotted point represents an individual sample's expression profile distributed into a three-dimensional space based on the variance in gene expression. The labeled axes represent three PCA components and the percentage is the amount of gene expression variation (in the entire dataset) explained by each component.

The identification of molecular differences in the endometrium of women with endometriosis is an important step toward understanding the pathogenesis of this condition and toward developing novel strategies for the treatment of associated infertility and pain. In the present invention, a global gene expression analysis of endometrium from women with and without moderate/severe stage endometriosis was conducted. These results compared the gene expression signatures across various phases of the menstrual cycle. Transciptome analysis revealed molecular dysregulation of the proliferative-to-secretory transition in endometrium of women with endometriosis. Paralleled gene expression analysis of endometrial specimens obtained during the early secretory phase demonstrated a signature of enhanced cellular survival and persistent expression of genes involved in DNA synthesis and cellular mitosis in the setting of endometriosis. Comparative gene expression analysis of progesterone-regulated genes in secretory phase endometrium confirmed the observation of attenuated progesterone response. Additionally, susceptibility genes were identified that are associated with this disorder and can be used as biomarkers for diagnostic assays and drug discovery assays, including FOXO1A, MIG6, and CYP26A1. Other biomarkers identified in the present invention include those found in Tables 4-6 and 8-9, Hic-5, IL-8, and those found in examples 1-4.

In one embodiment, the current invention provides a method of diagnosing or providing a prognosis for endometriosis, the method comprising the step of detecting in a biological sample altered expression (over or under expression) of an endometriosis biomarker gene or protein in a subject suspected of or having endometriosis. In one embodiment, the gene or protein detected is selected from the group consisting of those found in Tables 4-6. In another embodiment, the gene or protein detected is selected from the group consisting of those found in Tables 8 and 9. In yet another embodiment, the gene or protein detected is Hic-5, IL-8, or any other endometriosis biomarker shown to have altered expression in tissues from women having endometriosis in examples 1-4.

In one embodiment of the present invention, the sample used is a biopsy from a mammal. In a particular embodiment, the sample is an endometrial biopsy. In other particular embodiments, the mammal is a mouse, rabbit, horse, dog, or human. Those of skill in the art will know of other samples well suited for use in the present invention.

In a second embodiment, the current invention provides a method of diagnosing or providing a prognosis for reduced fertility, the method comprising the step of detecting in a biological sample altered expression (over or under expression) of an endometriosis biomarker gene or protein in a subject suspected of or having endometriosis. In one embodiment, the gene or protein detected is selected from the group consisting of those found in Tables 4-6. In another embodiment, the gene or protein detected is selected from the group consisting of those found in Tables 8 and 9. In another embodiment, the gene or protein detected is Hic-5, IL-8, or any other endometriosis biomarker shown to have altered expression in tissues from women having endometriosis in examples 1-4.

The present invention also provides methods of identifying a compound for treating or preventing endometriosis or reduced fertility caused by endometriosis. In one embodiment, the method comprises the steps of: contacting a compound with a protein known to be differentially expressed in endometriosis and detecting altered expression as compared to a control, thereby identifying a compound. In a particular embodiment, the protein contacted is selected from the group consisting of those found in Tables 4-6. In another embodiment, the protein contacted is Hic-5, IL-8, any protein listed in Tables 8 and 9, or any other protein shown to be differentially regulated in examples 1-4. In certain embodiments, the compound is a small molecule, polynucleotide, or peptide. In other embodiments, the assay is performed in vivo, in a cell, or in a tissue sample. In yet other embodiments, the assay is a biochemical assay performed iv vitro. Assays particularly well suited for use in the present invention are well known in the art.

The present invention also provides kits for diagnosing endometriosis or reduced fertility caused by endometriosis, comprising a probe for one or more nucleic acid or protein biomarkers known to be differentially expressed in endometriosis. In one embodiment, the biomarkers are selected from the group consisting of those in Tables 4-6. In other embodiments, the markers are further selected from HIC-5, IL-8, proteins listed in Tables 8 and 9, and other biomarkers shown to be differentially expressed herein. In one particular embodiment, the kit comprises reagents for quantitative amplification of the selected biomarkers. Alternatively, the kit may comprise a microarray. In another particular embodiment, the kit comprises a cocktail of antibodies. In some embodiments the kit comprises 2 or more probes. In other embodiments, the kits may contain 3, 4, 5, 6, 7, 8, 9, 10, 15, 20, 25, 30, 40, 50, 75, 100, 200, 500 or more probes.

The present invention provides therapeutic molecules for the treatment or prevention of endometriosis or reduced fertility caused by endometriosis. In one embodiment, the therapeutic molecules comprise antibodies or immunogenic fragments of antibodies. In other embodiments, the molecules comprise antisense oligonucleotides, siRNAs, microRNAs, or other nucleic acids or nucleic acid analogues well known in the art. In particular embodiments, the therapeutic molecules specifically hybridize or immunogenically bind to a biomarker selected from the group consisting of those listed in Tables 4-6, those listed in Tables 8 and 9, Hic-5, IL-8, and any other marker shown herein to be differentially expressed in endometriosis. In other embodiments, the biomarkers are progesterone-related genes.

Treatments for endometriosis are well known in the art. These treatments include, but are not limited to, pain killers, hormonal treatments, chemotherapy, and surgical treatments. Pain killers used for the treatment of endometriosis include both simple analgesics, such as paracetamol, COX-2 inhibitors, aspirin, and other non-steroidal anti-inflammatory drugs well known in the art, and narcotic analgesics, such as morphine, codine, oxycodone, and others well known in the art. Hormonal treatments include, but are not limited to, oral contraceptives, progestins, such as Dydrogesterone, Medroxyprogesterone acetate, Depot medroxyprogesterone acetate, Norethisterone, Levonorgestrel, and others well known in the art, progesterone and progesterone-like substances, GnRH agonists, such as leuprorelin, buserelin, goserelin, histrelin, deslorelin, nafarelin, and triptorelin, androgens and synthetic androgens like Danazol, and aromatase inhibitors. Surgical treatments include, but are not limited to, laparoscopic surgery, hysterectomy, and oophorectomy. Other treatments particularly well suited for use in the present invention are well known in the art.

The present invention includes other biomarkers known to be differentially expressed in endometriosis, such as those disclosed in Burney et al. (Burney et al., *Endocrinology* 148 (8):3814-3826 (2007)) the complete contents of which are herein incorporated by reference.

DEFINITIONS

The term "marker" refers to a molecule (typically protein, nucleic acid, carbohydrate, or lipid) that is expressed in an endometrial cell from a women with endometriosis, expressed on the surface of an endometrial cell from a woman with endometriosis, or secreted by an endometrial cell from a woman with endometriosis in comparison to a cell from a woman who does not have endometriosis, and which is useful for the diagnosis of endometriosis, for providing a prognosis, for predicting the fertility of an individual with endometriosis, and for preferential targeting of a pharmacological agent to the endometrial cell. Oftentimes, such markers are molecules that are overexpressed in an endometrial cell from a woman with endometriosis in comparison to a cell from a woman without endometriosis, for instance, 1-fold overexpression, 2-fold overexpression, 3-, 4-, 5-, 6-, 7-, 8-, 9-, or 10-fold overexpression or more fold-overexpression in comparison to a cell from a woman without endometriosis. Further, a marker can be a molecule that is inappropriately synthesized in the endometrial cell of a woman with endometriosis, for instance, a molecule that contains deletions, additions, or mutations in comparison to the molecule expressed in a cell from a woman without endometriosis. Alternatively, such biomarkers are molecules that are underexpressed in an endometrial cell from a woman with endometriosis in comparison to a cell from a woman without endometriosis, for instance, 1-fold underexpression, 2-fold underexpression, 3-, 4-, 5-, 6-, 7-, 8-, 9-, or 10-fold underexpression, or more fold-overexpression in comparison to a cell from a woman without endometriosis. Further, a marker can be a molecule that is inappropriately synthesized in a cell from a woman with endometriosis, for instance, a molecule that contains deletions, additions or mutations in comparison to the molecule expressed in a cell from a woman without endometriosis.

It will be understood by the skilled artisan that markers may be used in combination with other markers or tests for any of the uses, e.g., prediction, diagnosis, or prognosis of fertility or endometriosis, disclosed herein.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum, endometrial tissue, the uterine fundus, thyroid tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., endometrial, etc.), the size and type of the tissue, among other factors. Representative biopsy techniques include, but are not limited to, excisional biopsy, incisional biopsy, needle biopsy, surgical biopsy, and bone marrow biopsy. An "excisional biopsy" refers to the removal of an entire endometrial tissue mass with a small margin of non-endometrial tissue surrounding it. An "incisional biopsy" refers to the removal of a wedge of endometrial tissue. Biopsy techniques are discussed, for example, in *Harrison's Principles of Internal Medicine*, Kasper, et al., eds., 16th ed., 2005, Chapter 70, and throughout Part V.

The terms "overexpress", "overexpression", "overexpressed", or "up-regulated" interchangeably refer to a protein or nucleic acid (RNA) that is transcribed or translated at a detectably greater level, usually in an endometrial cell from a woman with endometriosis, in comparison to a cell from a woman without endometriosis. The term includes overexpression due to transcription, post transcriptional processing, translation, post-translational processing, cellular localization (e.g., organelle, cytoplasm, nucleus, cell surface), and RNA and protein stability, as compared to a cell from a woman without endometriosis. Overexpression can be detected using conventional techniques for detecting mRNA (i.e., Q-PCR, RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a cell from a woman without endometriosis. In certain instances, overexpression is 1-, 2-, 3-, 4-, 5-, 6-, 7-, 8-, 9-, 10-fold, or more higher levels of transcription or translation in comparison to a cell from a woman without endometriosis.

The terms "underexpress", "underexpression", "underexpressed", or "down-regulated" interchangeably refer to a protein or nucleic acid that is transcribed or translated at a detectably lower level in a endometrial cell from a woman with endometriosis, in comparison to a cell from a woman without endometriosis. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., Q-PCR, RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-, 2-, 3-, 4-, 5-, 6-, 7-, 8-, 9-, 10-fold or more lower levels of transcription or translation in comparison to a control.

The term "differentially expressed", "differentially regulated", or "altered expression" refers generally to a protein or nucleic acid that is overexpressed (upregulated) or underexpressed (downregulated) in one sample compared to at least one other sample, generally in a patient with endometriosis, in comparison to a patient without endometriosis, in the context of the present invention.

"Therapeutic treatment" refers to chemotherapy, hormonal therapy, radiotherapy, immunotherapy, and biologic (targeted) therapy.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. The biomarkers described herein can be detected with probes that have, e.g., more than 70% identity over a specified region, or for example, more than 80%, 85%, 90%, 95%, 96%, 97%, 98%, or 99% identity to the reference sequence provided by the accession number, up to 100% identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The nucleic acids of the differentially expressed genes of this invention or their encoded polypeptides refer to all forms of nucleic acids (e.g., gene, pre-mRNA, mRNA) or proteins, their polymorphic variants, alleles, mutants, and interspecies homologs that (as applicable to nucleic acid or protein): (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 20, 25, 30, 35, 40, 45, 50, 75, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 20, 25, 30, 35, 40, 45, 50, 75, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "functional effects" in the context of assays for testing compounds that modulate a marker protein includes the determination of a parameter that is indirectly or directly under the influence of a biomarker of the invention, e.g., a chemical or phenotypic. A functional effect therefore includes ligand binding activity, transcriptional activation or repression, the ability of cells to proliferate, the ability to migrate, among others. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers. The functional effects can be evaluated by many means known to those skilled in the art, e.g., microscopy for quantitative or qualitative measures of alterations in morphological features, measurement of changes in RNA or protein levels for other genes expressed in placental tissue, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Inhibitors," "activators," and "modulators" of the markers are used to refer to activating, inhibitory, or modulating molecules identified using in vitro and in vivo assays of endometriosis biomarkers. Inhibitors are compounds that, e.g., bind to, partially or totally block activity, decrease, prevent, delay activation, inactivate, desensitize, or down regulate the activity or expression of endometriosis biomarkers. "Activators" are compounds that increase, open, activate, facilitate, enhance activation, sensitize, agonize, or up regulate activity of endometriosis biomarkers, e.g., agonists. Inhibitors, activators, or modulators also include genetically modified versions of endometriosis biomarkers, e.g., versions with altered activity, as well as naturally occurring and synthetic ligands, antagonists, agonists, antibodies, peptides, cyclic peptides, nucleic acids, antisense molecules, ribozymes, RNAi, microRNA, and siRNA molecules, small organic molecules and the like. Such assays for inhibitors and activators include, e.g., expressing endometriosis biomarkers in vitro, in cells, or cell extracts, applying putative modulator compounds, and then determining the functional effects on activity, as described above.

Samples or assays comprising endometriosis biomarkers that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of endometriosis biomarkers is achieved when the activity value relative to the control is about 80%, preferably 50%, more preferably 25-0%. Activation of endometriosis biomarkers is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate endometriosis biomarkers. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Predictive, Diagnostic, and Prognostic Methods

The present invention provides methods of predicting, diagnosing, or providing prognosis of endometriosis or fertility in a patient with endometriosis by detecting the expression of markers differentially expressed in cells from a patient with endometriosis. Prediction and diagnosis involve determining the level of a panel of endometriosis biomarker polynucleotides or the corresponding polypeptides in a patient or patient sample and then comparing the level to a baseline or range. Typically, the baseline value is representative of levels of the polynucleotide or nucleic acid in a healthy person not suffering from, or destined to develop, endometriosis, as measured using a biological sample such as an endometrial biopsy or a sample of a bodily fluid. Variation of levels of a polynucleotide or corresponding polypeptides of the invention from the baseline range (either up or down) indicates that the patient has an increased risk of developing endometriosis, an increased risk of the recurrence of endometriosis or endometriotic lesions, or an increased risk of infertility. Markers useful in these predictions, diagnoses, and prognoses include, but are not limited to those found in Tables 4-6, and 8-11.

As used herein, the term "diagnosis" refers to distinguishing between having and not having endometriosis. As used herein, the term "providing a prognosis" may refer to providing a prediction of the probable course and outcome of endometriosis or for a prediction of the probable outcome of a treatment course for endometriosis, or alternatively for providing a prediction of the probable outcome of a fertility trial in a patient with endometriosis.

Antibody reagents can be used in assays to detect expression levels of the biomarkers of the invention in patient samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., Curr. Opin. Biotechnol., 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., Electrophoresis, 18:2184-93 (1997); Bao, J. Chromatogr. B. Biomed. Sci., 699:463-80 (1997). Liposome immunoassays, such as flow-injection liposome immunoassays and liposome immunosensors, are also suitable for use in the present invention. See, e.g., Rongen et al., J. Immunol. Methods, 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.*, 27:261-276 (1989)).

Specific immunological binding of the antibody to nucleic acids can be detected directly or indirectly. Direct labels include fluorescent or luminescent tags, metals, dyes, radionuclides, and the like, attached to the antibody. An antibody labeled with iodine-125 ($^{125}I$) can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}I$; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Alternatively, nucleic acid binding molecules such as probes, oligonucleotides, oligonucleotide arrays, and primers can be used in assays to detect differential RNA expression in patient samples, e.g., RT-PCR. In one embodiment, RT-PCR is used according to standard methods known in the art. In another embodiment, PCR assays such as Taqman® assays available from, e.g., Applied Biosystems, can be used to detect nucleic acids and variants thereof. In other embodiments, qPCR and nucleic acid microarrays can be used to detect nucleic acids. Reagents that bind to selected biomarkers can be prepared according to methods known to those of skill in the art or purchased commercially.

Analysis of nucleic acids can be achieved using routine techniques such as Southern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression From Experiments to Data Analysis and Modeling," Cambridge University Press, 2002.

Analysis of nucleic acid markers and their variants can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. (Chee et al., *Science*, 274:610-614 (1996); Drmanac et al., *Science*, 260:1649-1652 (1993); Drmanac et al., *Nat. Biotechnol.*, 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Useful physical formats comprise surfaces having a plurality of discrete, addressable locations for the detection of a plurality of different markers. Such formats include microarrays and certain capillary devices. See, e.g., Ng et al., *J. Cell Mol. Med.*, 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

In another format, the various markers of the invention also provide reagents for in vivo imaging such as, for instance, the imaging of labeled regents that detect the nucleic acids or encoded proteins of the biomarkers of the invention. For in vivo imaging purposes, reagents that detect the presence of proteins encoded by endometriosis biomarkers, such as antibodies, may be labeled using an appropriate marker, such as a fluorescent marker.

Compositions, Kits and Integrated Systems

The invention provides compositions, kits and integrated systems for practicing the assays described herein using antibodies specific for the polypeptides or nucleic acids specific for the polynucleotides of the invention.

Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies that recognize at least two marker proteins listed in Tables 4-6 and 8-11. In other embodiments, these cocktails may include antibodies that recognize at least 3, 4, 5, 6, 7, 8, 9, 10, 15, 20, 25, 30, 40, 50, 100, or more of the marker genes listed in Tables 4-6 and 8-11.

Methods to Identify Compounds

A variety of methods may be used to identify compounds that prevent or treat endometriosis or infertility caused by endometriosis. Typically, an assay that provides a readily measured parameter is adapted to be performed in the wells of multi-well plates in order to facilitate the screening of members of a library of test compounds as described herein. Thus, in one embodiment, an appropriate number of cells can be plated into the cells of a multi-well plate, and the effect of a test compound on the expression of a biomarker can be determined.

The compounds to be tested can be any small chemical compound, or a macromolecule, such as a protein, sugar, nucleic acid or lipid. Typically, test compounds will be small chemical molecules and peptides. Essentially any chemical compound can be used as a test compound in this aspect of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one embodiment, high throughput screening methods are used which involve providing a combinatorial chemical or peptide library containing a large number of potential therapeutic compounds. Such "combinatorial chemical libraries" or "ligand libraries" are then screened in one or more assays, as described herein, to identify those library members (particular chemical species or subclasses) that display a desired characteristic activity. In this instance, such compounds are screened for their ability to reduce or increase the expression of the biomarkers of the invention.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487-493 (1991) and Houghton et al., *Nature*, 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS USA*, 90:6909-6913 (1993)), vinylogous polypeptides (Hagihara et al., *J. Amer. Chem. Soc.*, 114:6568 (1992)), nonpeptidal peptidomimetics with glucose scaffolding (Hirschmann et al., *J. Amer. Chem. Soc.*, 114:9217-9218 (1992)), analogous organic syntheses of small compound libraries (Chen et al., *J. Amer. Chem. Soc.*, 116:2661 (1994)), oligocarbamates (Cho et al., *Science*, 261:1303 (1993)), and/or peptidyl phosphonates (Campbell et al., *J. Org. Chem.*, 59:658 (1994)), nucleic acid libraries (see Ausubel, Berger and Sambrook, all supra), peptide nucleic acid libraries (see, e.g., U.S. Pat. No. 5,539, 083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.)

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds is possible using the integrated systems of the invention.

Methods to Inhibit Marker Protein Expression Using Nucleic Acids

A variety of nucleic acids, such as antisense nucleic acids, siRNAs, microRNAs, or ribozymes, may be used to inhibit the function of the markers of this invention. Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA, microRNAs, or ribozyme oligonucleotides, phosphorothioate oligonucleotides can be used. Modifications of the phosphodiester linkage as well as of the heterocycle or the sugar may provide an increase in efficiency. Phosphorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

"RNAi molecule" or an "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibodies to cell surface markers for the target cells.

For transfection, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., *Curr Drug Delivery* (2006) 3:147-5 and Patil, et al., *AAPS Journal* (2005) 7:E61-E77, each of which are incorporated herein by reference. Delivery of siRNA molecules is also described in several U.S. patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, *Bioconjugate Chem.*, 10, 1068-1074; Wang et al., International PCT publication Nos. WO 03/47518 and WO 03/46185), poly(lactic-co-glycolic) acid (PLGA) and PLCA microspheres (see for example U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of use with this invention include, for example: CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[I-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, antisense, siRNA, microRNAs, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

In some embodiments, antisense, siRNA, microRNAs, or ribozyme sequences are delivered into cells via a viral expression vector. Viral vectors suitable for delivering such molecules to cells include adenoviral vectors, adeno-associated vectors, and retroviral vectors (including lentiviral vectors). For example, viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

EXAMPLES

Example 1

In this example, paralleled gene expression analysis was applied to investigate cycle phase-dependent differences in the eutopic endometrial gene expression signatures across the menstrual cycle of women with moderate/severe disease, compared to women without endometriosis. In women with moderate/severe disease, the gene expression profile suggested incomplete transitioning of the endometrium from the proliferative to early secretory phase, a phenotype of enhanced cellular survival, and attenuation of progesterone-induced down-regulation of DNA synthesis and cellular mitosis. Additionally, the secretory endometrium from women with disease demonstrated dysregulation of numerous genes known to be progesterone regulated. These results provide compelling molecular evidence for attenuated progesterone responsiveness within eutopic endometrium in women with endometriosis.

Endometriosis is a visually heterogeneous condition and studies have documented inaccuracy in its visual diagnosis, particularly in cases of minimal/mild stages (Marchino G L et al. (2005) *Fertil Steril* 84:12-5; Walter A J et al. (2001) *Am J Obstet Gynecol* 184:1407-11; discussion 1411-3). The present study avoided these problems by including only women with surgically documented and histologically validated moderate/severe stage endometriosis. Accordingly, endometrial biopsies were obtained from normally cycling women with histologically confirmed, moderate-severe endometriosis at laparoscopy (n=21) and from normally cycling women found to be free of endometriosis at surgery (n=16). Moderate to severe endometriosis (Stage III-IV disease) was defined in accordance with the Revised American Fertility Society (rAFS) classification system (The American Fertility Society (1985) *Fertil Steril* 43:351-2). Study subjects in the severe endometriosis cohort were 22-44 years old, had regular menstrual cycles, and were documented not to be pregnant at the time of surgery. Many of these patients were also infertile and several had failed in vitro fertilization treatment(s) prior to laparoscopic surgery (Littman E et al. (2005) *Fertil Steril* 84:1574-8). The demographic profile of the endometriosis-free cohort has been described previously (Talbi S et al. (2006) *Endocrinology* 147:1097-121). The demographic profile of the cohort with endometriosis is provided in Table 1. Subjects using any form of hormonal treatment within 3 months of biopsy were excluded from the study. Biopsy specimens were obtained using either Pipelle catheters or curette from the uterine fundus under sterile conditions. In comparable subjects without endometriosis, we have reported minimal variation between these sampling methods when comparing endometrial molecular profiles (Talbi S et al. (2006) *Endocrinology* 147:1097-121). Samples were processed for histologic confirmation as well as for RNA isolation. Endometrium was dated by up to four independent histopathologists, all of whom were blinded to the subject's identity and timing of the biopsy. Histologic dating was based upon the method of Noyes et al (Noyes R W et al. (1975) *Am J Obstet Gynecol* 122:262-3). Specimens were classified as proliferative (PE, days 8-14), early secretory (ESE, days 15-18), mid-secretory (MSE, days 19-23) or late secretory (LSE, days 24-28) endometrium.

TABLE 1

Subject characteristics - moderate/severe endometriosis cohort (n = 21)

| Patient ID | Cycle phase | Age (yr) | Distribution | Diagnoses | Ethnicity | Medications |
|---|---|---|---|---|---|---|
| 26A | Pro | 31 | O, PI | | Caucasian | |
| 587 | Pro | 37 | PI | Liver endo | Caucasian | |
| 647 | Pro | 39 | R, O, PI | Leiomyoma | Caucasian | |
| 594 | Pro | 38 | O, PI | | Caucasian | Amour thyroid |
| 651 | Pro | 37 | O, PI | Leiomyoma | Caucasian | Advair, rhinocort |
| 508 | Pro | 25 | R, O, PI | | Caucasian | Atenolol |
| 489 | ES | 39 | R, PI | Leiomyoma | Asian | Levothyroxine |
| 496 | ES | 37 | O, PI | Leiomyoma | Caucasian | Advair, rhinocort |
| 599 | ES | 35 | R, O, PI | | Black | |
| 27A | ES | 22 | R, O, PI | | Caucasian | |
| 517 | ES | 35 | R, PI | Leiomyoma | Asian | Trental, ciprofloxacin |
| 575 | ES | 26 | O, PI | | Unknown | |
| 33A | MS | 27 | R, PI | | Caucasian | |
| 7A/97A | MS | 35 | O, PI | | Unknown | |
| 73A | MS | 26 | O, PI | | Caucasian | |
| 516 | MS | 34 | R, PI | Leiomyoma | Asian | |
| 540 | MS | 37 | R, PI | | Caucasian | Keflex prn |
| 543 | MS | 38 | R, O, PI | | Caucasian | |
| 678 | MS | 44 | R, PI | Leiomyoma | Asian | |

TABLE 1-continued

Subject characteristics - moderate/severe endometriosis cohort (n = 21)

| Patient ID | Cycle phase | Age (yr) | Distribution | Diagnoses | Ethnicity | Medications |
|---|---|---|---|---|---|---|
| 72A | MS | 31 | PI | | Caucasian | |
| 645 | MS | 39 | R, PI | | Asian Indian | |

Under the Cycle phase, Pro = proliferative; ES = early secretory; MS = mid secretory. Under the Distribution of disease, PI = peritoneal endometriosis, defined as biopsy proven serosal implant; O = ovarian endometriosis, defined as biopsy proven endometrioma; R = rectovaginal endometriosis, defined as posterior cul de sac obliteration due to endometriotic lesions. All endometrial specimens were taken from subjects surgically staged with moderate/severe endometriosis in accordance with rAFS criteria (23).

RNA Preparation/Target Preparation/Array Hybridization and Scanning

A total of 37 specimens were used for microarray analysis, with 21 specimens (PE=6, ESE=6, MSE=9) obtained from subjects surgically confirmed to be affected by moderate-severe endometriosis and 16 specimens (PE=5, ESE=3, MSE=8) obtained from subjects surgically confirmed to be free of endometriosis. The latter samples were used previously to define the normal endometrial expression signature across the various phases of the menstrual cycle (Talbi S et al. (2006) Endocrinology 147:1097-121). Each endometrial biopsy specimen was processed individually for microarray hybridization. Briefly, total RNA was extracted from each whole tissue specimen using Trizol Reagent (Invitrogen, Carlsbad, Calif.), subjected to DNase treatment and purified using the RNeasy Kit (Qiagen, Valencia, Calif.). RNA quality was confirmed by A260/A280 ratio and agarose gel electrophoresis, where resolution of distinct 28s and 18s rRNA bands was used to suppose intact RNA. Using 5 μg of template, double stranded cDNA and biotinylated cRNA were prepared by methods previously described (Talbi S et al. (2006) Endocrinology 147:1097-121). After chemical fragmentation with 5× fragmentation buffer (200 mM Tris, pH 8.1; 500 mM KOAc; 150 mM MgOAc), biotinylated cRNAs were hybridized to Affymetrix HU133 Plus 2.0 version high density oligonucleotide arrays (Affymetrix, Santa Clara, Calif.) on an Affymetrix fluidics station at the Stanford University School of Medicine Protein and Nucleic Acid (PAN) Facility. Fluorescent labeling of samples and laser confocal scanning of the arrays were conducted at the PAN facility.

Microarray Gene Expression Data Analysis

The data generated by the Affymetrix GeneChip Operating Software analysis of the scanned array images were imported into GeneSpring version 7.2 (Agilent Technologies Inc., Santa Clara, Calif.) for analysis. The data files containing the probe level intensities were processed using the Robust Microarray Analysis (RMA) algorithm (GeneSpring) for background adjustment, normalization and log 2-transformation of perfect match values (Kamat A A et al. (2004) Fertil Steril 82:1681-3). Per-chip and per-gene normalization was conducted using GeneSpring normalization algorithms. The normalized data were used in pairwise comparisons of cycle phase-specific endometrium from subjects with and without moderate-severe endometriosis. The resulting gene lists from each pairwise comparison included only the genes that evidenced a fold change of 1.5 or higher and a p-value less than 0.05 by a one-way ANOVA parametric test and a Benjamini-Hochberg multiple testing correction for false discovery rate, as described (Talbi S et al (2006) Endocrinology 147:1097-121). To identify samples with similar patterns of gene expression, principal component analysis (PCA) was performed in which a multi-dimensional dataset is displayed in reduced dimensionality, with each dimension representing a component to which a certain percentage of variance in the data is attributed. The PCA algorithm in GeneSpring was applied to all endometrial specimens grouped by disease status and cycle phase using all 54,600 genes and ESTs on the HG U133 Plus 2.0 chip to evaluate for similar gene expression patterns and underlying cluster structures, as described (Talbi S et al. (2006) Endocrinology 147:1097-121). To further evaluate for patterns in the gene expression profiles, hierarchical clustering analysis of the combined (pairwise comparisons-derived) gene list and all samples was conducted using the smooth correlation for distance measure algorithm (GeneSpring). A Heatmap was generated which graphically depicts the measured intensity values of the genes and the dendrogram illustrates relationships between the specimens (Talbi S et al. (2006) Endocrinology 147:1097-121). Raw data files of this experiment are stored at the NCBI Gene Expression Omnibus (GEO) database under the identifier GSE6364.

Gene Ontology Classification of Differentially Expressed Genes.

The integration of gene expression data with the gene ontology was carried out using the GO Tree Machine (GOTM) (Ashburner M et al. (2000) Nat Genet 25:25-9). GOTM builds significant biological processes, molecular functions, and cellular components in a gene list as previously described (Osteen K G et al. (2005) Fertil Steril 83:529-37).

Validation of Microarray Data by Real-Time PCR.

Genes of different expression fold changes in each menstrual cycle phase were selected for validation by real time PCR as described previously (Talbi S et al. (2006) Endocrinology 147:1097-121). Real time PCR was performed on a minimum of N=3 samples in both the normal and disease conditions for the proliferative, early-secretory, and mid-secretory phases. First strand cDNA was generated from 1 μg of total RNA using the Omniscript RT Kit (Qiagen, Valencia, Calif.). PCR reactions were performed in triplicate in 25 μL using the Brilliant SYBR Green PCR kit according to the manufacturer's (Stratagene) specifications. Ribosomal protein L19 (RPL19) was chosen for use as a normalizer due to the low variation in expression levels evidenced by this gene in the microarray dataset. Intron spanning PCR primers were designed for each gene of interest (Table 2). Data analysis of the real-time PCR data was conducted as described previously (Talbi S et al. (2006) Endocrinology 147:1097-121). We considered the normal endometrial specimens as "control" samples, and the endometrial specimens from subjects with severe endometriosis as our "test" samples when conducting fold change calculations from the raw Ct values. Statistical analysis of the PCR data was conducted using the relative expression software tool (REST) algorithm, which employs a pairwise fixed reallocation and randomization test to determine significance (Pfaffl MW et al. (2002) Nucleic Acids Res 30:e36).

TABLE 2

Primer sequences used in real-time PCR reactions.

| Gene | Forward primer (5'-3') | Reverse primer (5'-3') | Unigene ID | Expected Product Length |
|---|---|---|---|---|
| S100A8 | CAGCTGTCTTTCAGAAGAGGTG SEQ ID NO: 1 | TGAGGACACTCGGTCTCTAGC SEQ ID NO: 2 | Hs.416073 | 153 bp |
| SUI1 | ATTGAGCATCCGGAATATGG SEQ ID NO: 3 | TGATCGTCCTTAGCCAGTCC SEQ ID NO: 4 | Hs.150580 | 101 bp |
| LTF | GACTCCATGGCAAAACAACA SEQ ID NO: 5 | GAGGAATTCACAGGCTTCCA SEQ ID NO: 6 | Hs.529517 | 121 bp |
| IHH | CGGCTTTGACTGGGTGTATT SEQ ID NO: 7 | GAAAATGAGCACATCGCTGA SEQ ID NO: 8 | Hs.654504 | 217 bp |
| Patched | TCGAAGGTGGAAGTCATTGAG SEQ ID NO: 9 | CACAGGGCATCTTTTCCATAA SEQ ID NO: 10 | Hs.494538 | 184 bp |
| OVGP1 | TATGTCCCGTATGCCAACAA SEQ ID NO: 11 | ACGTAGACAAGGGGGAAAGG SEQ ID NO: 12 | Hs.1154 | 253 bp |
| TOP2A | AAGCCCTCCTGCTACACATTT SEQ ID NO: 13 | CAGGCTTTTGAGAGACACCAG SEQ ID NO: 14 | Hs.156346 | 191 bp |
| CDK1 | GCTTATGCAGGATTCCAGGTT SEQ ID NO: 15 | CAATCCCCTGTAGGATTGGT SEQ ID NO: 16 | Hs.334562 | 143 bp |
| FLJ10540 | CTCAAGACCGTTGTCTCTTCG SEQ ID NO: 17 | TTCCCACTTGTGATTTCATCC SEQ ID NO: 18 | Hs.14559 | 197 bp |
| MT1H | GCAAGTGCAAAAAGTGCAAAT SEQ ID NO: 19 | CACTTCTCTGACGCCCCTTT SEQ ID NO: 20 | Hs.438462 | 115 bp |
| SCGB2A2 | ACCATGAAGTTGCTGATGGTC SEQ ID NO: 21 | GGCATTTGTAGTGGCATTGTC SEQ ID NO: 22 | Hs.46452 | 177 bp |
| CYP26A1 | GCATCGAGCAGAACATTCG SEQ ID NO: 23 | TGGAGAACATGTGGGTAGAGC SEQ ID NO: 24 | Hs.150595 | 235 bp |
| PSD | AGCTCCCAAAAGAAGTTCAGC SEQ ID NO: 25 | ACTCCAGGTAGGCCTCCTTCT SEQ ID NO: 26 | Hs.154658 | 199 bp |
| SH3D5 | CCACAGAATGATGATGAGTTGG SEQ ID NO: 27 | GTTGCCTGGAAAAGTACCAAA SEQ ID NO: 28 | Hs.696027 | 126 bp |
| TACC2 | AGGAGAGCCCTGTCAAGTCAT SEQ ID NO: 29 | GTTGTGGGAGGATTTCTCTGG SEQ ID NO: 30 | Hs.501252 | 185 bp |
| SEMA3C | AAGTCTCCGCAGGCATCTATC SEQ ID NO: 31 | CAACAGCCACCATTTGTGAAT SEQ ID NO: 32 | Hs.269109 | 226 bp |
| BIRC5 | CACTGAGAACGAGCCAGACTT SEQ ID NO: 33 | AACCGGACGAATGCTTTTTAT SEQ ID NO: 34 | Hs.514527 | 110 bp |
| ERRFI1/MIG6 | TTGCTGCTCAGGAGATCAGA SEQ ID NO: 35 | TTCAGACTGTAGGCCATGGTT SEQ ID NO: 36 | Hs.605445 | 154 bp |

TABLE 2-continued

Primer sequences used in real-time PCR reactions.

| Gene | Forward primer (5'-3') | Reverse primer (5'-3') | Unigene ID | Expected Product Length |
|---|---|---|---|---|
| ERBB2 | CCCTGGTCACCT ACAACACAG SEQ ID NO: 37 | CTCTGCTGTCAC CTCTTGGTT SEQ ID NO: 38 | Hs.446352 | 167 bp |
| FOXO1 | AAGAGCGTGCCC TACTTCAA SEQ ID NO: 39 | CTGTTGTTGTCC ATGGATGC SEQ ID NO: 40 | Hs.370666 | 209 bp |
| PLZF | CCACCCCTACGA GTGTGAGT SEQ ID NO: 41 | GCTTGATCATGG CCGAGTAG SEQ ID NO: 42 | Hs.591945 | 230 bp |
| SPP1 | AGAAGTTTCGCA GACCTGACA SEQ ID NO: 43 | GTCATCCAGCTG ACTCGTTTC SEQ ID NO: 44 | Hs.313 | 182 bp |

Cluster Analysis.

Principal component analysis (PCA) revealed that endometrial samples from subjects with endometriosis cluster by cycle phase with samples from subjects without disease (FIG. 1). PCA depicts the variance in gene expression profiles among specimens. For purposes of comparison, samples were grouped by cycle phase. On the three dimensional graphic, the distance between two plotted points is proportional to the degree of similarity between the two groups' gene expression profiles, using all of the genes and ESTs on the Affymetrix gene chip HG 133 Plus 2.0. Clustering was more dependent on cycle phase than endometriosis status. The largest variance between specimens from subjects with and without moderate/severe endometriosis was observed in the early secretory phase. Interestingly, the ESE specimens from women with endometriosis collectively plotted much closer to the PE specimens than did the normal ESE specimens, suggestive of attenuation of the progesterone mediated transition on the molecular level.

Figure 2:
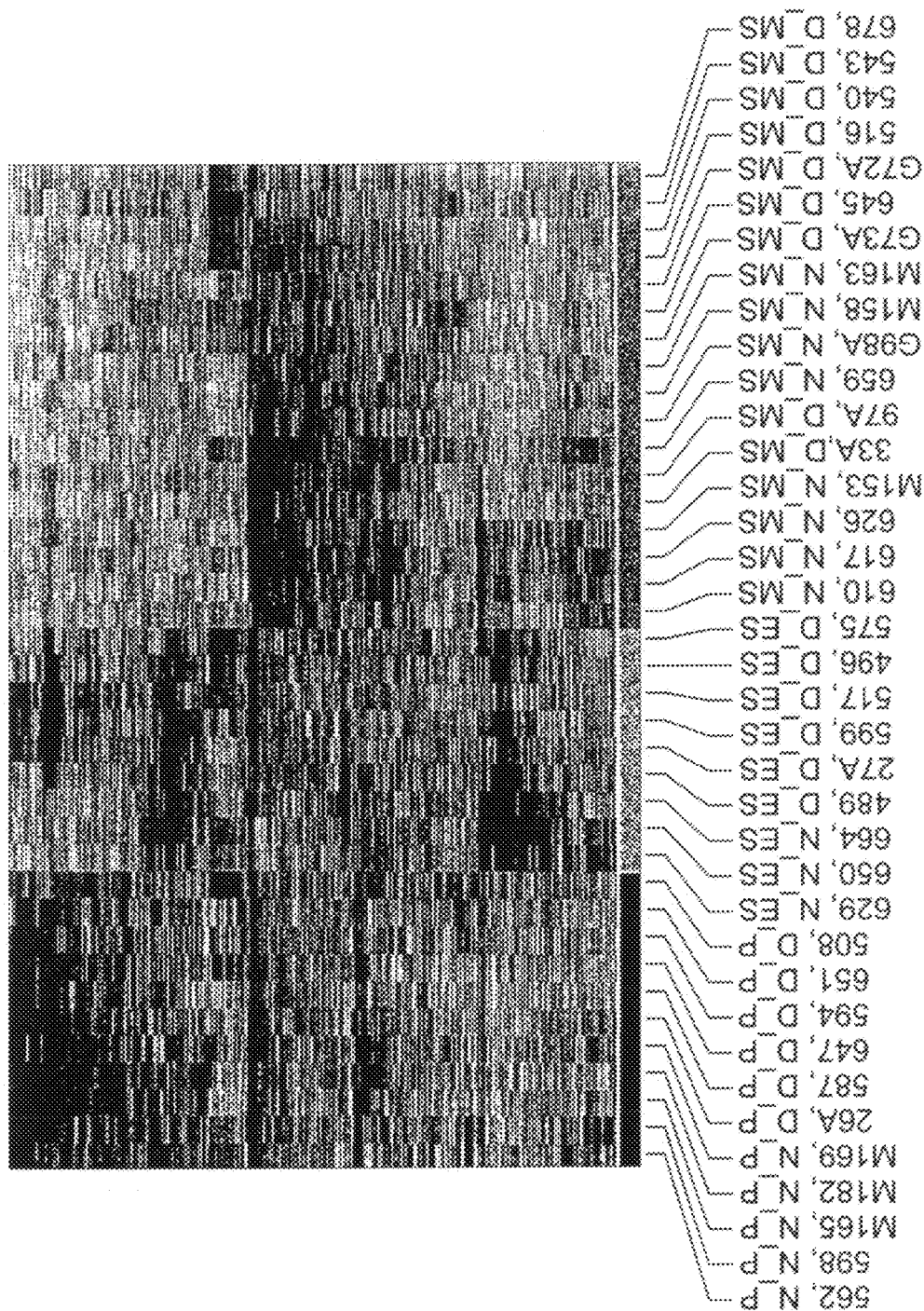
FIG. 2. Hierarchical clustering analysis of endometrium from subjects with moderate/severe endometriosis (D) and from subjects without disease (N) in the PE (red), ESE (gold) and MSE (light blue).

Unsupervised hierarchical clustering analysis was conducted using the gene expression profiles of the 37 endometrial samples (21 with endometriosis, 16 without endometriosis) based on the combined list of genes showing differential expression throughout the comparable phases of the menstrual cycle. As evidenced by the dendrogram of sample clustering (FIG. 2), the samples self-segregate according to cycle phase, confirming our previously reported observation of phase dependent segregation of endometrial samples (Talbi S et al. (2006) *Endocrinology* 147:1097-121). Additionally, within the early secretory cycle phase, the samples demonstrate striking self-segregation into normal and disease clusters. Three endometrial specimens sampled from patients with endometriosis (599, 517, and 27 A) were classified as late proliferative phase by the Noyes criteria (Noyes R W et al. (1975) *Am J Obstet Gynecol* 122:262-3), mostly on the basis of an increased number of mitotic figures observed in these histologic preparations. However, each specimen's overall gene expression profile clustered with the early secretory phase specimens. Dating of these specimens based on last menstrual period placed them collectively between cycle days 15 and 17, confirming their molecular-based dating in the early secretory phase. To further clarify the dating of these specimens, microarray analysis was conducted comparing these three specimens with the other three ESE specimens (489, 496, and 575). This sub-analysis showed no significant differences, thereby validating their correct classification as early secretory.

Expression Profiling Reveals Persistent Expression of Genes Involved in Cellular Proliferation in ESE from Women with Endometriosis.

Of the three phases of the menstrual cycle investigated, the early secretory phase involved the greatest number of statistically significant and differentially expressed genes in endometrium from women with versus without endometriosis (Table 3). The most highly up- and down-regulated genes are shown in Table 4. The complete gene lists for all cycle phases in women with disease versus women without endometriosis are provided in Burney et al. (Burney et al., *Endocrinology* 148(8):3814-3826 (2007)). The data have been submitted to the GEO database under the identifier GSE6364. The gene ontologies (GOs) enriched in the ESE of women with endometriosis are mostly involved with mitosis and cell proliferation (Table 7), processes which, in women without disease, are normally down-regulated in ESE (and up-regulated in PE). The complete GO categories for all phases are provided in (Burney et al., *Endocrinology* 148(8): 3814-3826 (2007)).

TABLE 3

Number of significantly differentially expressed genes in endometrium of endometriosis versus normal subjects at indicated fold change thresholds.

| Fold Change | 1.5x | | 2.0x | | 4.0x | |
|---|---|---|---|---|---|---|
| Menstrual phase | Up | Down | Up | Down | Up | Down |
| Proliferative | 252 | 447 | 24 | 14 | 2 | 0 |
| Early secretory | 747 | 1741 | 213 | 521 | 26 | 59 |
| Mid secretory | 428 | 293 | 4 | 22 | 0 | 0 |

TABLE 4

Most highly up- and down-regulated genes per cycle phase-dependent comparison. Fold changes provided compare the endometrium from women with vs. without moderate/severe endometriosis.

| Gene symbol | Description | Unigene ID | Fold Change | p value |
|---|---|---|---|---|
| *Proliferative Phase* | | | | |
| Up regulated | | | | |
| S100A8 | S100 calcium binding protein A8 | Hs.416073 | 4.95 | 0.0111 |
| SUI1 | Putative translation initiation factor | Hs.150580 | 3.74 | 0.0136 |
| LTF | Lactotransferrin | Hs.529517 | 3.51 | 0.0357 |
| GRAP | GRB2-related adaptor protein | Hs.567416 | 2.9 | 0.0125 |
| CD163 | CD163 antigen | Hs.504641 | 2.63 | 0.0038 |
| Down regulated | | | | |
| DEAD/H | DEAD (Asp-Glu-Ala-Asp) SEQ ID NO: 45 box polypeptide | Hs.528305 | −2.63 | 0.0015 |
| ORM2 | Orosomucoid 2 | Hs.522356 | −2.56 | 0.0383 |
| PGR | Progesterone receptor | AI378893 Hs.32405 | −2.33 | 0.0235 |
| IHH | Indian hedgehog homolog | Hs.654504 | −2.33 | 0.029 |
| OVGP1 | Oviductal glycoprotein 1 precursor | Hs.1154 | −2.32 | 0.0362 |
| *Early Secretory Phase* | | | | |
| Up regulated | | | | |
| TOP2A | Topoisomerase (DNA) II alpha 170 kDa | Hs.156346 | 7.59 | 0.0003 |
| RAB6KIFL | RAB6 interacting, kinesin-like | Hs.73625 | 5.19 | 0.0014 |
| APOBEC3B | Apolipoprotein B mRNA editing enzyme, catalytic polypeptide-like 3B | Hs.226307 | 5.12 | 0.0011 |
| PENK | Proenkephalin | Hs.339831 | 5.08 | <0.05 |
| TOPK | T-LAK cell-originated protein kinase | Hs.104741 | 5.05 | 0.0021 |
| Down regulated | | | | |
| MT1Y | Metallothionein 1Y | Hs.647370 | −11.1 | 0.0079 |
| SCYB13 | CXCL13: Chemokine ligand 13 (B-cell chemoattractant) | Hs.100431 | −9.09 | 0.0018 |
| CYP26A1 | Cytochrome P450, subfamily XXVIA | Hs.150595 | −8.33 | 0.0306 |
| SCGB2A2 | Secretoglobin, family 2A, member 2 | Hs.46452 | −7.69 | 0.0203 |
| MT1G | Metallothionein 1G | Hs.433391 | −7.14 | 0.0054 |
| *Mid Secretory Phase* | | | | |
| Up regulated | | | | |
| S100A8 | S100 calcium binding protein A8 | Hs.416073 | 2.11 | 0.0156 |
| BLTR2 | Leukotriene B4 receptor BLTR2 | Hs.642693 | 2.02 | 0.0005 |
| MAPK4 | Mitogen-activated protein kinase 4 | Hs.433728 | 1.98 | 0.00001 |
| PTAFR | Platelet-activating factor receptor | Hs.433540 | 1.91 | 0.002 |
| GZMA | Granzyme A | Hs.90708 | 1.87 | 0.0286 |
| Down regulated | | | | |
| SCGB2A2 | Secretoglobin, family 2A, member 2 | Hs.46452 | −3.33 | 0.0447 |
| MMP26 | Matrix metalloproteinase 26 | Hs.204732 | −3.03 | 0.0457 |
| CYP26A1 | Cytochrome P450, subfamily XXVIA | Hs.150595 | −2.63 | 0.0306 |
| POMZP3 | POM (POM121 homolog, rat) and ZP3 fusion | Hs.488877 | −2.56 | 0.0019 |
| DEPP/C10orf10 | Chromosome 10 open reading frame 10 | Hs.93675 | −2.38 | 0.0129 |

To further define the observation of a persistent cellular proliferation signature in early secretory phase endometrium from women with endometriosis, we examined expression of individual genes mapped in the KEGG cell cycle pathway (FIG. 4, for KEGG pathway analysis for all phases). As demonstrated, multiple genes involved in mitotic cell cycle regulation are differentially expressed. The finding of a coherent pattern of consistent dysregulation among multiple genes involved in a pathway or process improves the robustness of the finding. Importantly, gene ontology analysis of differentially expressed genes in the proliferative phase did not demonstrate enrichment for genes involved in the cell cycle in endometrium from women with endometriosis. Therefore, the finding of a proliferative gene expression profile persisting in early secretory endometrium of these women is consistent with reduced progesterone mediated inhibition of estrogen-induced cellular mitosis.

Progesterone Regulated Genes in ESE and MSE from Women with Versus without Endometriosis.

Genes known to be progesterone-regulated for dysregulation during the secretory phase in the endometrium from women with endometriosis were further investigated. Progesterone-regulated genes were identified by systematic review of the literature using the PubMed search engine, and were compared against our dataset of differentially expressed genes in the secretory phases among women with versus without endometriosis. This approach revealed fifty-four and sixteen dysregulated genes in the ESE and MSE, respectively (Table 5).

TABLE 5

Genes previously shown to be progesterone regulated that are dysregulated in endometrium of subjects with moderate/severe endometriosis. A, Early secretory phase. B, Mid secretory phase. Values indicate fold change of each gene in eutopic endometrium from subjects with endometriosis relative to control endometrium.

| Gene symbol | Description | Evidence for P-regulation | Unigene ID | Fold change | p value |
|---|---|---|---|---|---|
| A. Early secretory phase (n = 54) | | | | | |
| Down regulated | | | | | |
| MT1Y | Metallothionein 1Y | (25) | Hs.647370 | −11.1 | 0.0079 |
| CYP26A1 | Cytochrome P450, subfamily XXVIA | (54) | Hs.150595 | −8.33 | 0.0306 |
| SCGB2A2 | Secretoglobin, family 2A, member 2 | (25, 73) | Hs.46452 | −7.69 | 0.0203 |
| MT1G | Metallothionein 1G | (25, 73, 74) | Hs.433391 | −7.14 | 0.0054 |
| MT1X | Metallothionein 1X | (25, 75) | Hs.374950 | −7.14 | 0.0046 |
| MT1F | Metallothionein 1F | (25) | Hs.513626 | −6.67 | 0.0073 |
| CAPN6 | Calpain 6 | (25, 54) | Hs.496593 | −6.25 | 0.0018 |
| MT1H | Metallothionein 1H | (25) | Hs.438462 | −5.56 | 0.0092 |
| SPP1 | Secreted phosphoprotein 1, osteopontin) | (25, 74) | Hs.313 | −5.56 | 0.0154 |
| MT1E | Metallothionein 2A | (25, 73-75) | Hs.647371 | −4.55 | 0.0157 |
| ISG20 | Interferon stimulated gene, 20-Kd | (54) | Hs.459265 | −3.85 | 0.0008 |
| MAOA | Monoamine oxidase A | (25, 74, 76) | Hs.183109 | −3.03 | 0.0022 |
| GPX3 | Glutathione peroxidase 3 | (74) | Hs.386793 | −2.78 | 0.0172 |
| MIG6/ERRFI1 | Mitogen-inducible gene 6 | (77) | Hs.605445 | −2.7 | 0.0025 |
| SGK | Serum/glucocorticoid regulated kinase | (54, 75) | Hs.725237 | −2.63 | 0.0296 |
| DEPP/C10orf10 | Chromosome 10 open reading frame 10 | (75, 78) | Hs.93675 | −2.5 | 0.0234 |
| DKK1 | Dickkopf homolog 1 | (8, 25, 74, 75, 79) | Hs.40499 | −2.44 | <0.05 |
| MUC1 | Mucin 1, transmembrane | (25) | Hs.89603 | −2.38 | 0.0094 |
| PAEP | Progestagen-associated endometrial protein/Glycodelin | (80-82) | Hs.532325 | −2.33 | <0.05 |
| FOXO1A | Forkhead box O1A | (25, 83) | Hs.370666 | −2.27 | 0.016 |
| STC1 | Stanniocalcin 1 | (84) | Hs.25590 | −2.08 | 0.0476 |
| BCAT1 | Branched-chain aminotransferase 1 | (54) | Hs.438993 | −2 | 0.0467 |
| BCL6 | B-cell CLL/lymphoma 6 | (75) | Hs.478588 | −2 | 0.0024 |
| ALDH1A3 | Aldehyde dehydrogenase 1 family, A3 | (75) | Hs.459538 | −1.96 | <0.05 |
| NFIL3 | Nuclear factor, interleukin 3 regulated | (54) | Hs.79334 | −1.92 | 0.0167 |
| CITED2 | Cbp/p300-interacting transactivator | (54) | Hs.82071 | −1.85 | 0.0097 |
| SAT1 | Spermidine acetyltransferase 1 | (73, 74, 85) | Hs.28491.3 | −1.85 | 0.0063 |
| RGC32 | RGC32 protein | (75) | Hs.507866 | −1.82 | 0.0171 |
| G0S2 | Putative lymphocyte G0/G1 switch gene | (75) | Hs.432132 | −1.79 | 0.0441 |
| PTGER2 | Prostaglandin E receptor 2 (subtype EP2) | (75) | Hs.2090 | −1.79 | 7.87E−06 |
| PFKFB3 | 6-phosphofructo-2-kinase/fructose-2,6-biphosphatase 3 | (54) | Hs.195471 | −1.75 | 0.0156 |
| PPAP2B | Phosphatidic acid phosphatase, type 2B | (54) | Hs.405156 | −1.69 | 0.0028 |
| IRS2 | Insulin receptor substrate 2 | (75) | Hs.442344 | −1.67 | 0.019 |
| ELL2 | Elongation factor, RNA polymerase II | (75) | Hs.592742 | −1.64 | 0.045 |
| SLC2A3 | Solute carrier family 2, member 3 | (54) | Hs.419240 | −1.61 | 0.0024 |
| PLCB4 | Phospholipase C, beta 4 | (75) | Hs.472101 | −1.61 | 0.0177 |
| REV3L | REV3-like, catalytic subunit of DNA polymerase zeta | (75) | Hs.232021 | −1.61 | <0.05 |
| IL1R1 | Interleukin 1 receptor, type I | (75) | Hs.701982 | −1.59 | 0.011 |
| ATP1B1 | ATPase, Na+/K+ transporting, beta-1 | (54) | Hs.291196 | −1.58 | 0.0477 |
| TGFB2 | Transforming growth factor, beta 2 | (86, 87) | Hs.133379 | −1.52 | 0.0144 |
| Up regulated | | | | | |
| PENK | Proenkephalin | (25, 73, 74, 88, 89) | Hs.339831 | 5.08 | <0.05 |
| SFRP4 | Secreted frizzled-related protein 4 | (73, 74, 89, 90) | Hs.658169 | 4.94 | 0.0431 |
| MMP11 | Matrix metalloproteinase 11 | (25, 73, 74, 89, 91) | Hs.143751 | 4.02 | <0.05 |
| OLFM1 | Olfactomedin 1 | (25) | Hs.522484 | 3.45 | 0.0169 |
| TGFBI | Transforming growth factor, beta-induced | (54, 73, 74, 89) | Hs.369397 | 3.14 | 0.0137 |

TABLE 5-continued

Genes previously shown to be progesterone regulated that are dysregulated in endometrium of subjects with moderate/severe endometriosis. A, Early secretory phase. B, Mid secretory phase. Values indicate fold change of each gene in eutopic endometrium from subjects with endometriosis relative to control endometrium.

| Gene symbol | Description | Evidence for P-regulation | Unigene ID | Fold change | p value |
|---|---|---|---|---|---|
| TK1 | Thymidine kinase 1, soluble | (73) | Hs.515122 | 2.5 | 0.0005 |
| MEST | Mesoderm specific transcript homolog | (75) | Hs.270978 | 2.43 | <0.05 |
| THY1 | Thy1 cell surface antigen | (25, 73) | Hs.653181 | 2.35 | 0.0231 |
| RRM1 | Ribonucleotide reductase M1 polypeptide | (73) | Hs.558393 | 2.25 | 0.0364 |
| HMGA2 | High-mobility group box 2 | (54) | Hs.434953 | 2.15 | 0.002 |
| PGR | Progesterone receptor | (35, 36) | Hs.32405 | 2.12 | 0.0322 |
| FBN1 | Fibrillin 1 | (73) | Hs.591133 | 2.03 | 0.0404 |
| BCL2 | B-cell CLL/lymphoma 2 | (54) | Hs.150749 | 1.72 | 0.0321 |
| MARCKS | Myristoylated alanine-rich protein kinase C substrate | (54, 73) | Hs.519909 | 1.52 | 0.0552 |
| B. Mid secretory phase (n = 16) | | | | | |
| Down regulated | | | | | |
| SCGB2A2 | Secretoglobin, family 2A, member 2 | (25, 73) | Hs.46452 | −3.33 | 0.0447 |
| CYP26A1 | Cytochrome P450, subfamily XXVIA | (25, 54) | Hs.150595 | −2.63 | 0.0306 |
| DEPP/C10orf10 | Chromosome 10 open reading frame 10 | (75, 78) | Hs.93675 | −2.38 | 0.0129 |
| SLC15A2 | Solute carrier family 15, member 2 | (73) | Hs.518089 | −1.92 | 0.0107 |
| IGFBP1 | Insulin-like growth factor binding protein 1 | (92) | Hs.642938 | −1.85 | <0.05 |
| ATP1B1 | ATPase, Na+/K+ transporting, beta-1 | (54) | Hs.291196 | −1.85 | <0.05 |
| ELL2 | Elongation factor, RNA polymerase II | (75) | Hs.592741 | −1.69 | 0.0461 |
| MT1Y | Metallothionein 1Y | (25) | Hs.647370 | −1.67 | <0.05 |
| CAPN6 | Calpain 6 | (25, 54) | Hs.496593 | −1.64 | <0.05 |
| ENPP1 | Ectonucleotide pyrophosphatase/phosphodiesterase 1 | (54) | Hs.527295 | −1.59 | 0.0479 |
| MUC1 | Mucin 1, transmembrane | (25, 93) | Hs.89603 | −1.56 | 0.0391 |
| PIP5K1B | Phosphatidylinositol-4-phosphate 5-kinase, type I, beta | (54) | Hs.534371 | −1.56 | 0.0078 |
| FOXO1A | Forkhead box O1A | (25) | Hs.370666 | −1.54 | 0.023 |
| SAT1 | Spermidine acetyltransferase 1 | (73, 74, 85) | Hs.28491.3 | −1.52 | 0.0063 |
| Up regulated | | | | | |
| BCL2 | B-cell CLL/lymphoma 2 | (54) | Hs.150749 | 1.76 | 0.0009 |
| PCK1 | Phosphoenolpyruvate carboxykinase 1 | (54) | Hs.1872 | 1.68 | 0.0463 |

Comparison of Moderate/Severe Endometriosis Vs. Normal and Minimal/Mild Endometriosis Vs. Normal Datasets.

The list of differentially expressed genes during the mid-secretory phase identified in the current study was compared with the gene list previously obtained in a comparison of endometrial gene expression profiles during the implantation window in women with vs. without minimal/mild endometriosis (Kao L C et al. (2003) *Endocrinology* 144: 2870-81). The two datasets shared five up-regulated genes and twelve down-regulated genes of 1.5 fold or greater (Table 6). Four of the five upregulated genes are involved in the immune (GZMA, C4BPA) or inflammatory (S100A8, S100A9) responses.

TABLE 6

Differentially expressed genes in the mid-secretory phase eutopic endometrium common to both the minimal/mild endometriosis vs. normal and moderate/severe endometriosis vs. normal datasets. Fold change and p values are those for the current study.

| Symbol | Description | Unigene ID | Fold change | p value |
|---|---|---|---|---|
| Up-regulated genes (n = 5) | | | | |
| S100A8 | S100 calcium binding protein A8 | Hs.416073 | 2.11 | 0.0156 |
| GZMA | Granzyme A | Hs.90708 | 1.87 | 0.0286 |

TABLE 6-continued

Differentially expressed genes in the mid-secretory phase eutopic endometrium common to both the minimal/mild endometriosis vs. normal and moderate/severe endometriosis vs. normal datasets. Fold change and p values are those for the current study.

| Symbol | Description | Unigene ID | Fold change | p value |
|---|---|---|---|---|
| S100A9 | S100 calcium binding protein A9 | Hs.112405 | 1.71 | 0.0075 |
| C4BPA | Complement component 4 binding protein, alpha | Hs.1012 | 1.7 | 0.0018 |
| KIAA0352 | KIAA0352 gene product | Hs.591025 | 1.55 | 3.92E−07 |
| Down-regulated genes (n = 12) | | | | |
| PTPRR | Protein tyrosine phosphatase, receptor type, R | Hs.506076 | −2.13 | 0.0015 |
| SLC15A2 | Solute carrier family 15, member 2 | Hs.518089 | −1.92 | 0.0107 |
| PLA2G4A | Phospholipase A2, group IVA | Hs.497200 | −1.75 | 0.0397 |
| RBP4 | Retinol binding protein 4 | Hs.50223 | −1.72 | <0.05 |
| KIAA1199 | KIAA1199 protein | Hs.459088 | −1.72 | 0.0349 |
| HLA-DOB | Major histocompatibility complex, class II, DOB | Hs.1802 | −1.69 | 0.001 |
| ANK3 | Ankyrin 3, node of Ranvier (ankyrin G) | Hs.499725 | −1.67 | 0.0202 |
| MUC1 | Mucin 1, transmembrane | Hs.89603 | −1.56 | 0.0391 |
| C11orf8 | Chromosome 11 open reading frame 8 | Hs.178576 | −1.56 | 0.0194 |
| KRT8 | Keratin 8 | Hs.533782 | −1.56 | 0.0345 |
| PIP5K1B | Phosphatidylinositol-4-phosphate 5-kinase, type I | Hs.534371 | −1.56 | 0.0078 |
| S100A1 | S100 calcium binding protein Al | Hs.515715 | −1.5 | 0.0023 |

TABLE 7

Gene ontology data
Gene Ontology Data

ES Phase - Enriched GO categories
Biological Processes
Up regulated
N = 53 total processes Mitotic spindle elongation (100)
Spindle checkpoint (50)
Spindle organization/biogenesis (50)
Traversing start control point (42.8)
Mitotic checkpoint (38.5)
Deoxyribonucleotide metabolism (25)
DNA integrity checkpoint (25)
DNA damage checkpoint (25)
Chromosome cycle (23)
DNA replication initiation (22.7)
G2/M transition of cell cycle (18)
Mitosis (16.5)
Down regulated Regulation of neurotransmitter lvls
Homeostasis: cell, ion, copper, inorganic cation
Actin filament bundle formation
Cholesterol biosynthesis
Protein-cofactor linkage
Transport: organic, carboxylic acid
Molecular Functions
Up regulated Double stranded DNA binding
Nucleotide binding
ATP binding
ATPase activity
Oxidoreductase activity
Ribonucleoside diphosphate reductase activity
Small protein activating enzyme activity
Ubiquitin like activating enzyme activity
Protein kinase activity
Microtubule motor activity
Down regulated Cadmium ion binding
Copper ion binding Monocarboxylate porter activity
Transport activity: sulfate, organic acid, carboxylic acid, monocarboxylic acid
Cellular Components
Up regulated Chromosome/chromatin
Kinetochore
Cytoskeleton
Microtubule cytoskeleton
Spindle microtubule
Microtubule associated complex
Kinesin complex
Intracellular organelle
Nucleus
Nuclear lamina
Non-membrane bound organelle
Down regulated Cell fraction
Membrane fraction
Membrane
P Phase - Enriched GO categories
Biological Processes
Up regulated Cell ion homeostasis
Cation homeostasis
Inorganic ion homeostasis
Iron ion homeostasis
Metal ion homeostasis
Inorganic cation transport
Transition metal ion transport
Ion homeostasis
Immune response
Humoral immune response
Inflammatory response
Response to biotic/external stimulus
Response to stress
Molecular Functions TABLE 7-continued Gene ontology data
Gene Ontology Data Up regulated Iron ion binding
Cellular Components
Up regulated Extracellular region
Extracellular space Differentially Expressed Genes in the Region of a Locus Showing Linkage with Endometriosis in a Genome Wide Linkage Analysis.

Recently, Treloar et al published the results of a genome-wide linkage analysis study involving 1176 families with affected sib pairs (Treloar S A et al. (2005) *Am J Hum Genet* 77:365-76). This effort identified a region of significant linkage to endometriosis on chromosome 10q26. We searched the genome for genes that fell within the 95% CI of this 10q26 locus and compared these against our dataset of differentially expressed genes in the endometrium of women with endometriosis relative to normal endometrium. This analysis identified the following four genes (fold change in endometriosis vs. normal endometrium for indicated cycle phase): transforming, acidic coiled-coil containing protein 2, TACC2 (10q26; −2.86 ESE, −1.59 MSE), a disintegrin and metalloproteinase domain 12, ADAM12 (10q26.3; 2.29 ESE), arginyltransferase 1, ATE1 (10q26.13; 1.61 PE, 1.57 ESE), and fibronectin type III and ankyrin repeat domains 1, FANK1 (10q26.2; −1.85 ESE). Other genes of interest near the 10q26 locus include cytochrome P450, family 26, subfamily A, polypeptide 1, CYP26A1 (10q23-24; −8.33 ESE, −2.63 MSE), retinol binding protein 4, RBP4 (10q23-24; −1.72 MSE), pleckstrin and Sec7 domain protein, PSD (10q24; 2.10 ESE, 1.73 MSE), sorbin and SH3 domain containing 1, SH3D5 (10q23-24; 1.61 MSE) (Table 8).

Real-Time PCR Validation of Microarray Data.

Three up-regulated and three down-regulated genes in each cycle phase comparison (of moderate/severe disease vs. women without endometriosis) that showed statistical significance in the microarray dataset were chosen for validation by real-time PCR (FIG. 3). All the genes regulated in the proliferative phase, as shown by microarray, were confirmed to demonstrate statistically significant regulation in the same direction by real-time PCR (100% concordance). For the early-secretory phase, all genes selected for validation exemplified similar direction of regulation to the microarray data, of which 5 were statistically significant for a concordance of 83%. The exception was CYP26A1, which showed a fold change in the real-time PCR analysis that did not reach statistical significance (P=0.097). In the mid-secretory phase, five of the six genes selected for validation showed similar directional change, and four of these achieved statistical significance for a concordance of 67%. The overall concordance rate of significantly regulated genes between the microarray data and the real-time PCR data was 83% (15/18).

Maintenance of a Proliferative Fingerprint in the ESE from Women with Endometriosis.

A striking enrichment of genes involved in mitosis and proliferation in early secretory endometrium of women with endometriosis was observed (FIG. 4), exceptional insofar as these processes are normally down-regulated in this phase of the cycle and up-regulated during the proliferative phase (Talbi S et al. (2006) *Endocrinology* 147:1097-121). The finding of enrichment of genes involved in cell cycle regulation was consistent among all ESE specimens from subjects with endometriosis, including those specimens demonstrating concordance for ESE assignment by both histologic and molecular dating. Although the overall molecular signature is consistent with the early secretory phase, the genes involved in cell proliferation maintain a fingerprint more consistent with the proliferative phase. A recent study of gene and protein expression in murine luminal epithelium provided evidence for direct inhibition by P of estrogen-induced DNA synthesis in the cell cycle (Pan H et al. (2006) *Proc Natl Acad Sci USA* 103:14021-6). This study showed progesterone down-regulated over twenty genes associated with DNA rep-

TABLE 8

Differentially expressed genes in the vicinity of the locus linked with endometriosis.

| Gene | Locus | Description | Unigene ID | Phase | Fold Change |
|------|-------|-------------|------------|-------|-------------|
| TACC2 | 10q26 | Transforming, acidic coiled-coil containing protein 2 | Hs.501252 | ES | −2.86 |
| | | | | MS | −1.59 |
| ADAM12 | 10q26.3 | A disintegrin and metalloproteinase domain 12 | Hs.655388 | ES | 2.29 |
| ATE1 | 10q26.13 | Arginyltransferase 1 | Hs.632080 | ES | 1.57 |
| FANK1 | 10q26.2 | Fibronectin type III and ankyrin repeat domains 1 | Hs.352591 | ES | −1.85 |
| HELLS | 10q24.2 | Helicase, lymphoid-specific | Hs.655830 | ES | 2.99 |
| PSD | 10q24 | Pleckstrin and Sec7 domain protein | Hs.154658 | ES | 2.1 |
| | | | | MS | 1.73 |
| SORBS1 | 10q23-24 | Sorbin and SH3 domain containing 1 | Hs.696027 | MS | 1.61 |
| CYP26A1 | 10q23-24 | Cytochrome P450, subfamily XXVIA | Hs.150595 | ES | −8.33 |
| | | | | MS | −2.63 |
| RBP4 | 10q23-24 | Retinol binding protein 4 | Hs.50223 | MS | −1.72 |
| CEP55 | 10q23.33 | Centrosomal protein 55 kDa | Hs.14559 | ES | 3.5 | lication, most notably the minichromosome maintenance (MCM) family. Transcripts for 5 Mcm genes were found to be down-regulated, suggesting this pathway to be a major target of progesterone action. Interestingly, our study demonstrated up-regulation of all 6 MCM genes in the ESE from women with endometriosis. Other genes associated with cell cycle and DNA replication that showed down-regulation in response to progesterone in the study by Pan et al but up-regulation in the ESE from women with endometriosis include PCNA, MKI67, TK1, CCNE1, MAD2L1. Since progesterone is regarded as the key regulator in shifting the endometrium from the proliferative to the differentiated state (Giudice L C, Ferenczy, A. (1995) In: Adashi E Y et al. (ed) *Reproductive Endocrinology, Surgery and Technology*. Raven Press, New York, pp 171-194), these findings suggest that the pathway(s) governing this transition are dysfunctional in the endometrium of subjects with endometriosis.

The molecular mechanisms responsible for the persistence of a proliferative profile in the early secretory endometrium of women with endometriosis are unclear, but could result from altered ligand-receptor interactions, co-activators/repressors, or post-receptor signaling (Attia G R et al. (2000) *J Clin Endocrinol Metab* 85:2897-902; Bergqvist A, Ferno M (1993) *Hum Reprod* 8:2211-7; Lessey B A et al. (1989) *Fertil Steril* 51:409-15). Differential expression of genes within the progesterone and epidermal growth factor receptor (EGFR) signaling cascades that may be associated with the maintenance of the proliferative fingerprint was identified in the present study.

The human progesterone receptor (PR) gene contains several biologically active estrogen response elements (Savouret J F et al. (1991) *Embo J* 10:1875-83). Both PR-A and PR-B isoforms are highly expressed in response to estrogen in human endometrium before ovulation, but their expression is down-regulated by progesterone during endometrial maturation (Feil P D et al. (1988) *Endocrinology* 123:2506-13; Lessey BA et al. (1988) *J Clin Endocrinol Metab* 67:334-40). In the current study, PR is not suppressed in ESE (fold change 2.12) from women with versus without disease. Previously, an immunohistochemical study reported significantly increased PR expression in the epithelial compartment but not the stromal compartment in the ESE of women with endometriosis (Jones R K et al (1995) *Hum Reprod* 10:3272-9. In addition, studies have demonstrated differential PR isoform expression in the stromal versus epithelial compartments (Mote P A et al. (1999) *J Clin Endocrinol Metab* 84:2963-71).

The FOXO1A gene encodes a progesterone-regulated transcription factor involved in cell cycle control and the induction of apoptosis that is markedly induced upon decidualization of endometrial stromal cells in both in vivo and in vitro assays in response to progesterone and cAMP (Accili D, Arden K C (2004) *Cell* 117:421-6). These data (ESE fold change −2.27, MSE fold change −1.54) corroborate previous findings by others of reduced FOXO1 gene expression in the endometrium of subjects with endometriosis (Shazand K et al. (2004) *Mol Hum Reprod* 10:871-7; Matsuzaki S et al. (2005) *Fertil Steril* 84 Suppl 2:1180-90). This finding was confirmed by real-time PCR (ESE fold change −4.00). The reduced FOXO1A expression in the endometrium of subjects with endometriosis relative to controls is consistent with a phenotype of attenuated progesterone response and may play a role in the incomplete transitioning of the endometrium from the proliferative-to-early secretory phase.

The molecular mechanism(s) responsible for the persistence of a proliferative profile in the ESE of women with endometriosis may involve non-steroidal signaling pathways. The present study shows dysregulation of several anti-proliferative genes in the EGFR signaling cascade. Growth factors contribute to maximal proliferation of steroid dependent cells in normal endometrium (Giudice L C (1994) *Fertil Steril* 61:1-17), and the EGFR pathway is involved in the control of human endometrial growth (Irwin J C et al. (1991) *Endocrinology* 129:2385-92). Mitogen-inducible gene 6 (MIG6) functions as a negative regulator of EGFR-mediated mitogenic signaling. In the present dataset, MIG6 demonstrated statistically significant down-regulation (fold change −2.70) in ESE of subjects with moderate/severe endometriosis relative to endometrium of subjects without disease and this was validated by real-time PCR (fold change −6.67). Also known as ERFFI1 (for ERBB receptor feedback inhibitor 1), this protein regulates the duration of MAPK activation via attenuation of EGFR autophosphorylation in a mouse knockout model (Ferby I et al. (2006) *Nat Med* 12:568-73). Interestingly, the MIG6 locus (1p36.12-33) falls within a region that is a frequent site of allelic loss in human tumors (Koshikawa K et al. (2004) *Hepatogastroenterology* 51:186-91; Tseng R C, et al. (2005) *Int J Cancer* 117:241-7), and a recent study using comparative genomic hybridization (CGH) to compare the profiles of eutopic and ectopic endometrium in subjects with endometriosis identified shared allelic loss at 1p36 in two of three subjects (Wu Y et al. (2006) *Gynecol Obstet Invest* 62:148-159). Down-regulation or loss of MIG6 function may be associated with a conferred survival advantage to the refluxed endometrium in the establishment of endometriotic lesions. Additionally, downregulation of TOB1 (fold change −2.44) in the ESE of women with endometriosis was demonstrated in this study. TOB1, or transducer of ErbB-2, is a cell cycle regulatory protein associated with anti-proliferative activity (Matsuda S et al. (1996) *Oncogene* 12:705-13). Studies of cultured human endometrial stromal cells from women with endometriosis demonstrated reduced TOB1 expression after treatment with IL-1β, a central cytokine in endometriosis (Lebovic D I et al. (2002) *Fertil Steril* 78:849-54). The TOB1 gene is located on chromosome 17q21, and functional loss of this chromosomal region has been observed in endometriotic lesions (Kosugi Y et al. (1999) *Am J Obstet Gynecol* 180:792-7). The differential expression of several genes involved in checking the mitogenic action of the EGFR signaling cascade is intriguing.

Dysregulation of Progesterone Target Genes in the Secretory Endometrium of Women with Endometriosis.

In addition to genes involved in cellular proliferation, the secretory phase profiles of many P-regulated genes in eutopic endometrium of women with endometriosis provide further evidence of a relative reduction in progesterone response. Fifty-four genes in the ESE and sixteen genes in the MSE evidenced dysregulation in women with disease (Table 5). Metallothioneins (MT) comprise a family of genes clustered on chromosome 16q that bind to heavy metal ions and minimize reactive oxygen species. Previous studies demonstrated high MT expression in the secretory phase endometrium of women without endometriosis (Talbi S et al. (2006) *Endocrinology* 147:1097-121), and low MT expression in endometriotic implants (Wicherek L et al. (2005) *Gynecol Oncol* 99:622-30). In the present study, the MTs were among the most highly down-regulated genes in the ESE of women with endometriosis, and this was validated by real-time PCR (MT1H fold change −33.33). Glutathione peroxidase (GPX3), also up-regulated during the secretory phase in normal endometrium, shares the MT pathway and evidenced significantly reduced expression (ESE fold change −2.78) in the eutopic endometrium of women with endometriosis. The anti-apoptotic gene, BCL-2, is increased in ESE of women with endometriosis, confirming studies by others (Jones R K et al. (1998) Hum Reprod 13:3496-502; Meresman G F et al. (2000) Fertil Steril 74:760-6) and suggesting mechanisms for enhanced cell survival in the pathogenesis of this disorder. Interestingly, this gene is negatively regulated by progesterone in mouse uterus (Jeong J W et al. (2005) Endocrinology 146:3490-505). Another P-regulated gene evidencing striking dysregulation in the endometrium of subjects with endometriosis is CYP26A1. In normal premenopausal endometrium, the gene expression of this retinoic acid catabolic enzyme markedly increases in the secretory phase (Deng L et al. (2003) J Clin Endocrinol Metab 88:2157-63). In a microarray study comparing genes induced by progesterone in the uteri of wild type versus PR knockout mice, CYP26A1 was the most highly up-regulated gene in response to progesterone (Jeong J W et al. (2005) Endocrinology 146: 3490-505). In women with moderate/severe endometriosis relative to controls, CYP26A1 is among the most significantly down-regulated genes in both the ESE and MSE, with fold changes of −8.33 and −2.63, respectively and validated by real time RT-PCR. Interestingly, the genetic locus for CYP26A1 maps close to a region of the genome recently identified to be significantly associated with endometriosis in a genome wide linkage study (Treloar S A et al. (2005) Am J Hum Genet 77:365-76).

Clinical Implications of Attenuated Progesterone Action—Implantation Failure.

An association between endometriosis and infertility is well established (Hahn D W et al. (1986) Am J Obstet Gynecol 155:1109-13; Schenken R S, Asch R H (1980) Fertil Steril 34:581-7; Steinleitner A et al. (1990) Fertil Steril 53:926-9; Brosens I (2004) Fertil Steril 81:1198-200; Jansen R P (1986) Fertil Steril 46:141-3; Barnhart K et al. (2002) Fertil Steril 77:1148-55). Attenuation of P response at the level of the endometrium may be expected to have a deleterious impact on endometrial receptivity, and a significant reduction of the implantation rate in women with endometriosis undergoing IVF has been reported (Cahill D J, Hull M G (2000) Hum Reprod Update 6:56-66). A prior study identified an altered transcriptome in the endometrium of women with minimum/mild endometriosis during the window of implantation (Kao L C et al. (2003) Endocrinology 144:2870-81). Systematic comparison of the list of differentially expressed genes in the mid-secretory phase of the current study with that of the prior study showed seventeen genes to be common (Table 6). In the context of attenuated P response and implantation failure, several genes are of interest. MUC-1 and osteopontin, important in embryo attachment, and glycodelin, important in the immune response during implantation, were down-regulated in secretory endometrium of women with versus without endometriosis. We observed a nearly 2-fold reduction in expression of insulin-like growth factor binding protein-1 (IGFBP-1) during the window of implantation in the endometrium from women with disease. IGFBP-1 is a sensitive marker for endometrial stromal cell decidualization, and a reduction in IGFBP-1 secretion by cultured endometrial stromal fibroblasts from women with endometriosis relative to those from women without disease has been documented (Klemmt P A et al. (2006) Fertil Steril 85:564-72). These findings suggest impaired decidualization of the endometrium in women with endometriosis, which may have important biochemical implications for uterine receptivity.

Mechanism of Attenuated Progesterone Response.

This study demonstrates abnormalities in eutopic endometrium of women with endometriosis, primarily in the early secretory phase, suggestive of reduced P response in the transition from the proliferative to secretory phases. In addition, a number of progesterone-regulated genes evidence dysregulation in secretory phase endometrium. In vivo observations and in vitro studies suggest an intrinsic resistance to progesterone action in eutopic endometrium of women with endometriosis.

Progesterone resistance exists when normal levels of progesterone elicit a subnormal or reduced response. Studies are conflicting regarding the normalcy of circulating levels of progesterone in women with endometriosis (Brosens I A et al. (1978) Br J Obstet Gynaecol 85:246-50; Cheesman K L et al. (1983) Fertil Steril 40:590-5; Williams C A et al. (1986) Clin Reprod Fertil 4:259-68; Kusuhara K (1992) Am J Obstet Gynecol 167:274-7; Cunha-Filho J S et al. (2003) J Assist Reprod Genet 20:117-21), and this discrepancy may be secondary to difficulties in both ascertainment and interpretation of circulating progesterone levels. A single serum progesterone level may not be representative of luteal adequacy (Abraham G E et al. (1974) Obstet Gynecol 44:522-5; Laufer N et al. (1982) Am J Obstet Gynecol 143:808-13), and successful intrauterine pregnancy has been documented with mid-luteal P levels as low as 3-4 ng/ml (Costello M F et al. (2004) Aust N Z J Obstet Gynaecol 44:51-6). Finally, a study of luteal endometrial differentiation in programmed cycles of physiologic and subphysiologic exogenous progesterone replacement in GnRH agonist-suppressed healthy volunteers showed no differences in endometrial thickness, histology or epithelial integrin expression at the lower serum progesterone level (Usadi RS et al. (2003) J Soc Gynecol Investig 10:Suppl). This finding supports the argument that the reduced progesterone response in the eutopic endometrium of women with endometriosis is an intrinsic biologic alteration of the endometrium.

The evidence to support progesterone resistance in the setting of endometriosis is substantial. Endometrial stromal fibroblasts obtained from eutopic endometrium and from ectopic endometrium (endometriotic lesions) demonstrate impaired ability to decidualize in vitro, a finding highly suggestive of an intrinsic abnormality in the progesterone-signaling pathway (Klemmt P A et al. (2006) Fertil Steril 85:564-72). Others have observed dysregulation of progesterone target genes in cultured endometrial stromal cells from women with endometriosis, significant insofar as the progesterone level in the culture medium is well controlled (Bruner-Tran K L et al. (2002) J Clin Endocrinol Metab 87:4782-91). A model for progesterone resistance based on differential PR isoform expression has been described for ectopic endometrium (Bulun S E et al. (2006) Progesterone resistance in endometriosis: link to failure to metabolize estradiol. Mol Cell Endocrinol 248:94-103), and a reduced responsiveness to progesterone in eutopic endometrium has been implicated in disease pathogenesis (Osteen K G et al. (2005) Fertil Steril 83:529-37). The present gene expression findings are consistent with resistance to progesterone action in the endometrium of women with endometriosis. The current study provides a framework for further investigation as to the mechanism(s) underlying attenuated progesterone response in eutopic endometrium of women with endometriosis.

Example 2

This example investigates steroidogenic pathway enzymes in tissue and ESFs from women with and without endometriosis.

Figure 5A:
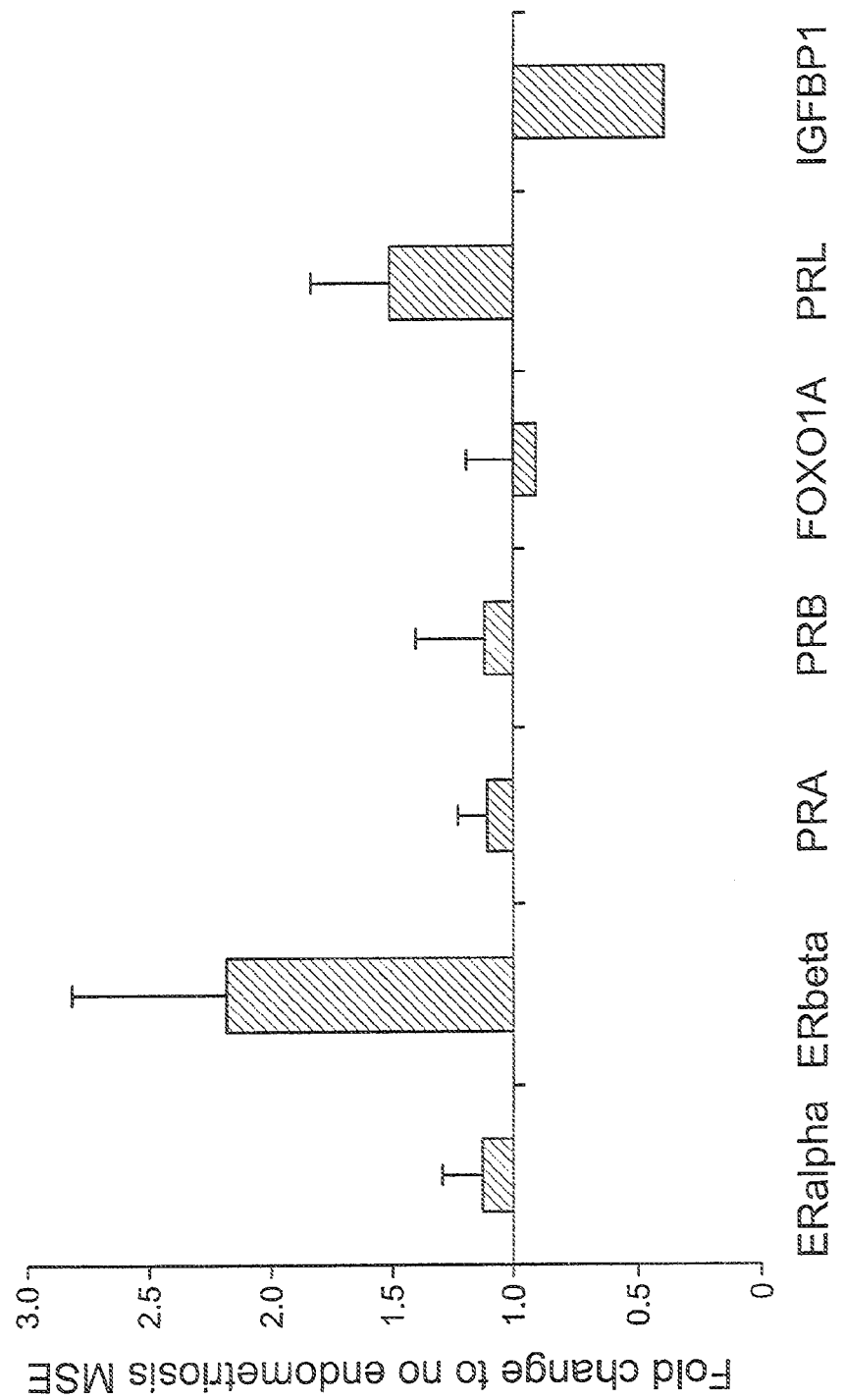
FIG. 5A. Gene expression in severe endometriosis MSE biopsies compared to non-endometriosis MSE samples.
Figure 5C:
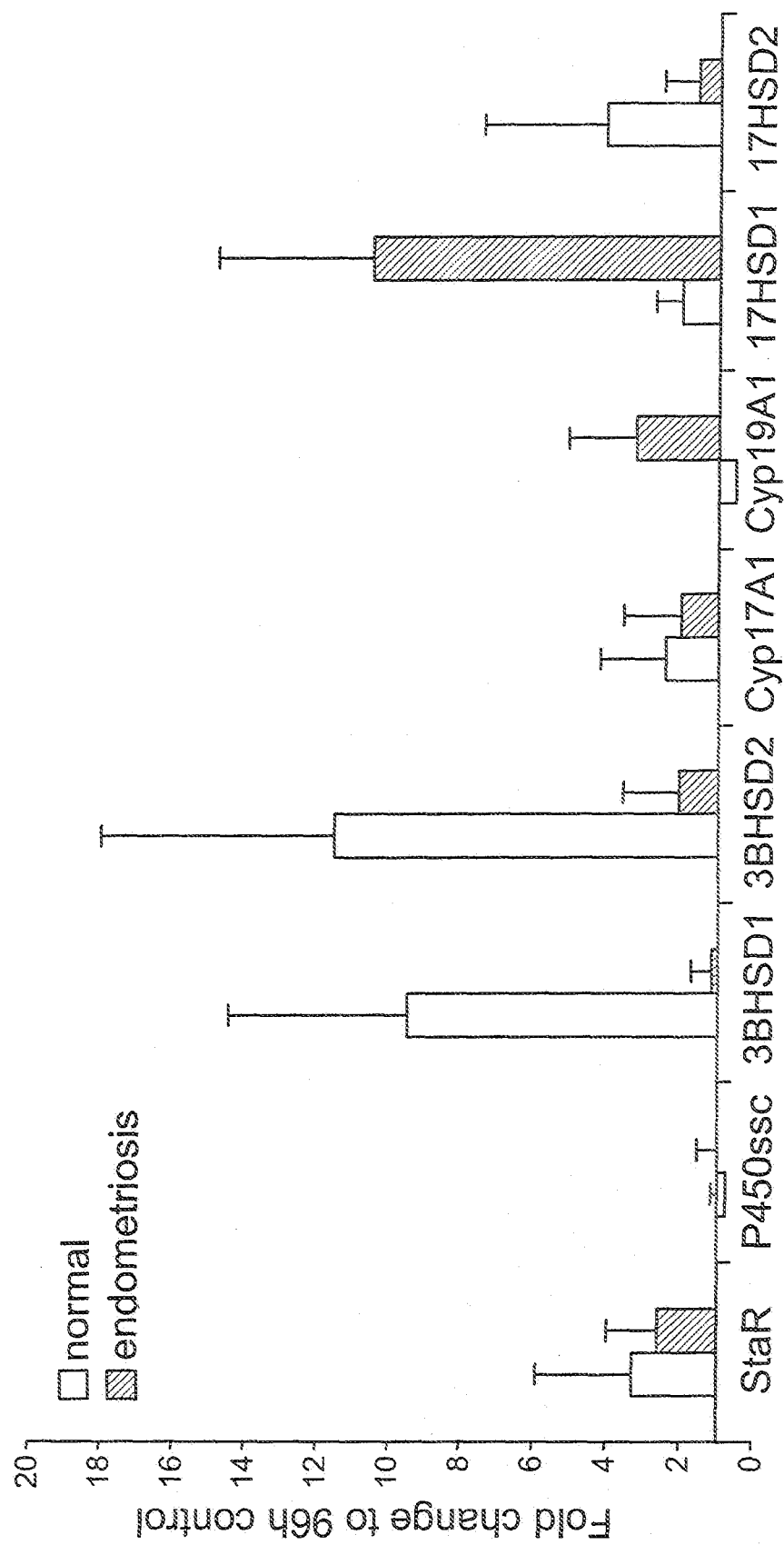
FIG. 5C. Steroidogenic gene expression in ESFs treated with 0.5 mM cAMP for 96 hours.
Figure 5E:
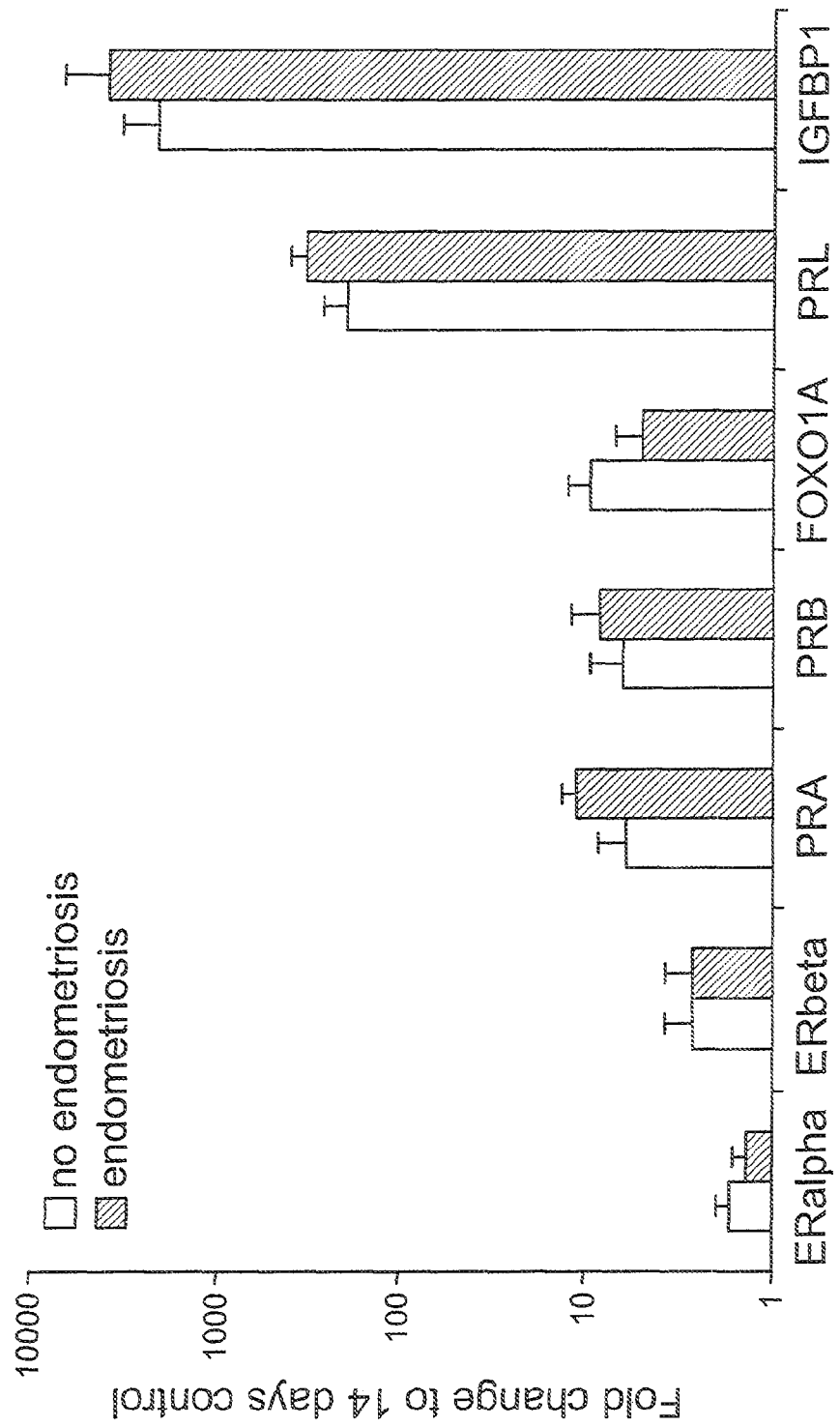
FIG. 5E. Gene expression in ESFs treated with E2/P4 for 14 days.

ESFs were isolated from endometrial biopsies from 15 women with and 7 women without endometriosis. After reaching confluence, cells were cultured with 1 µM $P_4$ (after $E_2$ 100 nM priming) in a time course of short (3, 6, 48 hours) and long (14 days) term culture, and 0.5 mM of 8-bromo-cAMP for 96 hours. IGFBP1 and PRL protein secretion was measured by ELISA. Alterations in expression of some $P_4$ and cAMP regulated genes (IGFBP1, PRL, FOXO1A, ERalpha, ERbeta, EBAF, somatostatin (SST), SST receptor 2, PRA, PRB) were determined by real-time quantitative (Q)RT-PCR. Purity of ESF populations at passage 2 was evaluated by immunohistochemistry using cytokeratin, vimentin and CD45 antibodies. Endometrial tissue biopsies were obtained from mid-secretory phase endometrium from 5 women without and 5 women with severe endometriosis. Regulation of steroidogenic enzymes StAR (UniGene ID Hs.521535), p450scc (UniGene ID Hs.303980), HSD3B1 (UniGene ID Hs.364941), HSD3B2 (, UniGene ID Hs.654399), Cyp17A1 (UniGene ID Hs.438016), Cyp19A1 (UniGene ID Hs.654384), HSD17B1 (HSD17B1 UniGene ID Hs.654385), HSD17B2 (HSD17B2, UniGene ID Hs.162795) by cAMP and/or $E_2/P_4$ was studied by Q-PCR. (FIG. 5)

Figure 6:
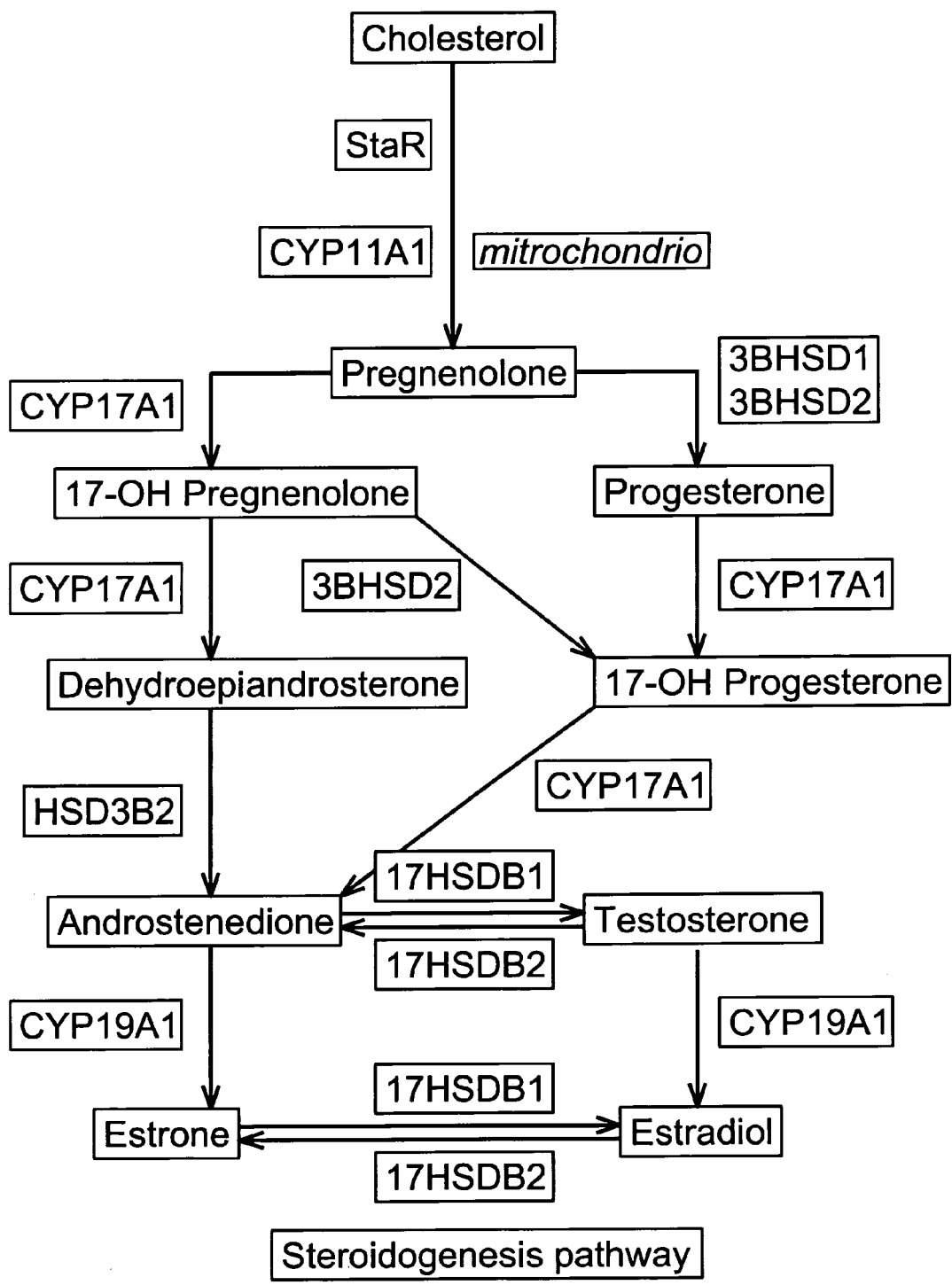
FIG. 6. Graphical overview of the steroidogenesis pathway.

CyclicAMP was a more potent trigger of decidualization, compared to $P_4$, as documented by gene and protein expression of decidualization markers. Also, cAMP and $P_4$ had different effects on decidualization of ESFs from women with vs. without endometriosis suggesting differences in activation of the cAMP pathway. Steroid hormone biosynthesis is known to be regulated by cAMP/PKA pathway and starts from activation of steroidogenic acute regulatory protein (StAR). StAR regulates cholesterol transport within mitochondria and to P450scc (side chain cleavage cytochrome, Cyp11A1), which converts cholesterol to pregnenolone. In ESFs, cAMP, but not $P_4$, increased the expression of both genes, however, without difference between cells from women with vs. without endometriosis. In tissue samples, StAR, but not P450scc, was significantly upregulated in endometrium from women with endometriosis compared to those without the disease. 3β-hydroxysteroid dehydrogenase (3βHSD) 1 & 2 catalyse the conversion of pregnenolone to $P_4$, 17OH to 17-OH-$P_4$ and DHEA to androstenedione. cAMP significantly up-regulated mRNAs for both genes in ESFs from women with vs. without endometriosis, suggesting decreased conversion of pregnenolone ($P_1$) to $P_4$. Down regulation of 3βHSD1, but not 3βHSD2, was observed in mid-secretory endometrial tissue and $P_4$ stimulated ESFs from women with endometriosis. Cyp17A1 (P450c17) is a cytochrome P450 enzyme that hydroxilates $P_1$ to $P_4$, or acts upon 17-OH-$P_4$ and 17-OHypregnenolone to split the side chain off the steroid nucleus. This enzyme was slightly upregulated by cAMP in ESFs from women with vs without endometriosis, and was slightly down-regulated in endometrial tissue and in ESfs stimulated with $P_4$. Aromatase (Cyp19A1) functions to aromatize androgens to estrogens (FIG. 6). Aromatase was not regulated by $P_4$ in ESFs, and was up-regulated by cAMP in women with endometriosis. In MSE, aromatase was elevated in women with endometriosis (14.5-fold), but was undetectable in normal women.

The 17-HSDβ-type 1 (17HSDB1) catalyzes conversion of $E_1$ to $E_2$ and testosterone to androstenedione in liver and endometrium, is regulated by $P_4$ and is down-regulated in endometriosis. In the present study, 17HSDB1 mRNA was 10-fold up-regulated by cAMP in ESFs from women with vs. without endometriosis. 17HSDB2 in ESCs was up-regulated by cAMP, however, to lesser extent.

This study demonstrates that activation of the PKA pathway stimulates $P_4$ synthesis in ESFs, suggesting regulation of decidualization of these cells and up-regulation of $P_4$-responsive genes. ESFs from women with endometriosis demonstrate altered steroidogenic pathway activation, with a decrease in $P_4$ and an increase in $E_2$ synthesis. This deficit of $P_4$ and accumulation of $E_2$ may be responsible for the growth and survival of endometriosis.

TABLE 9

Change in regulation of selected $P_4$ and cAMP regulated genes in patients with endometriosis as compared to patients without endometriosis.

| Gene | Unigene ID | Regulation |
|---|---|---|
| ESR1 | Hs.208124 | Up-regulated |
| ESR2 | Hs.660607 | Up-regulated |
| PGR (PRA) | Hs.32405 | Up-regulated |
| PGR (PRB) | Hs.32405 | Up-regulated |
| FOXO1 | Hs.370666 | Down-regulated |
| PRL | Hs.1905 | Up-regulated |
| IGFBP1 | Hs.642938 | Down-regulated |

Example 3

The aetiology and pathogenesis of endometriosis are not well understood. Hic-5 (Unigene ID 513530), an adaptor-like nuclear receptor co-activator, also known as transforming growth factor beta 1 induced transcript 1 and androgen receptor coactivator ARA55, potentiates the activation of reporter genes by all steroid receptors (GR, AR, MR, and PR), except the ER, and is responsive to progesterone. This example shows that dysregulation of Hic-5 is involved in progesterone resistance in endometriosis.

Figure 7:
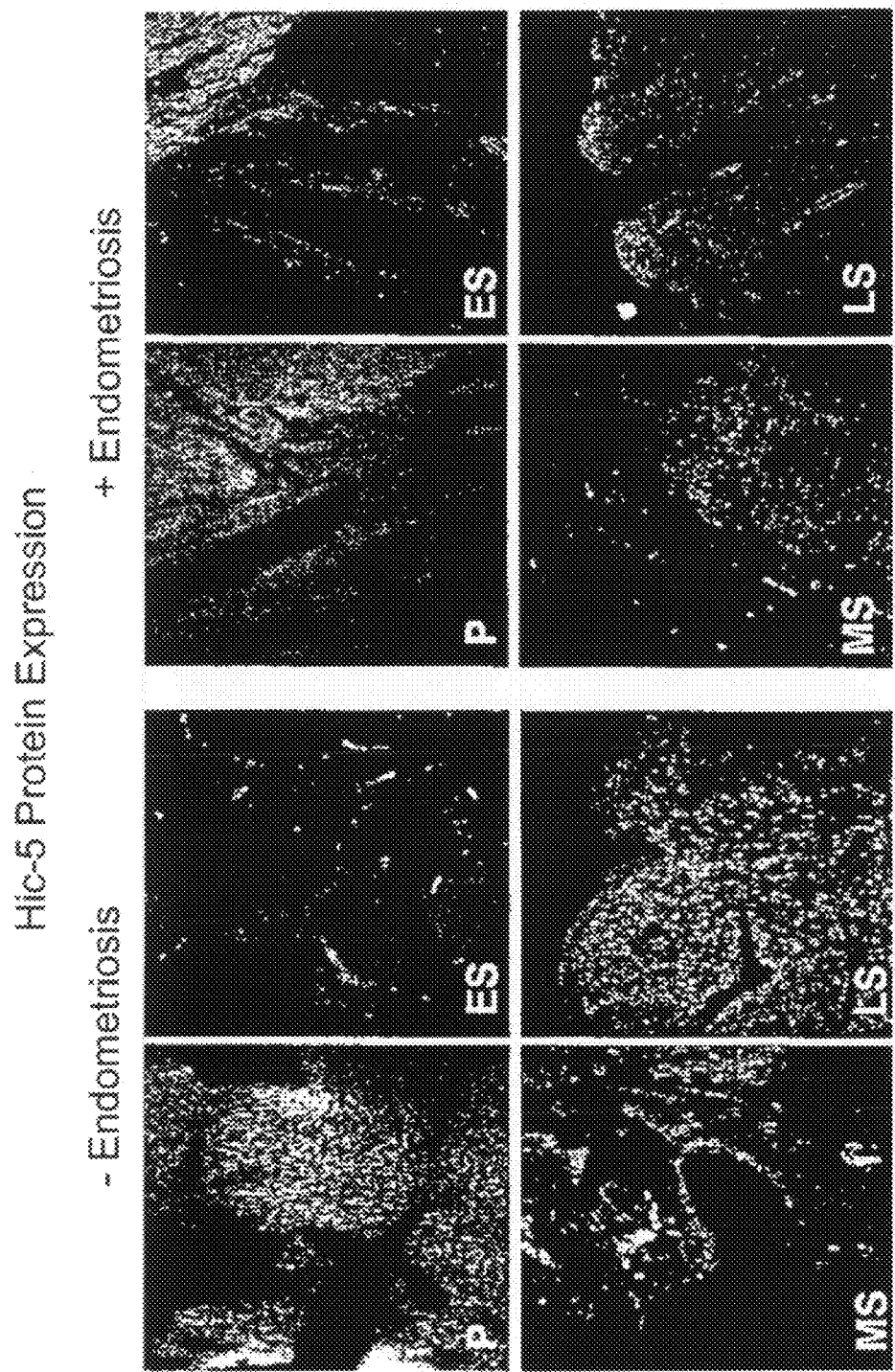
FIG. 7. Hic-5 protein localization during different phases of the ovulatory cycle in endometrial samples taken from patients with and without endometriosis.

Endometrial biopsies were obtained from mid-secretory phase endometrium from women without and with endometriosis: proliferative phase endometrium (PE) n=3 and n=4 respectively; early secretory endometrium (ESE) n=3 for both groups; mid-secretory endometrium n=5 for both groups; late secretory endometrium n=3 and n=4 respectively. Localization of Hic-5 protein was verified by immunofluorescence in full-thickness endometrial biopsies (FIG. 7). Endometrial stromal fibroblasts (ESFs) were isolated from biopsies from 15 women with and 7 women without endometriosis. Cells were decidualized with 1 μM $P_4$ (after $E_2$ 10 nM priming) for 14 days, or 0.5 mM of 8-bromo-cAMP for 96 hours. Hic-5, progesterone receptors (PRA and PRB) and Wnt4 gene expression was analysed by real-time-RT-PCR.

Figure 8:
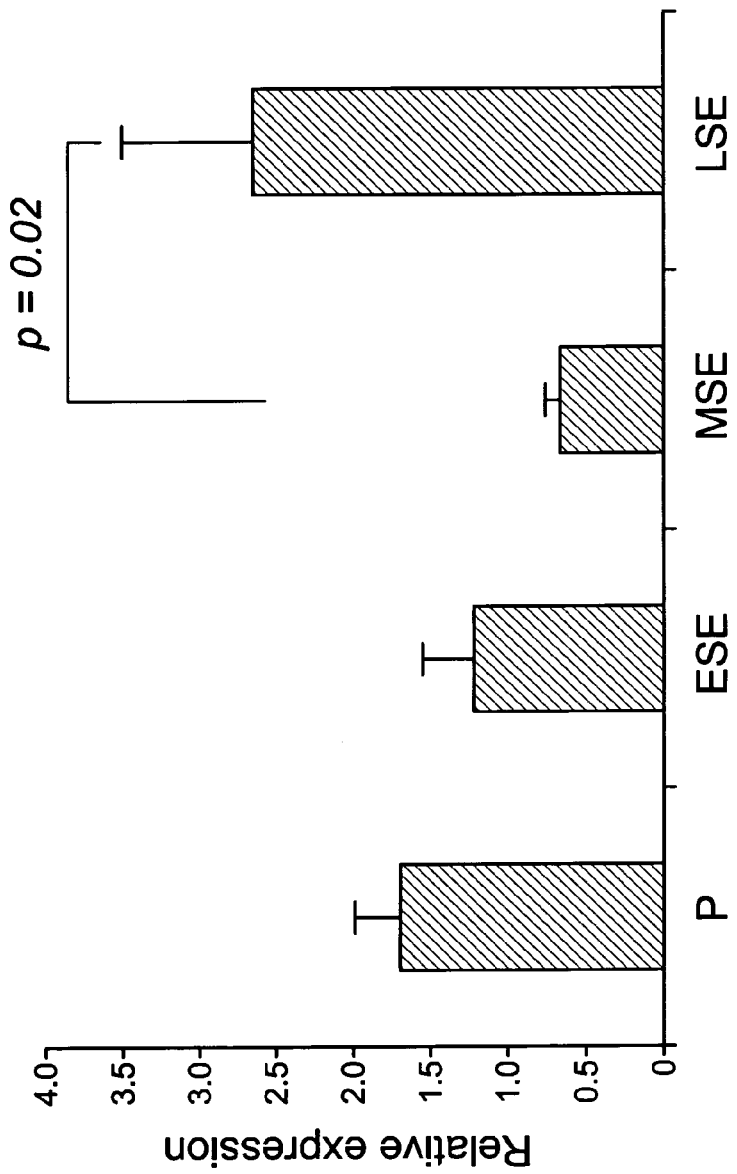
FIG. 8. Expression of Hic-5 mRNA in human endometrium throughout the menstrual cycle in patients without endometriosis.
Figure 9:
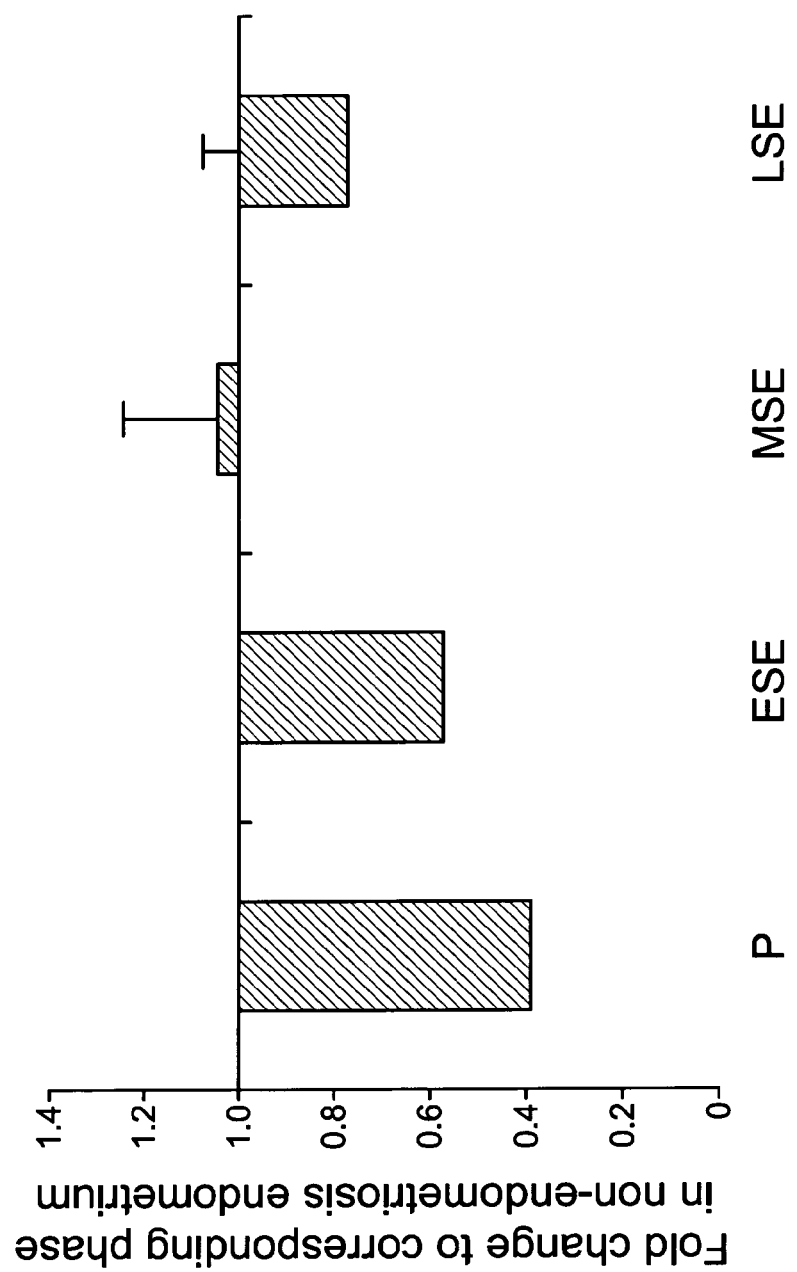
FIG. 9. Hic-5 mRNA expression levels in endometrium from women with endometriosis relative to levels in women without endometriosis throughout the menstrual cycle.
Figure 10:
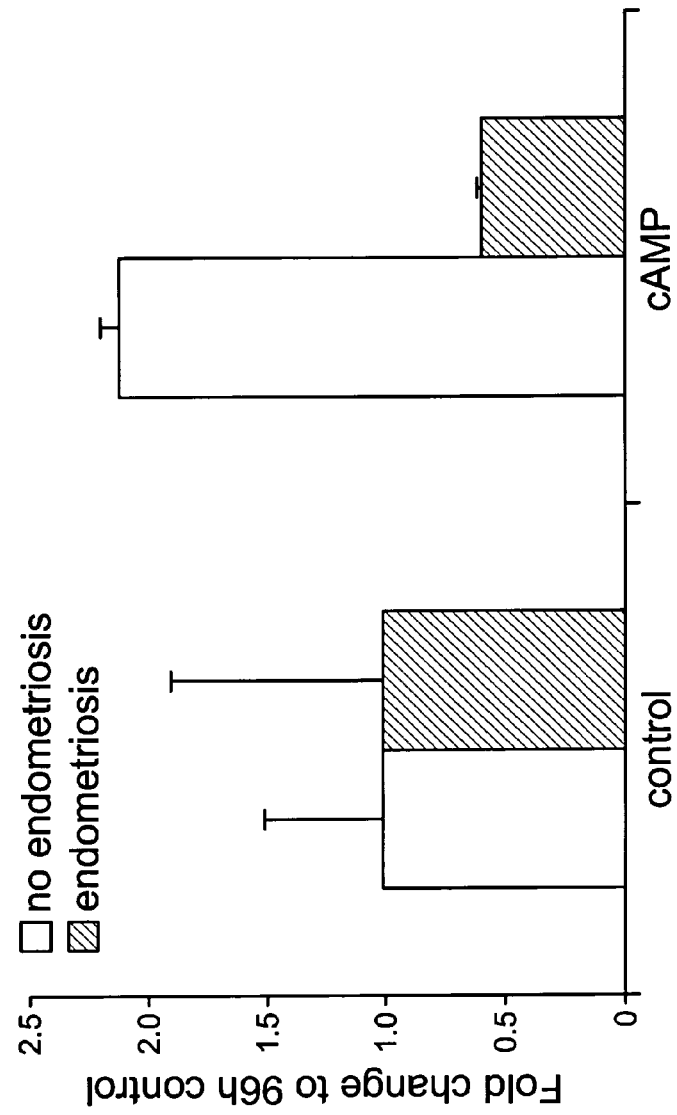
FIG. 10. Expression of Hic5 in human endometrial stromal fibroblasts decidualized with 0.5 mM cAMP for 96 hours.
Figure 11:
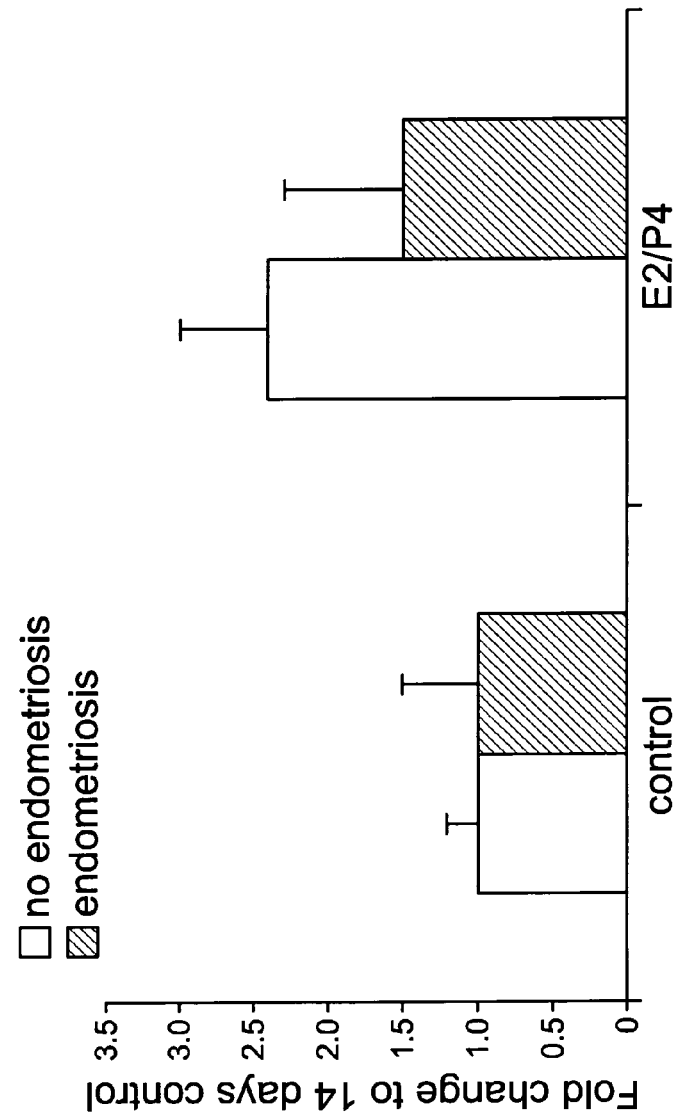
FIG. 11. Expression of Hic5 in human endometrial stromal fibroblasts decidualized with 10 nM E2/1 µM P4 for 14 days.
Figure 12:
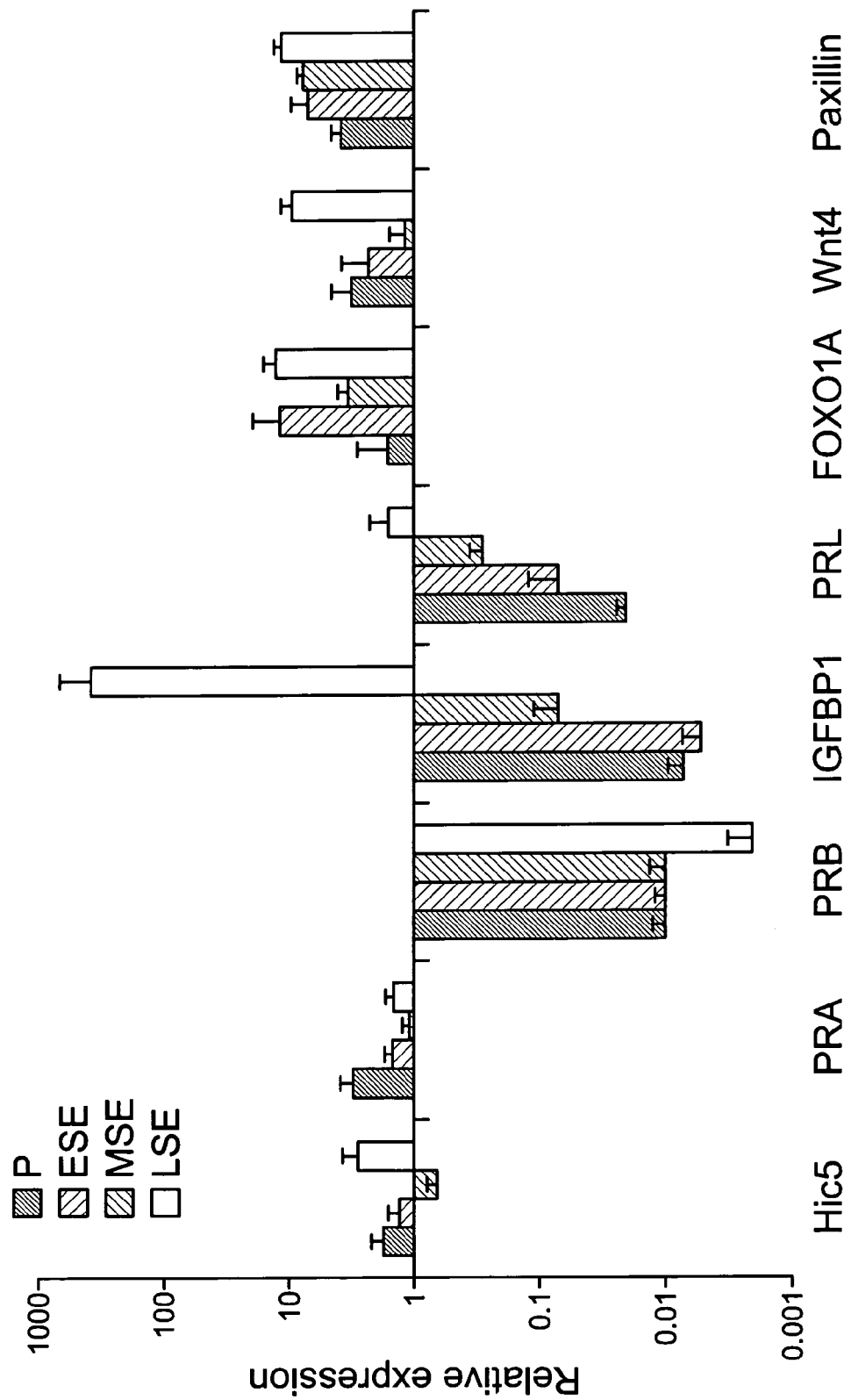
FIG. 12. Progesterone-regulated genes in endometrial biopsies from women without endometriosis.
Figure 13:
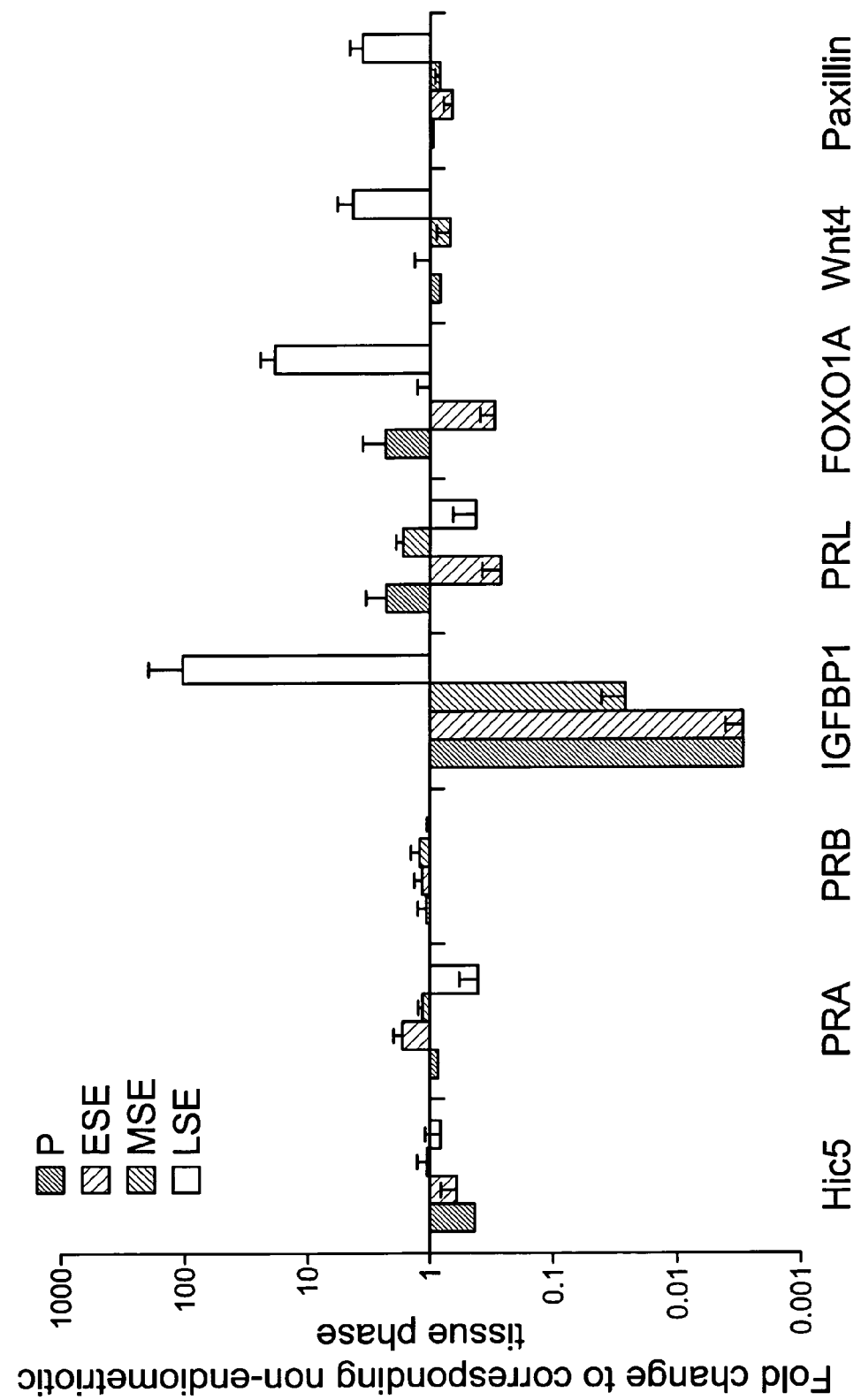
FIG. 13. Dysregulation of progesterone-responsive genes in endometrial biopsy from women with vs. without endometriosis.
Figure 14:
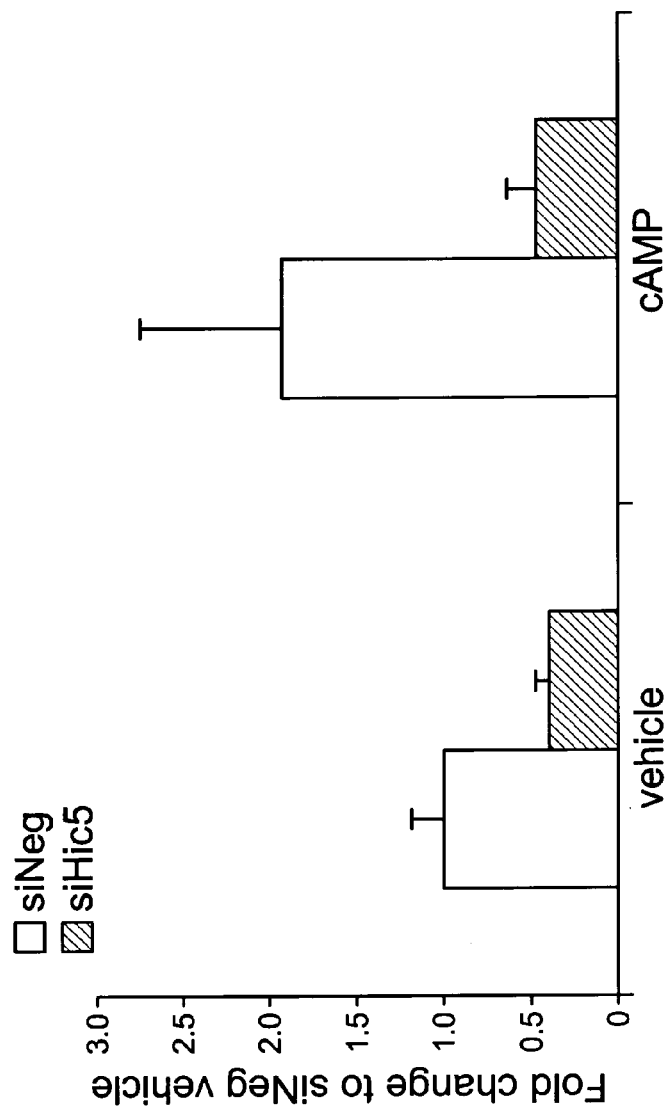
FIG. 14. Levels of Hic-5 mRNA after transfection with control and anti-Hic-5 siRNA.
Figure 15:
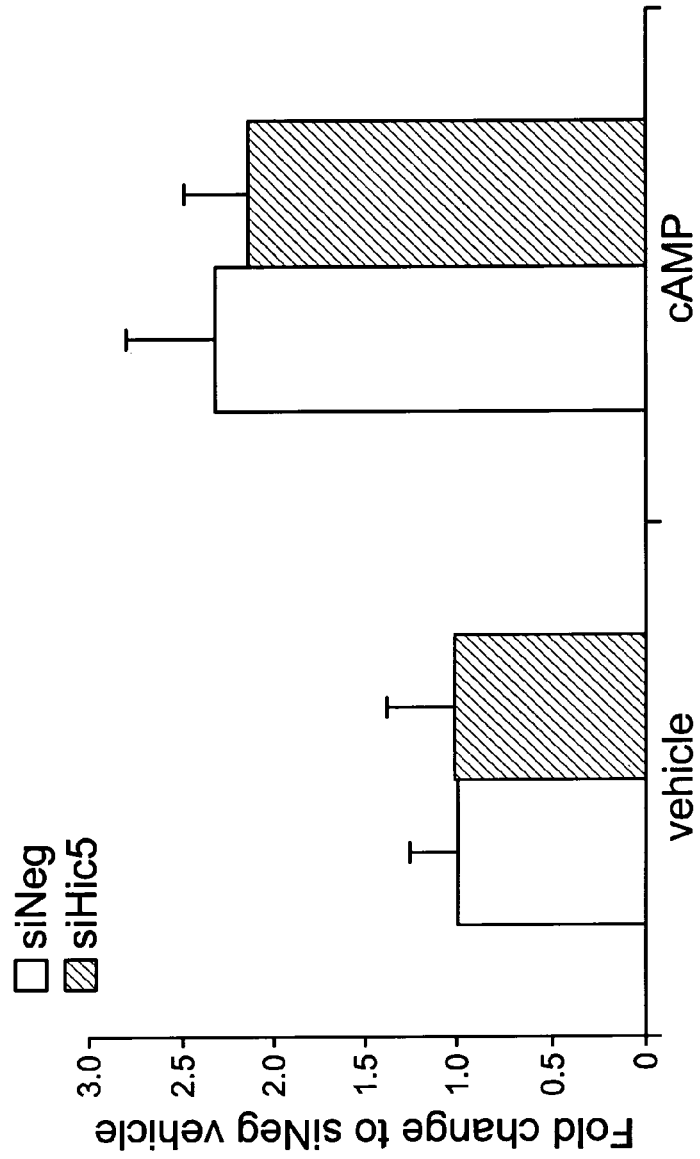
FIG. 15. Levels of Paxillin mRNA after transfection with control and anti-Hic-5 siRNA.
Figure 16:
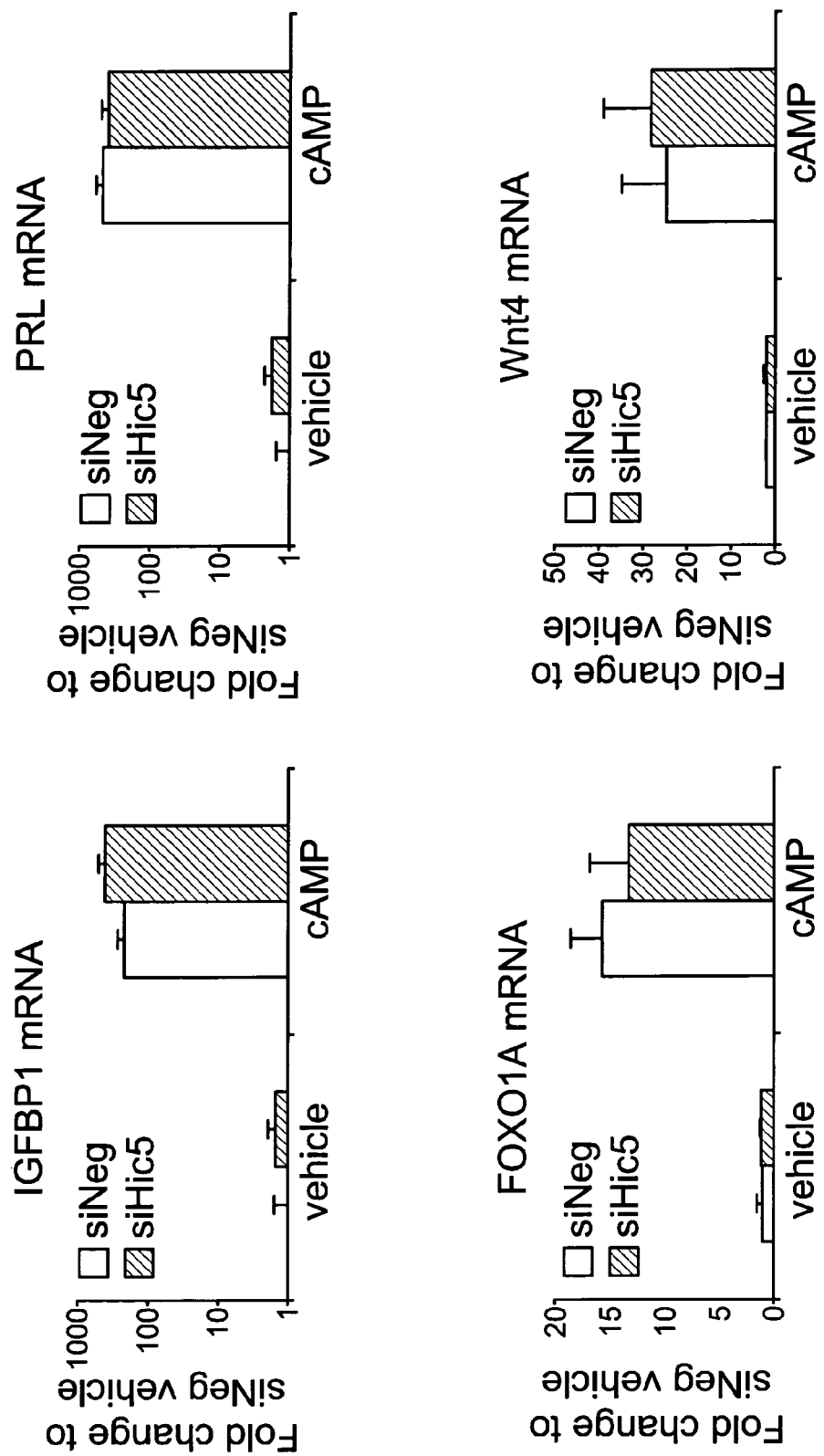
FIG. 16. Levels of IGFBP1, PRL, FOXO1A, and Wnt4 mRNA after transfection with control and anti-Hic-5 siRNA.
Figure 17:
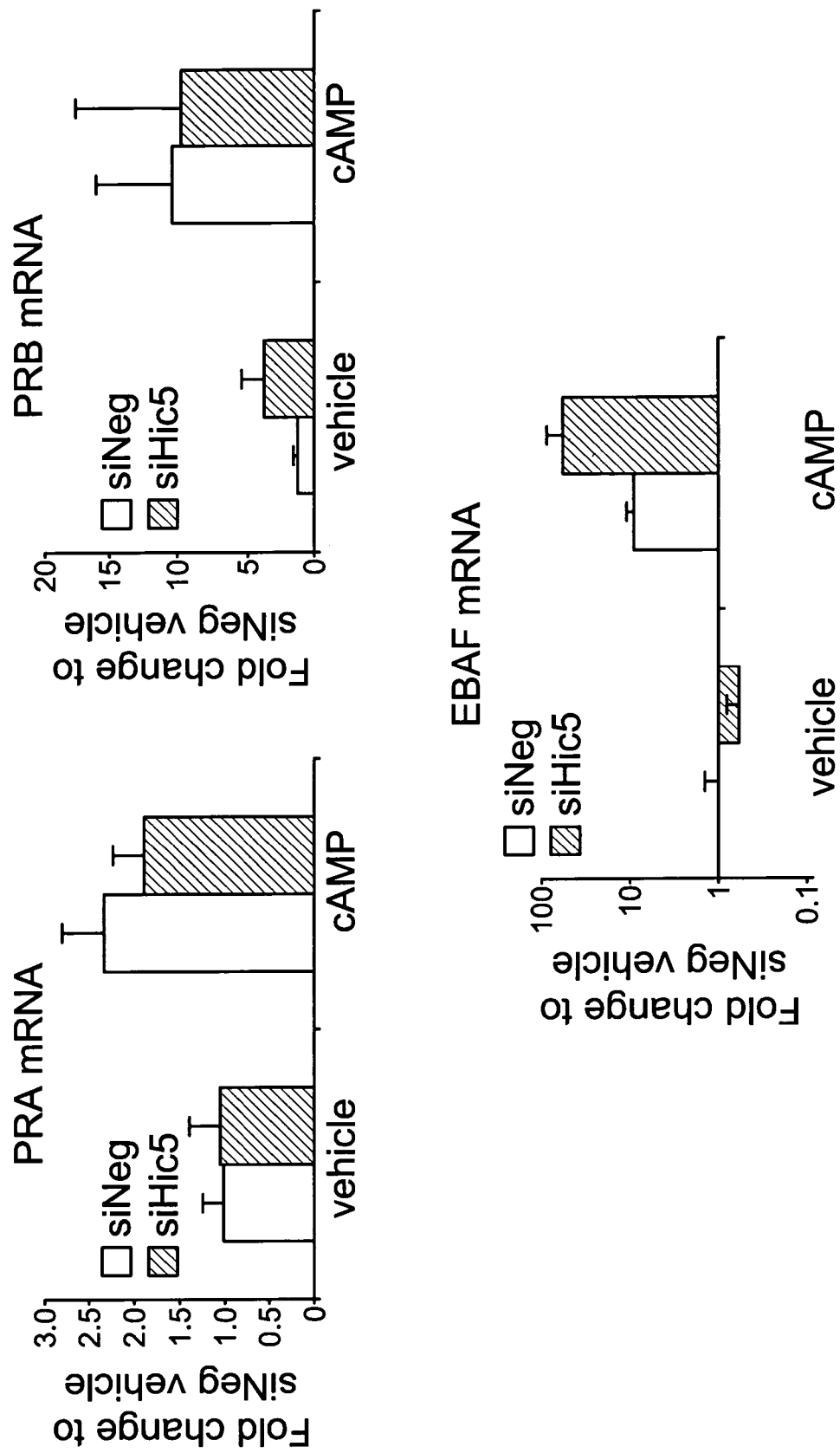
FIG. 17. Levels of PRA, PRB, and EBAF mRNA after transfection with control and anti-Hic-5 siRNA.

Immunofluorescence revealed strong expression of Hic-5 in myometrium without cyclic variation. In endometrium, Hic-5 was restricted to the stromal compartment, with strong immunoexpression in PE, which decreased in ESE, and subsequently increased in MSE and towards the end of the cycle. Hic-5 mRNA expression in normal patients replicated the protein expression pattern, with gradual decrease from PE to ESE and with a subsequent rise in MSE and LSE (FIG. 8). When levels of Hic-5 mRNA from women with endometriosis were compared to those from women without endometriosis, there was a marked down regulation during the P, ESE, and LSE phases (FIG. 9).

Its expression was negatively correlated with PRB and positively with Wnt4 mRNA expression throughout the cycle in every patient ($r^2$=−0.687, p≦0.01 and $r^2$=0.618, p≦0.05 respectively), and it correlated positively with PRA mRNA expression when patients in each phase were pooled ($r^2$=0.598, p≦0.05). In endometrial biopsies from endometriotic women Hic-5 gene expression was decreased and dysregulated, as were expression of PRs and Wnt4 in each cycle phase. In culture experiments, ESFs demonstrated increased Hic-5 gene expression upon decidualization with both cAMP and E2/P4 stimulation in cells from normal, but not endometriotic women.

This example demonstrates the expression of Hic-5 gene and protein in human endometrium, its correlation with PRs, and regulation by progesterone and cAMP in cultured ESFs. Dysregulation of Hic-5 in eutopic endometrium from women with endometriosis suggests its involvement in the pathogenesis of molecular changes associated with progesterone resistance in this disorder.

Example 4

Growth of ectopic endometrial tissues in the pelvic cavity, which is a hallmark of endometriosis, is associated with elevated levels of inflammatory cytokines and increased number of activated macrophages in the peritoneal environment. While numerous studies have shown differential gene expression of ectopic endometrium from women with endometriosis, increasing evidence also shows that eutopic endometrium from women with endometriosis has dysregulated expression of genes, which are implicated in proliferation of the disease, as well as infertility and bleeding. In this example, the expression of inflammatory-associated genes in cultured eutopic endometrial stromal cells from women with versus without endometriosis was examined using quantitative RT-PCR. Interleukin-8 (IL-8), a cytokine implicated in endometrial cell attachment, invasion, and cell growth, is up-regulated 19 fold in eutopic endometrial stromal cells isolated from women with endometriosis compared with cells from women without endometriosis (P=0.03). Interleukin-1 beta and cyclooxygenase-2 mRNA expression were similar in cultured endometrial stromal cells from women with vs. without endometriosis. Cell proliferation was similar in eutopic endometrial stromal cells from women with versus without endometriosis when cultured in 0%, 2%, or 10% charcoal stripped FBS-containing medium or in the presence of insulin. Increased IL-8 production in endometriosis is accompanied by a strong increased phosphorylation of ERK 1/2 (P=0.04), a signaling molecule shown to activate IL-8 expression in endometrial stromal cells. Progesterone treatment within 60 min successfully diminished the high basal ERK phosphorylation in eutopic endometrial stromal cells from patients with endometriosis, resulting in an amount of ERK phosphorylation similar to the level in cells from patients without endometriosis. Since phosphorylation of ERK and IL-8 expression increases cell migration and invasion of endometrial stromal cells, dysregulation of MAPK activity and IL-8 expression in the eutopic endometrial stromal cells of women with endometriosis may be associated with the pathophysiology and spread of the disease.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of providing a prognosis for endometriosis, the method comprising the steps of:
   obtaining a biological sample from a human subject suspected of or having endometriosis,
   detecting, in the biological sample altered expression (over or under expression of at least 50%) of a gene or protein wherein said altered expression is selected from the group consisting of over expression of the S100 calcium binding protein A8 (S100A8) gene or protein, under expression of the Indian hedgehog (IHH) gene or protein, over expression of the proenkephalin (PENK) gene or protein, under expression of the cytochrome P450 subfamily XXVIA (Cyp26A1) gene or protein, under expression of the leukotriene B4 receptor (BLTR2) gene or protein, under expression of the mitogen-activated protein kinase 4 (MAPK4) gene or protein, under expression of the secretoglobin family 2A, member 2 (SCGB2A2) gene or protein, under expression of the calpain 6 (CAPN6) gene or protein, and under expression of the mitogen-inducible gene 6 (MIG6) or protein, wherein the altered expression correlates with the prognosis for endometriosis, and the prognosis is provided.

2. The method of claim 1, wherein protein is detected.

3. The method of claim 1, wherein RNA expression is detected.

4. The method of claim 1, wherein the sample is an endometrial biopsy.

5. The method of claim 1, wherein the altered expression is the over expression of the S100A8 gene or protein and the sample comprises proliferative phase endometrial tissue or mid-secretory phase endometrial tissue.

6. The method of claim 1, wherein the altered expression is selected from the over expression of the of the PENK gene or protein under expression of the Cyp26A1 gene or protein, under expression of the SCGB2A2 gene or protein, under expression of the MIG6 gene or protein, and under expression of the CAPN6 gene or protein.

7. The method of claim 6, wherein the sample is a sample of early secretory phase endometrial cells or tissue.

8. The method of claim 1, wherein the altered expression is selected from the over expression of the MAPK4 gene or protein, and over expression of the BLTR2 gene or protein.

9. The method of claim 8, wherein the sample is a sample of mid secretory phase endometrial tissue.

10. The method of claim 1, wherein altered expression is the under expression of the IHH gene and the sample comprises proliferative phase endometrial tissue.

11. The method of claim 1, wherein the altered expression is under expression of the SCGB2A2 gene or protein and the sample comprises early secretory or mid-secretory phase endometrial tissue.

12. The method of claim 1, wherein the altered expression is under expression of the Cyp26A1 gene or protein and the sample comprises early secretory or mid-secretory phase endometrial tissue.

13. The method of claim 1, wherein the altered expression is under expression of the CAPN6 gene or protein and the sample comprises early secretory or mid-secretory phase endometrial tissue.

14. The method of claim 1, wherein the altered expression is over expression of the MAPK4 gene or protein and the sample comprises mid-secretory phase endometrial tissue.

15. The method of claim 1, wherein the altered expression is over expression of the BLTR2 gene or protein and the sample comprises mid-secretory phase endometrial tissue.

16. The method of claim 1, wherein the altered expression is under expression of the MIG6 gene or protein and the sample comprises early secretory phase endometrial tissue.

17. The method of claim 1, wherein the altered expression is over expression of the S100 calcium binding protein A8 (S100A8) gene or protein and the sample comprises proliferative phase endometrial tissue.

18. The method of claim 1, wherein the altered expression is selected from the over expression of the of the PENK gene or protein and the sample comprises early secretory phase endometrial tissue.

* * * * *

UNITED STATES PATENT AND TRADEMARK OFFICE
CERTIFICATE OF CORRECTION

PATENT NO.        : 7,871,778 B2
APPLICATION NO.   : 12/109099
DATED             : January 18, 2011
INVENTOR(S)       : Giudice It is certified that error appears in the above-identified patent and that said Letters Patent is hereby corrected as shown below:

In the Specification:

In the "STATEMENT AS TO RIGHTS TO INVENTIONS MADE UNDER FEDERALLY SPONSORED RESEARCH OR DEVELOPMENT" section, Column 1, Line 16, please delete "This invention was made in part with Government support under grant HD031398 awarded by the National Institutes of Health. The United States government has certain rights in this invention" and insert --This invention was made with government support under grant no. HD031398 awarded by the National Institutes of Health. The government has certain rights in the invention.--.

In the Claims:

Claim 18, Column 66, Line 10: please delete the second (repeated) instance of "of the".

Signed and Sealed this
Eighteenth Day of October, 2011

David J. Kappos
*Director of the United States Patent and Trademark Office*

UNITED STATES PATENT AND TRADEMARK OFFICE
CERTIFICATE OF CORRECTION

PATENT NO. : 7,871,778 B2  
APPLICATION NO. : 12/109099  
DATED : January 18, 2011  
INVENTOR(S) : Giudice It is certified that error appears in the above-identified patent and that said Letters Patent is hereby corrected as shown below:

In the Claims:

Claim 1, Column 63, Line 54-56: please delete "under expression of the leukotriene B4 receptor (BLTR2) gene or protein," and insert --over expression of the leukotriene B4 receptor (BLTR2) gene or protein,--.

Claim 1, Column 63, Line 56-57: please delete "under expression of the mitogen-activated protein kinase 4 (MAPK4) gene or protein," and insert --over expression of the mitogen-activated protein kinase 4 (MAPK4) gene or protein,--.

Signed and Sealed this  
First Day of January, 2013

David J. Kappos  
*Director of the United States Patent and Trademark Office*